US008039225B2

(12) United States Patent
Wilkes et al.

(10) Patent No.: US 8,039,225 B2
(45) Date of Patent: Oct. 18, 2011

(54) METHOD TO IDENTIFY PATIENTS AT RISK FOR LUNG TRANSPLANT REJECTION

(75) Inventors: David S. Wilkes, Indianapolis, IN (US); Michael Klemsz, Indianapolis, IN (US)

(73) Assignee: Indiana University Research & Technology Corporation, Indianapolis, IN (US)

( * ) Notice: Subject to any disclaimer, the term of this patent is extended or adjusted under 35 U.S.C. 154(b) by 0 days.

(21) Appl. No.: 13/082,203

(22) Filed: Apr. 7, 2011

(65) Prior Publication Data

US 2011/0183356 A1    Jul. 28, 2011

Related U.S. Application Data

(63) Continuation of application No. 12/823,570, filed on Jun. 25, 2010, now Pat. No. 7,939,281, which is a continuation of application No. 12/171,661, filed on Jul. 11, 2008, now Pat. No. 7,759,075, which is a continuation of application No. PCT/US2007/060533, filed on Jan. 13, 2007.

(60) Provisional application No. 60/759,195, filed on Jan. 13, 2006.

(51) Int. Cl.
   *G01N 33/543*     (2006.01)
   *A61K 39/00*      (2006.01)

(52) U.S. Cl. ......... 435/7.21; 435/7.1; 436/501; 424/9.1; 424/184.1; 530/300; 530/350; 530/356

(58) Field of Classification Search ........................ None
   See application file for complete search history.

(56) References Cited

U.S. PATENT DOCUMENTS

| | | | |
|---|---|---|---|
| 4,444,879 A | 4/1984 | Foster et al. | 435/7 |
| 5,962,025 A | 10/1999 | Carbone et al. | 424/520 |
| 5,990,274 A | 11/1999 | Wang | 530/317 |
| 6,410,696 B1 | 6/2002 | Davalian et al. | 530/405 |
| 6,911,220 B1 | 6/2005 | Sachs | 424/580 |
| 7,718,765 B2 | 5/2010 | Postlethwaite et al. | 530/300 |
| 7,759,075 B2 | 7/2010 | Wilkes et al. | 435/7.21 |
| 2003/0078208 A1 | 4/2003 | Wilkes | 514/12 |
| 2007/0142286 A1 | 6/2007 | Postlethwaite et al. | 514/12 |
| 2011/0020838 A1 | 1/2011 | Wilkes et al. | 435/7.1 |

FOREIGN PATENT DOCUMENTS

| | | |
|---|---|---|
| WO | 98/02173 A1 | 1/1998 |
| WO | 2007/059211 A2 | 5/2007 |

OTHER PUBLICATIONS

Birk et al., "The 60-kDa heat shock protein modulates allograft rejection," *Proc. Natl. Acad. Sci USA* 96:5159-5163, 1999.
Burlingham et al., "Loss of Tolerance to a Maternal Kidney Transplant is Selective for HLA Class II: Evidence from Trans-vivo DTH and Alloantibody Analysis," *Human Immunology* 61:1395-1402, 2000.
Cai et al., "Minor H Antigen HA-1-specific Regulator and Effector $CD8^+$ T Cells, and HA-1 Microchimerism, in Allograft Tolerance," *J. Exp. Med.* 199(7):1017-1023, 2004.
Chen et al., "Peripheral deletion of antigen-reactive T cells in oral tolerance," *Nature* 376:177-180, 1995.
Cremer et al., "Type XI Collagen-Induced Arthritis in the Lewis Rat," *J. Immunol.* 153:824-832, 1994.
Delclaux et al., "Alveolar neutrophils in endotoxin-induced and bacteria-induced acute lung injury in rats," *Am. J. Physiol. (Lung Cell. Mol. Physiol.17)* 273:L104-L112, 1997.
Duquesnoy et al., "Evidence for Heat Shock Protein Immunity in a Rat Cardiac Allograft Model of Chronic Rejection," *Transplantation* 67(1):156-164, 1999.
Estenne et al., "Bronchiolitis Obliterans Syndrome 2001: An Update of the Diagnostic Criteria," *J Heart Lung Transplant* 21:297-310, 2002.
Faria et al., "Oral Tolerance: Mechanisms and Therapeutic Applications," *Advances in Immunology* 73:153-264, 1999.
Fedoseyeva et al., "De Novo Autoimmunity to Cardiac Myosin After Heart Transplantation and Its Contribution to the Rejection Process," *J. Immunol.* 162:6836-6842, 1999.
Fernandez-Madrid et al., "Autoimmunity to Collagen in Human Lung Cancer," *Cancer Research* 56:121-126, Jan. 1, 1996.
Garrovillo et al., "Indirect Allorecognition in Acquired Thymic Tolerance: Induction of Donor-Specific Tolerance to Rat Cardiac Allografts by Allopeptide-Pulsed Host Dendritic Cells," *Transplantation* 68(12):1827-1834, 1999.
Garside et al., "Mechanisms of Oral Tolerance," *Critical Reviews™ in Immunology* 17:119-137, 1997.
Hanson et al., "The Human α2(XI) Collagen Gene (COL11A2) Maps to the Centromeric Border of the Major Histocompatibility Complex on Chromosome 6," *Genomics* 5:925-931, 1989.
Haque et al., "Evidence for Immune Responses to a Self-Antigen in Lung Transplantation: Role of Type V Collagen-Specific T Cells in the Pathogenesis of Lung Allograft Rejection," *J. Immunol.* 169:1542-1549, 2002.
Hirt et al., "Development of Obliterative Bronchiolitis after Allogeneic Rat Lung Transplantation: Implication of Acute Rejection and the Time Point of Treatment," *J Heart Lung Transplant* 18:542-548, 1999.

(Continued)

*Primary Examiner* — Lisa Cook

(57) ABSTRACT

Various embodiments include methods for diagnosing and treating medical conditions that involve an autoimmune response to connective tissue such as collagen found in organs such as the lung. In one method pulmonary disease and disorders such as Idiopathic Pulmonary Fibrosis (IPF) are diagnosed by analyzing fluid or tissue samples obtained from a patient for evidence of an autoimmune response to various types of collagen including, for example, Type V. One type of assay for evidence of an autoimmune response to Type V collagen comprises the steps of obtaining a fluid or tissue sample from a patient, contacting at least a portion of the sample with antigen to anti-Type V collagen antibody and monitoring the mixture of sample and antigen for changes indicative of the presence of anti-Type V collagen in the sample. Another embodiment includes treating pulmonary diseases such as IPF by administering a therapeutically effective dose of epitopes of various collagens including Type V collagen.

6 Claims, 28 Drawing Sheets

OTHER PUBLICATIONS

Hudson et al., "Alport's Syndrome, Goodpasture's Syndrome, and Type IV Collagen," *N. Engl. J. Med. 348*:2543-2556, 2003.

Ishido et al., "Induction of Donor-Specific Hyporesponsiveness and Prolongation of Cardiac Allograft Survival by Jejunal Administration of Donor Splenocytes," *Transplantation 68*(9):1377-1382, 1999.

Joo et al., "T-Cell Mediated Responses in a Murine Model of Orthotopic Corneal Transplantation," *Investigative Ophthalmology & Visual Science 36*(8):1530-1540, 1995.

Konomi et al., "Localization of Type V Collagen and Type IV Collagen in Human Cornea, Lung, and Skin," *Am J Pathol 116*:417-426, 1984.

Lowry et al., "Immune Mechanisms in Organ Allograft Rejection," *Transplantation 40*(2):183-188, 1985.

Madri et al., "Collagen Polymorphism in the Lung. An Immunochemical Study of Pulmonary Fibrosis," *Human Pathology 11*(4):353-366, 1980.

Madri et al., "Isolation and Tissue Localization of Type $AB_2$ Collagen From Normal Lung Parenchyma," *Am J Pathol 94*:323-331, 1979.

Marck et al., "Lung Transplantation in the Rat," *Journal of Surgical Research 35*:149-158, 1983.

Mares et al., "Type V Collagen Modulates Alloantigen-Induced Pathology and Immunology in the Lung," *Am. J. Respir. Cell Mol. Biol. 23*:62-70, 2000.

Matsumura et al., "Assessment of Pathological Changes Associated With Chronic Allograft Rejection and Tolerance in Two Experimental Models of Rat Lung Transplantation," *Transplantation 59*(11):1509-1517, 1995.

Mayer, "Short Analytical Review. Oral Tolerance: New Approaches, New Problems," *Clinical Immunology 94*(1):1-8, 2000.

Morris et al., "Type XI collagen is a Heterotrimer with the Compositions $(1\alpha,2\alpha,3\alpha)$ Retaining Non-triple-helical Domains," *J. Biol. Chem. 262*(23):11345-11350, 1987.

Prop et al., "Lung Allograft Rejection in the Rat," *Transplantation 40*(1):25-30, 1985.

Rodriguez et al., "Immune Regulation and Graft Survival in Kidney Transplant Recipients are Both Enhanced by Human Leukocyte Antigen Matching," *American Journal of Transplantation 4*:537-543, 2004.

Sayegh et al., "Induction of immunity and oral tolerance with polymorphic class II major histocompatibility complex allopeptides in the rat," *Proc. Natl. Acad. Sci. USA 89*:7762-7766, 1992.

Sayegh et al., "Novel immunotherapeutic strategies using MHC derived peptides," *Kidney International 49*(53):S-13-S-20, 1996.

Schwarze et al., "Null Alleles of the COL5A1 Gene of Type V Collagen Are a Cause of the Classical Forms of Ehlers-Danlos Syndrome (Types I and II)," *Am. J. Hum. Genet. 66*:1757-1765, 2000.

Sekine et al., "Role of Passenger Leukocytes in Allograft Rejection. Effect of Depletion of Donor Alveolar Macrophages on the Local Production of TNF-$\alpha$, T Helper 1/T Helper 2 Cytokines, IgG Subclasses, and Pathology in a Rat Model of Lung Transplantation," *J. Immunol. 159*:4084-4093, 1997.

Sharples et al., "Risk Factors for Bronchiolitis Obliterans: A Systemic Review of Recent Publications," *J Heart Lung Transplant 21*:271-281, 2002.

Smith, Jr. et al, "Interaction of Proteoglycans with the Pericellular $(1\alpha,2\alpha,3\alpha)$ Collagens of Cartilage," *J. Biol. Chem. 260*(19):10761-10767, 1985.

Sumpter et al., "Role of autoimmunity in organ allograft rejection: a focus on immunity to type V collagen in the pathogenesis of lung transplant rejection," *Am. J. Physiol. Lung Cell Mol. Physiol. 286*:L1129-L1139, 2004.

Teodoro et al., "Architectural remodelling in lungs of rabbits induced by type V collagen immunization: a preliminary morphologic model to study diffuse connective tissue diseases," *Pathology Research and Practice 200* 10, Research Library 2004.

Torrealba et al., "Metastable Tolerance to Rhesus Monkey Renal Transplants Is Correlated with Allograft TGF-$\beta 1^+$ $CD4^+$ T Regulatory Cell Infiltrates," *J. Immunol. 172*:5753-5764, 2004.

Trulock, "Lung Transplantation," *Am J Respir Crit Care Med 155*:789-818, 1997.

VanBuskirk et al., "Patterns of Allosensitization in Allograft Recipients," *Transplantation 65*(8):1115-1123, 1998.

Whitacre et al., "Oral Tolerance in Experimental Autoimmune Encephalomyelitis," *J. Immunol. 147*(7):2155-2163, 1991.

Wilkes et al., "Allogeneic Bronchoalveolar Lavage Cells Induce the Histology and Immunology of Lung Allograft Rejection in Recipient Murine Lungs," *Transplantation 67*(6): 890-896, 1999.

Wilkes et al., "Allogeneic Bronchoalveolar Lavage Cells Induce the Histology of Acute Lung Allograft Rejection, and Deposition of IgG2a in Recipient Murine Lungs," *J. Immunol. 155*:2775-2783, 1995.

Wilkes et al., "Autoimmune Responses to Grafted Lungs: Immune Responses to a Native Collagen—type V Collagen," sagepub.com, vol. 6, issue 1, pp. 42-49, 2003.

Wilkes et al., "Instillation of allogeneic lung macrophages and dendritic cells cause differential effects on local IFN-$\gamma$ production, lymphocytic bronchitis, and vasculitis in recipient murine lungs," *Journal of Leukocyte Biology 64*:578-586, 1998.

Wilson et al., "Shared amino acid sequences between major histocompatibility complex class II glycoproteins, type XI collagen and *Proteus mirabilis* in rheumatoid arthritis," *Annals of the Rheumatic Diseases 54*:216-220, 1995.

Yagyu et al., "Comparison of Mononuclear Cell Subpopulations in Bronchalveolar Lavage Fluid in Acute Rejection After Lung Transplantation and *Mycoplasma* Infection in Rats," *J Heart Transplant 9*(5):516-525, 1990.

Yamagami et al., "Suppression of Allograft Rejection with Anti-$\alpha\beta$ T Cell Receptor Antibody in Rat Corneal Transplantation," *Transplantation 67*(4):600-604, 1999.

Yasufuku et al., "Prevention of bronxhiolitis obliterans in rat lung allografts by type V collagen-induced oral tolerance," *Transplantation 73*:500-505, 2002.

Yasafuku et al., "Oral Tolerance Induction by Type V Collagen Downregulates Lung Allograft Rejection," *Am. J. Respir. Cell Mol. Bio. 25*:26-34, 2001.

Yoshino et al., "Suppression of Antigen-Induced Arthritis in Lewis Rats by Oral Administration of Type II Collagen," *Arthritis & Rheumatism 38*(8):1092-1096, 1995.

Yousem et al., "Revision of the 1990 Working Formulation for the Classification of Pulmonary Allograft Rejection: Lung Rejection Study Group," *J Heart Lung Transplant 15*(1):1-15, 1996.

Zheng et al., "CTLA4 Signals Are Required to Optimally Induce Allograft Tolerance with Combined Donor-Specific Transfusion and Anti-CD154 Monoclonal Antibody Treatment," *J. Immunol. 162*:4983-4990, 1999.

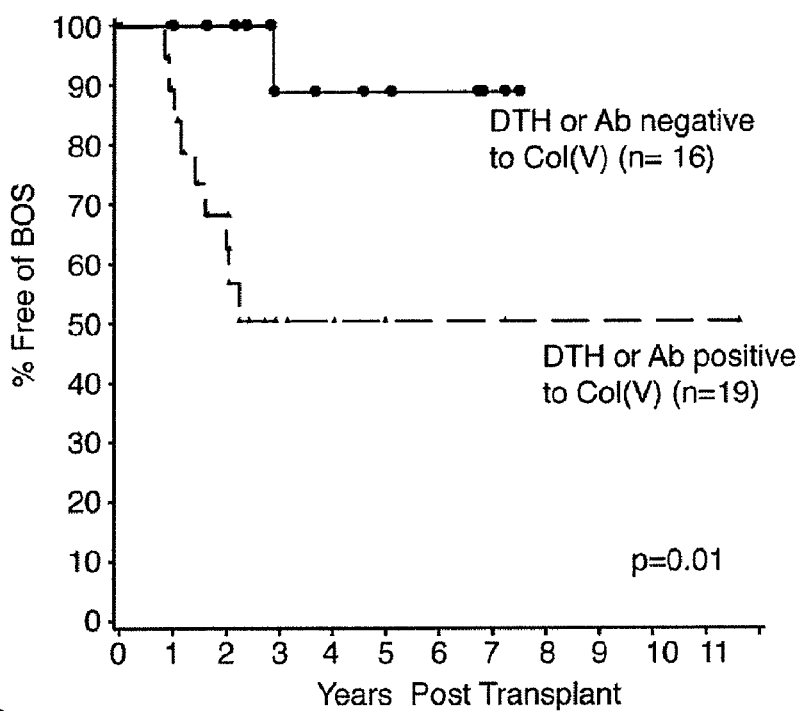
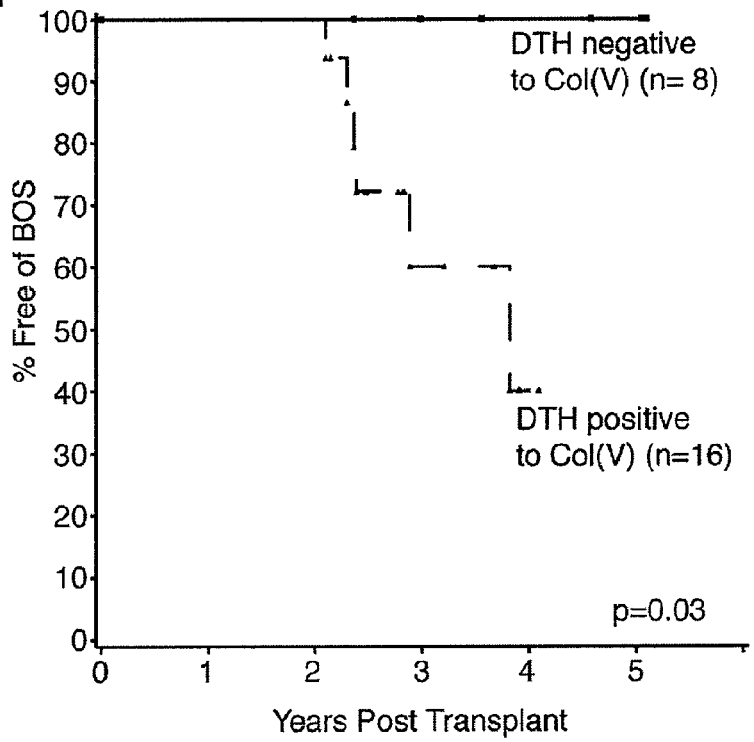
Fig. 2

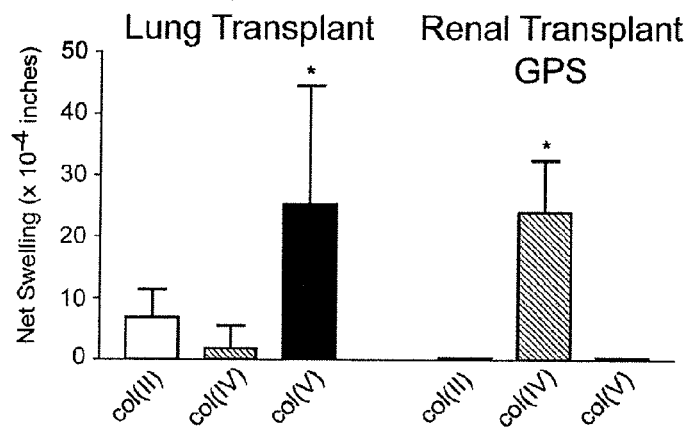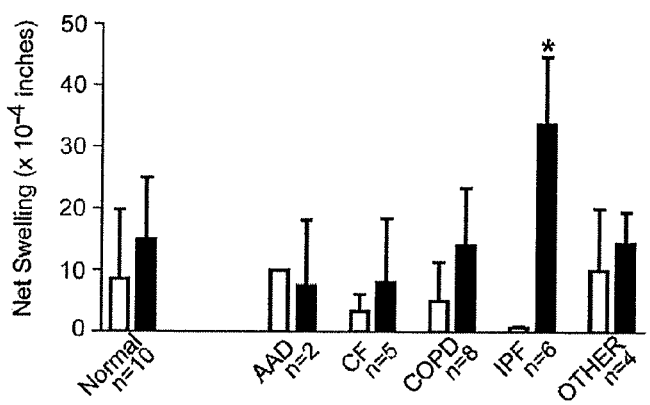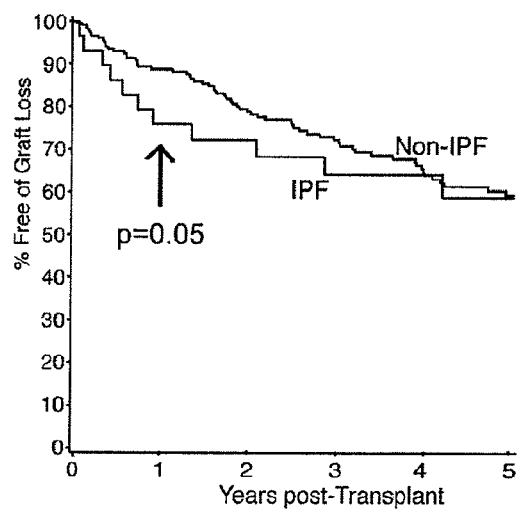
Fig. 3

|  | Study Groups | |
| --- | --- | --- |
|  | Total<br>n=226 | Col(V) Subset<br>n=56 |
| Bilateral Lung Transplants[a] | 93 (41%) | 30 (54%) |
| Pretransplant Diagnosis[a] | | |
| AAD | 36 (16%) | 10 (18%) |
| CF | 50 (22%) | 18 (32%) |
| COPD | 84 (37%) | 14 (25%) |
| IPF | 29 (13%) | 8 (14%) |
| OTHER[b] | 27 (12%) | 6 (11%) |
| Patients with BOS[a] | 86 (38%) | 18 (32%) |
| Mean Time to BOS[c] | 2.5 ± 1.9 | 2.2 ± 1.7 |
| Mean Follow-up[c] | 3.7 ± 2.7 | 3.8 ± 2.4 |

Table 1. Patient Demographics
[a]Number of patients (% of total)
[b]Other category includes patients with atrial septal defect, bronchiectasis, lymphangioleomyomatosis, idiopathic bronchiolitis obliterans, obliterative bronchiolitis, pulmonary fibrosis, primary pulmonary hypertension, and sarcoidosis
[c] Years ± standard deviation

Fig. 7

Table 2 Factors Associated with BOS

| Analysis of Col(V) Study Group | Risk Ratio | Confidence Intervals | p |
|---|---|---|---|
| Either DTH or Ab to col(V)[a] | ∞[b] | NA[b] | NA[b] |
| DTH to col(V) ≥ 25[c] | 12.3 | 1.6-97. | 0.02 |
| Ab to col(V) ≥ 1[e] | 2.08 | 1.1-4.0 | 0.02 |
| # of Rejection Episodes | 1.58 | 1.1-2.3 | 0.02 |
| Analysis of All Patients | | | |
| # of Rejection Episodes | 1.40 | 1.2-1.7 | < 0.001 |
| Original disease[e] = CF | 0.35 | 0.2-0.7 | 0.002 |
| Original disease[e] = COPD | 1.70 | 1.1-2.7 | 0.01 |
| Original disease[e] = OTHER | 1.90 | 1.1-3.4 | 0.02 |
| Bilateral Transplant | 0.59 | 0.4-0.9 | 0.02 |
| HLA Mis-Match DR | 1.62 | 1.0-2.6 | 0.03 |

[a] Time-varying covariate indicating whether the patient ever had a positive DTH or Ab response to col(V).

[b] Since there were no patients with BOS who did not also have a response to col(V), the best estimate of the risk ratio is infinity, there is no confidence interval, and the p value is undefined.

[c] Time-varying covariate indicating a positive (net swelling ≥ 25) DTH response.

[d] Time-varying covariate indicating a positive Ab response to col(V).

[e] Patient survival in each disease category was compared to survival of patients with all other diseases.

Fig. 8

TABLE 3

Grading of Rejection Pathology

| Group | A (acute rejection) | B (airway inflammation) |
|---|---|---|
| Control WKY isograft | 0 ± 0 | 0 ± 0 |
| Control WKY allograft | 3.8 ± 0.2 | 4.0 ± 0 |
| Col(II)-fed WKY allograft | 3.9 ± 0.3 | 4.0 ± 0 |
| Col(XI)-fed WKY allograft | 3.9 ± 0.1 | 4.0 ± 0 |
| Col(V)-fed WKY allograft | 2.8 ± 0.2* | 2.6 ± 0.2† |

Fig. 15

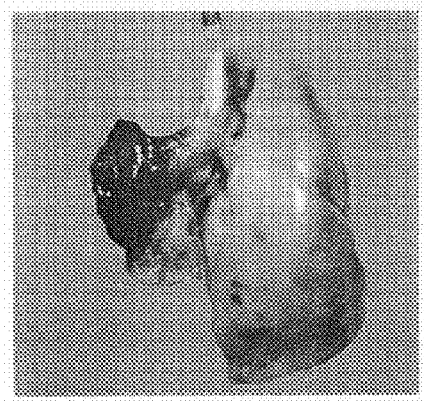
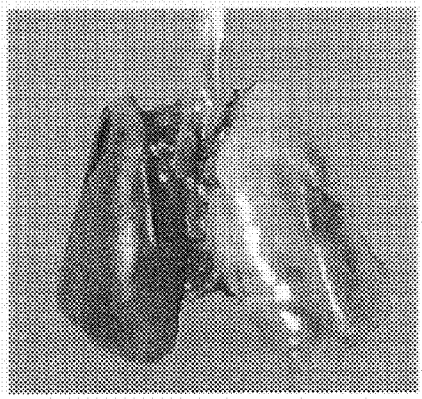
FIG. 21A  FIG. 21B
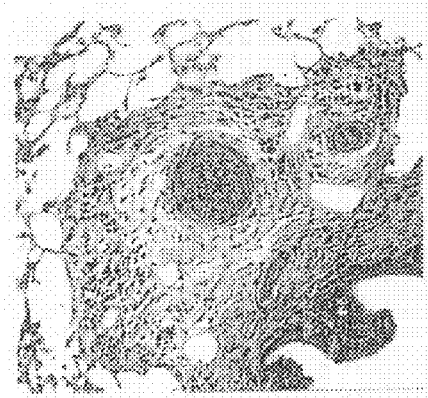
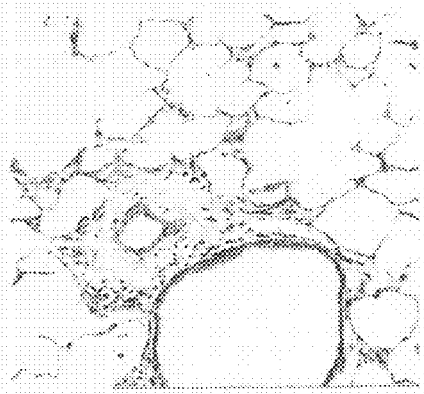
FIG. 21C  FIG. 21D

TABLE 4

Experimental Groups:

| Col (V)-fed Allograft (n = 20 for each dose and Allograft-schedule) | Control (n = 20) | Isograft (N = 20) |
|---|---|---|
| Donor: f344 rat lung (RTI $^{lvl}$) Recipient: WKY (RTI $^l$) rats - fed col(V) 10μg, 20μg or 50μg every other day for 4 or 8 days | Donor: f344 rat lung (RTI $^{lvl}$) Recipient: WKY (RTI $^l$) rats - no feeding | Donor: WKY (RTI $^l$) rat lung Recipien: WKY (RTI $^l$)rats |

Fig. 25

TABLE 5

The Determination of Whether Peptides Present in Cyanogen Bromide Digests of α-chains of Col(V) Prevent the Development of Acute Rejection
Experimental Groups

| Allograft Control (n = 10) | Intact Col(V)-fed (n = 20) | l(v)Fed(n =20) | 2(V)-fed 9N = 20) |
|---|---|---|---|
| Donor: F344 rat lung (RTI $^{lvl}$) Recipient: WKY (RTI $^l$) rats - unfed | Donor: F344 rat lung (RTI $^{lvl}$) Recipient: WKY (RTI $^l$) rats - fed intact col(V) | Donor: F344 rat lung (RTI $^{lvl}$) Recipient: WKY (RTI $^l$) rats - fed l(V) peptides | Donor: F344 rat lung (RTI $^{lvl}$) Recipient: WKY (RTI $^l$) rats - fed 2(V) peptides |

Fig. 26

METHOD TO IDENTIFY PATIENTS AT RISK FOR LUNG TRANSPLANT REJECTION

PRIORITY CLAIM

This application is a continuation of U.S. patent application Ser. No. 12/823,570, filed on Jun. 25, 2010; which application is a continuation of U.S. patent application Ser. No. 12/171,661, filed on Jul. 11, 2008, now U.S. Pat. No. 7,759,075, issued on Jul. 20, 2010; which application is a continuation of International Patent Application No. PCT/US2007/060533, filed on Jan. 13, 2007; which claims the benefit of U.S. Provisional Patent Application No. 60/759,195, filed on Jan. 13, 2006, each of which is incorporated herein, by reference, in its entirety.

STATEMENT OF GOVERNMENT FUNDING

This invention was made with government support under HL060797 awarded by National Institutes of Health. The U.S. Government has certain rights in the invention.

FIELD OF THE INVENTION

Various embodiments relate generally to tests and treatments for lung disease, some aspects include identifying evidence of an autoimmune response to lung connective tissue such as Type V collagen, still other aspects include modulating a patient's immune response to collagen by dosing a patient with a therapeutically effective amount of collagen and collagen like molecules to tolerize the patient to, for example, Type V collagen.

BACKGROUND

Pathologies that involve an autoimmune response are well known. Conditions that involve damage done to tissue by a given human or animal patient's own immune system include, for example, type 1 (juvenile) diabetes, rheumatoid arthritis, multiple sclerosis, and some inflammatory conditions including, for example, psoriasis. Typically a portion of the animal's own immune system mounts an attack on an antigen of the animal's own tissue. As exemplified by the aforementioned autoimmune diseases the results can be catastrophic, ranging from the creation of a chronic albeit manageable condition like diabetes, to complete disability and premature death as often occurs with multiple sclerosis.

In addition to various diseases specifically tied to an autoimmune response, other diseases may also involve an errant immune response. Accordingly, there is profound interest in examining the etiology of various diseases to determine what, if any, role the patient's own immune response may play in the progression of the disease.

Another pathology that includes an attack on indispensable tissue by a patent's own immune system is allograft rejection following organ or tissue transplantation. Transplantation of various organs including heart, kidney, liver and lung often results in the transplant recipients' immune system attacking the transplanted tissue. To minimize allograft rejection great care is taken to match organ donors and recipients. Still, perfect matches outside of those between identical twins are virtually impossible to make. In order to manage the ensuing alloimmune response, most transplant recipients are treated with immunosuppressive compounds for the duration of their lives in order to control the autoimmune response that might otherwise destroy the transplanted organ and or tissue.

Allograft rejection is especially problematic in pulmonary transplants between individuals that are less than perfect matches for one another. It is widely believed in the field of pulmonary transplants that rejection occurs more often with lung transplants than with the transplantation of most other solid organs. In fact, the leading cause of death in lung allograft recipients is chronic rejection, known as bronchiolitis obliterans (BO) (Trulock, 1997; Westra, et al., 1990). The pathogenesis of chronic rejection is poorly understood; however, the risk of developing chronic rejection is believed to correlate with repeated acute rejection episodes.

Bronchiolitis obliterans (BO) is a form of chronic rejection that is the major impediment to long term acceptance of the lung and survival of the allograft recipient, affecting at least 60% of 5-year post lung transplant survivors. The histopathology of BO suggests that inflammation and injury response leads to a final common pathway, the development of lesions associated with small airway obliteration. Ubiquitous donor HLA antigens are believed to be the target and stimulus of the acute rejection response. However, despite newer therapeutic agents that have reduced the incidence of acute rejection, the incidence of BO is unchanged, suggesting that drug-resistant host responses to tissue-specific antigens may be involved in the chronic rejection process.

Organ rejection, in many cases, is thought to be initiated by the recognition of allogeneic (donor) major histocompatibility complex (MHC) molecules by host T lymphocytes, leading to upregulated cellular and humoral immunity. Various treatments include administering Immunosuppressive agents to reduce the severity of the immune response to the transplanted organ. Unfortunately, in many cases these therapies fail to prevent continued rejection episodes, and therefore, the ultimate goal of inducing indefinite acceptance of the allograft, known as immunologic tolerance, remains elusive.

Allogeneic MHC molecules are the stimulus and target of the immune response during rejection. Therefore, MHC-derived peptides or synthetic peptides that may be homologous to MHC antigens have been the focus of investigations attempting to induce immunological tolerance to allografts (Krensky and Clayberger, 1997; Oluwole, et al., 1993). In addition, a very recent study reports the induction of tolerance to multiple allogeneic MHC molecules in vitro by a non-polymorphic synthetic peptide derived from MHC molecules (Murphy, et al., 1999). However, none of these reports appear to have resolved the issues of allograft rejection, and, in particular, lung allograft rejection.

Since recognition of polymorphic regions of donor MHC molecules is usually the stimulus for allo-immune responses, immunological tolerance induced by peptides derived from the donor MHC may be specific to the allele of the donor MHC molecules. Accordingly, identification of proteins/peptides that are highly conserved amongst individuals and that also induce immunologic tolerance across multiple MHC alleles may be of great importance in developing effective therapies to treat patients suffering from or at risk for developing allograft rejection. However, the use of such proteins/peptides for induction of immunological tolerance to lung allografts has not been fully evaluated. Further, very few proteins/peptides that are useful for such tolerance have been reported.

Furthermore, despite the existence of different techniques to induce tolerance to solid organ allografts, such as donor specific blood transfusion, thymic injection with donor-derived APC's, or systemic immunization with peptides derived from donor MHC molecules prior to transplantation (Krensky and Clayberger, 1997), for any of these techniques to be effective the specific donor MHC molecules must be known several weeks prior to transplantation to allow sufficient time, i.e., weeks to months, for tolerance induction to develop. However, in the typical scenario only a few hours exist between the identification of a potential donor and the transplantation surgery, in most cases then there is insufficient time to induce tolerance in most transplant recipients.

Transplant recipients who already suffer from an autoimmune disease, which may have itself necessitated the need for an organ transplant may be at heighten risk for catastrophic rejection of transplanted organs. Accordingly, there is a need to identify and perhaps treat any underlying autoimmune based pathology, if not before, certainly after a transplantation. There are also various lung diseases and disorders such as Idiopathic Pulmonary Fibrosis (IPF) which are difficult to diagnose and treat and whose underlying etiology is unknown, further complicating effort to diagnose and treat them.

Clearly then, there is a need for methods that can be used to identify autoimmune diseases such as IPF and to treat or at least manage such diseases. The need is especially acute in the case of diseases where one leading treatment, lung transplantation, may itself be severely compromised by an existing pathogenic autoimmune response. Various aspects and embodiments are directed to diagnosing and treating diseases that are caused by, or aggravated by, an undesirable autoimmune response to component of the lung such as various and specific types of collagen.

SUMMARY

One embodiment is a method of assessing pulmonary diseases or disorders such as IPF in a human or animal patient. One embodiment comprises the steps of obtaining a sample of fluid or tissue from a patient and analyzing the sample to determine if any component of the patient's immune system has mounted an immune response to any element of connective tissue found in an organ of the patient's body. Typical connective tissue components may include any type of collagen and/or antigenic components of collagen. Various collagens that may elicit an autoimmune response include, for example, Type I collagen, Type II collagen, Type III collagen, Type IV collagen, Type V collagen, and Type VI collagen. Tests to assess for pulmonary diseases or conditions in these patients may comprise the steps of obtaining a sample of fluid or tissue from a patent, contacting at least a portion of the sample with at least one antigenic component (epitope) of Type V collagen and monitoring the test for any signal indicative of the presences of at least one anti-Type V collagen antibody in the sample. Such tests may include the presence of any type of additional component as may be necessary or beneficial for conducting the tests. Such components include, but are not limited to, secondary antibodies that bind to anti-Type V antibodies, reporter molecules or atoms, surfaces for binding the antigenic component, buffers, stabilizers, antimicrobial agents and the like.

One aspect is an assay comprising the steps of: obtaining a sample of fluid or tissue from the lung or fluid that was in contact with the lung, contacting at least a portion of the sample with at least one epitope of Type V collagen or any other molecule that preferentially binds to anti-Type V collagen antibody, and detecting a change associated with the binding or anti-Type V antibody with at least one epitope of Type V collagen in the sample. This assays and variations thereof can be used to assay for pulmonary diseases such as IPF and the like or any other type of lung disease or disorder that includes an autoimmune response to at least one portion of Type V collagen.

Another embodiment is a method of determining if a patient has autoimmunity to a component of the lung. A typical autoimmune response may involve either or both humoral or cellular immunity. Such responses include, for example, delayed type hypersensitivity response. Pulmonary diseases that may have an autoimmune dimension include, but are not limited to, Idiopathic Pulmonary Fibrosis, Acute Respiratory Distress Syndrome, Adult Respiratory Distress Syndrome, secondary collagen vascular disease, other fibrotic lung diseases and the like.

One embodiment includes screening patients to identify specific patients or groups of patients that have an elevated risk for developing pulmonary diseases or conditions which have an autoimmune dimension. Such diseases or conditions include, but are not limited to, Idiopathic Pulmonary Fibrosis (IPF), Acute Respiratory Distress Syndrome, Adult Respiratory Distress Syndrome, secondary collagen vascular disease, other fibrotic lung diseases and the like, or other conditions that are due at least in part to an autoimmune reaction to lung connective tissue such as Type V collagen. Tests to screen these patients may comprise the steps of obtaining a sample of fluid or tissue from a patent, contacting at least a portion of the sample with at least one epitope of Type V collagen and monitoring the mixture of sample and antigen for any signal indicative of the presences of at least one type of anti-Type V collagen antibody in the sample.

Still another embodiment includes monitoring the progression of pulmonary disease in a patient or monitoring the efficacy of various treatment regimes used to treat a patent suffering from such a disease or disorder of the lung. Tests to monitor these patients may comprise the steps of obtaining a sample of fluid or tissue from a patent, contacting at least a portion of the sample with at least one epitope of Type V collagen and monitoring the test for any signal indicative of the presences of at least one anti-Type V collagen antibody in the sample.

One embodiment includes diagnostic tests for diseases such as IPF, in some embodiments the test may comprise the steps of obtaining a sample of fluid or tissue from the patient, contacting at least a portion of the sample with at least one epitope of Type V collagen and monitoring the mixture for any signal indicative of the presences of at least one anti-Type V collagen antibody in the sample.

Still another embodiment includes evaluating lung transplant candidates to identify candidates, which have an elevated risk for developing BOS e.g., patients that test positive for an autoimmune response to collagen found in the lung such as Type V collagen. Methods of evaluating these candidates may comprise the steps of obtaining a sample of fluid or tissue from the candidate, contacting at least a portion of the sample with at least one epitope of Type V collagen and monitoring the antigen and sample mixture for evidence that the anti-Type V antibody in the sample has bound to antigen. Tests to evaluate these candidates may comprise the steps of attaching the antigen to a solid surface, contacting the sample with the antigen, allowing time for the antigen to bind the antibody to the antigen present in the sample, and washing the bound antigen-antibody complex to remove excess antibody and/or sample. Additional steps may include attaching a reporter moiety to the antigen antibody complex and monitoring the system for any change in signal indicative of the presence of antibody bound to the antigen. In some embodiments the antigen in the test is at least one epitope of Type V collagen.

Another embodiment includes testing methods for identifying lung diseases that involve an autoimmune response to connective tissue in the lung such as Type V collagen. Some testing methods may comprise the steps of obtaining a sample of fluid or tissue from a given patient and assaying at least a portion of the sample for evidence of an autoimmune response to Type V collagen. In one embodiment the sample is analyzed for evidence of delayed hypersensitivity response to Type V collagen or an epitope or an antigenic analogue thereof. In still another embodiment the sample is analyzed for the presence of antibody to Type V collagen or an epitope or antigenic analogue thereof.

Still another embodiment is a method of identifying patients with a heightened risk of developing bronchiolitis obliterans syndrome (BOS) and/or monitoring the progression of the syndrome or efficacy of a therapy used to treat the syndrome. These methods generally include the steps of obtaining a sample of serum, blood, interstitial lung fluid, sputum, mucus or tissue from a patient and assaying the sample for evidence of an autoimmune reaction to a component of the connective tissue of the lung. In one embodiment the patient is a candidate for, or the recipient of, a lung transplant and the sample is assayed for evidence of a host immune response to Type V collagen. In one embodiment the sample is assayed for cellular immunity to Type V collagen. In still another embodiment the sample is assayed for humoral immunity to Type V collagen.

Another embodiment comprises assaying a sample of fluid or tissue for evidence of immunity to an epitope of Type V collagen, or an analogue, portion or component thereof.

Still another embodiment is a method of identifying prospective lung transplant receipts that are at heightened risk for rejecting the transplanted tissue due to an autoimmune response to Type V collagen or antigenic portions or fragments thereof.

Yet another embodiment is a method of monitoring lung tissue transplant receipts to assess their continued risk for rejecting the transplanted tissue due to an autoimmune response to Type V collagen or epitopes or antigenic fragments thereof.

Still another embodiment is a method for treating a patient with a disease or disorder or a patient at risk of developing a disease or disorder that involves an autoimmune response to connective tissue, such a Type V collagen found in the patient's organs. In one embodiment the method comprises the steps of providing immunosuppressive compounds, or compounds that tolerize the patient to the presence of the antigen such as Type V collagen and administering a therapeutically effective amount of the compound to a given patient. Such compounds include, but are not limited to, various collagens or portions of collagen, for example, Type V collagen or epitopes or antigenic analogues thereof. Typical connective tissue components that may induce an autoimmune response include, but are not limited to, any type of collagen and/or antigenic components (epitopes) of collagen. Various collagens that may elicit an autoimmune response include Type I collagen, Type II collagen, Type III collagen, Type IV collagen, Type V collagen, Type VI collagen and various antigenic components thereof.

Yet another embodiment is a method of treating or preventing the progression of pulmonary diseases or disorders such as Idiopathic Pulmonary Fibrosis, Adult Respiratory Distress Syndrome and other fibrotic lung disorders, Acute Respiratory Distress Syndrome, bronchiolitis obliterans syndrome (BOS), and the like, by providing collagen or an antigenic component of collagen to suppress the patient's autoimmune response to collagen or antigenic components of collagen in a patient's lung tissue or in the tissue of a transplanted lung. Such therapy may include administering a safe and effective dose of collagen or a component of collagen or an analogue thereof to a patient over a period of time determined to condition the patent's immune system to better tolerate collagen and to at least partially suppress the patient's autoimmune response to collagen. In one embodiment the collagen in Type V collagen or an antigenic fragment or analogue thereof.

Still another embodiment comprises treating a form of lung disease caused by or aggravated by an autoimmune response, which may include T-cell activity and delayed type hypersensitivity response to collagen or an antigenic portion of a collagen. In one embodiment collagen administered to the patient is selected from the group consisting of Type I collagen, Type II collagen, Type III collagen, Type IV collagen, Type V collagen, Type VI collagen and various antigenic components thereof. These compounds may be administering by a variety of means including, but not limited to, intrapulmonary instillation, orally, inhalation, subcutaneous injection, drip, direct injection, or the like.

Still another embodiment is a method of identifying patients with an increased risk of rejecting transplanted organs and tissues. Typically this method comprises the steps of collecting a sample of blood, sera, fluid, sputum or tissue from a patient and analyzing the sample to determine if any component of the patient's immune system has mounted an immune response to any element of connective tissue in an organ of the patient's body. Typical organs include, but are not limited to, lung, heart, liver, kidney, pancreas, and components of the eye. Typical connective tissue components may include any type of collagen and/or antigenic components of collagen. Various collagens that may elicit an autoimmune response include Type I collagen, Type II collagen, Type III collagen, Type IV collagen, Type V collagen, and Type VI collagen.

Still another embodiment is a kit for carrying out tests to determine if a given patient is at risk for developing an autoimmune based pulmonary pathology, or monitoring the health of a patient already diagnosed with such a condition. In one embodiment the kit includes at least one antigenic component of collagen, for example, Type V collagen or an epitope, fragment or analogue thereof suitable for detecting evidence of a cellular and or humoral autoimmunity to collagen. In one embodiment the kit further includes at least one reporter moiety either an atom or a molecule which exhibits a change in signal in the presence of at least molecule indicative of an autoimmune response to Type V collagen. In still another embodiment the kit further includes at least one buffer, stabilizer, preservative, antibacterial compound, adjuvant or the like which serves to increase the half-life, sensitivity, and/or reliability of the test. In one embodiment a kit further includes Fruend's adjuvant or components or analogues thereof.

BRIEF DESCRIPTION OF THE FIGURES

The above-mentioned aspects of the present invention and the manner of obtaining them will become more apparent and the invention itself will be better understood by reference to the following description of the embodiments of the invention, taken in conjunction with the accompanying figures, wherein.

Figure 1:
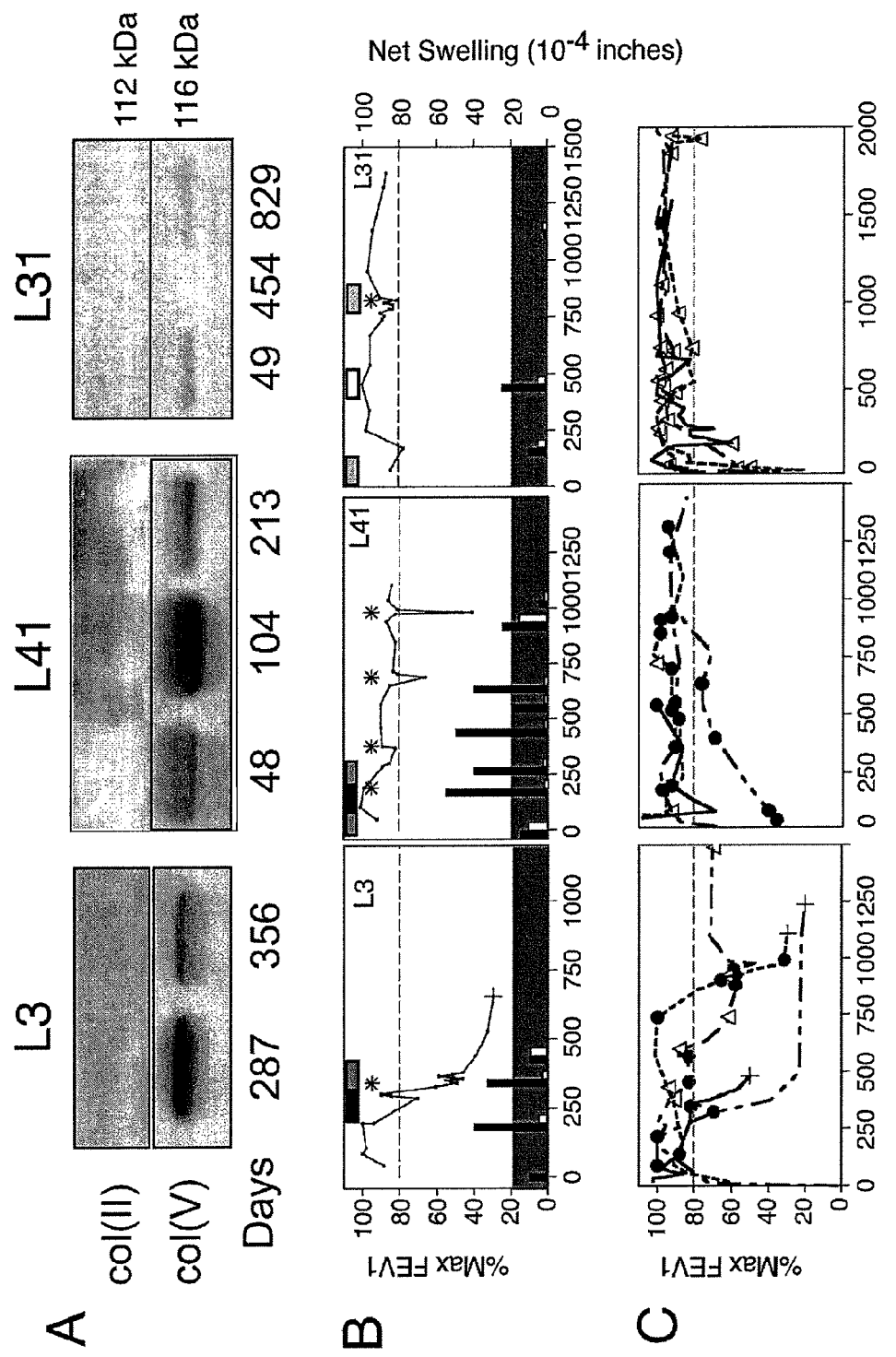
FIG. 1. Anti-col(V) B and T cell auto-reactivity in relation to clinical course of lung transplant recipients.

Panel A. Western blot analysis of IgG purified from BAL samples from patients L3, L41, L31 tested against col(II) or col(V).

Panel B. Time course of anti-col(V) autoimmunity and graft function in the same 3 patients. FEV1 (solid line, left axis) was adjusted to 100% of max (2.3 for L3, 2.4 for L41, and 2.8 for L31) for each patient. BOS level 1 is represented by grey dashed line (80% of max FEV1). DTH to col(V) (filled bars, right axis) and col(II) (open bars) are shown with negative DTH response ($<25\times10^{-4}$ inches) represented by the shaded area. Western blot results (from panel A) are represented by rectangles near the top of the graphs. Acute rejection episodes are represented by *.

Panel C. Composite of clinical course and anti-col(V) reactivity in 4 additional subjects with patterns of reactivity similar to that seen in panel B. The % Max FEV1 (each line represents data collected from an individual transplant recipient), positive Ab and/or DTH to col(V) (filled circles on the given subjects FEV1 line) or negative Ab and/or DTH to col(V) (open triangles on the FEV1 lines) as well as subject death (+) are shown. BOS 1 threshold (80% max FEV1) is represented by the grey dashed line.

FIG. 2. Plots of Kaplan-Meier analysis examining effect of developing anti-col(V) reactivity on freedom from BOS I. Patients with good graft function through day 326 post transplant (panel A) or day 760 post transplant (panel B) were divided based on their response to col(V) prior to that time. In panel A, those with a positive anti-col(V) response (dashed line) include either antibody/BAL or DTH/peripheral blood-positive; in panel B, DTH response is the only criteria used to identify patients with a prior positive anti-col(V) response. In both panels, patients with a negative prior anti-col(V) response are indicated by solid line. The difference between the col(V) non-reactive group and the col(V) reactive group was significant ($p=0.01$, panel A; $p=0.03$, panel B).

FIG. 3. DTH response to col(V) in post transplant lung patients is specific and not present pre-transplant.

Panel A. Data from post transplant lung patients (n=8, any disease) or renal patients with Goodpasture's syndrome (GPS, n=5) were tested for DTH response to col(II) (open bars), col(IV) (stippled bars), or col(V) (filled bars) expressed as mean swelling ±S.D. The difference between the responses of lung transplant recipients to the various collagens was significant (*, $p=0.001$) as was the difference between the responses of renal transplant recipients with GPS.

Panel B. Plot of data from non-transplanted patients with various lung diseases were tested for DTH response to col(II) (open bars) or col(V) (filled bars) expressed as mean swelling ±S.D. The difference between the response to col(V) in patients with IPF and any other disease was significant (*, $p=0.02$).

Panel C. Plot of Kaplan-Meier analysis of time to graft loss for patients with pre-transplant diagnosis of IPF or any other disease. The 1 year graft survival difference was significant ($p=0.05$). Overall graft survival by log rank analysis was not significantly different between groups.

Figure 4:
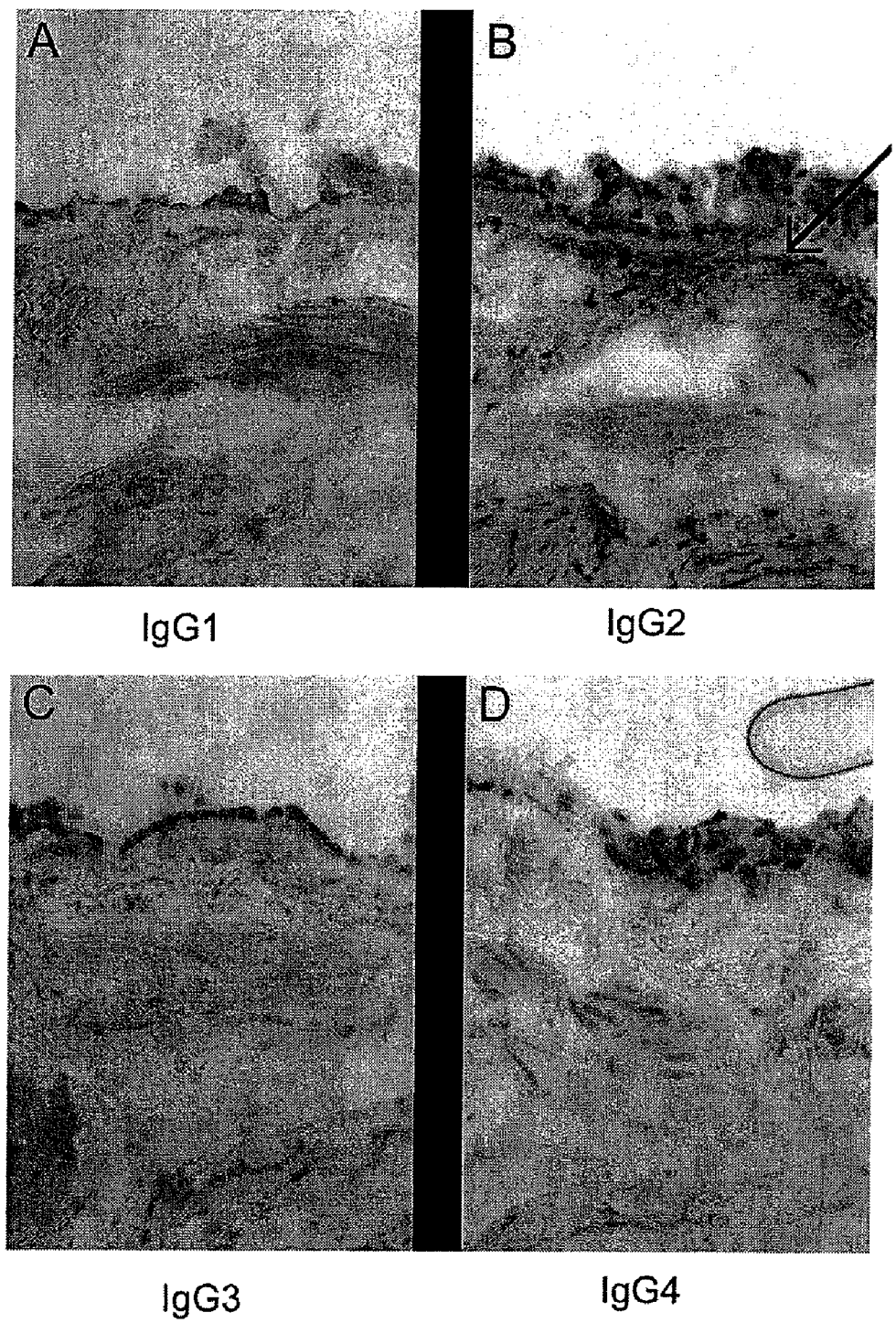

FIG. 4. Photomicrograph, of Immunochemistry of IgG, showing deposits in a lung having undergone Acute Rejection. Cryosections of transbronchial biopsy (TBB) or normal lung tissue were fixed in acetone and stained for IgG subtype deposits as described previously (Wilkes, et al, Journal of Immunology 1995). Panels A, B, C, and D show IgG1, IgG2, IgG3 and IgG4 subclass immuno-staining of TBB obtained from a lung allograft undergoing acute rejection grade 2 at day 100 post transplant. Note the IgG2 deposits in the peri-bronchiolar connective tissues underlying the bronchial epithelium (arrow). In contract, there were no IgG1, IgG3 or IgG4 deposits detected in the same sample. IgG2 deposits in the sub-epithelial matrix were absent in normal lungs and in allografts with a quiescent graft status (data not shown).

Figure 5:
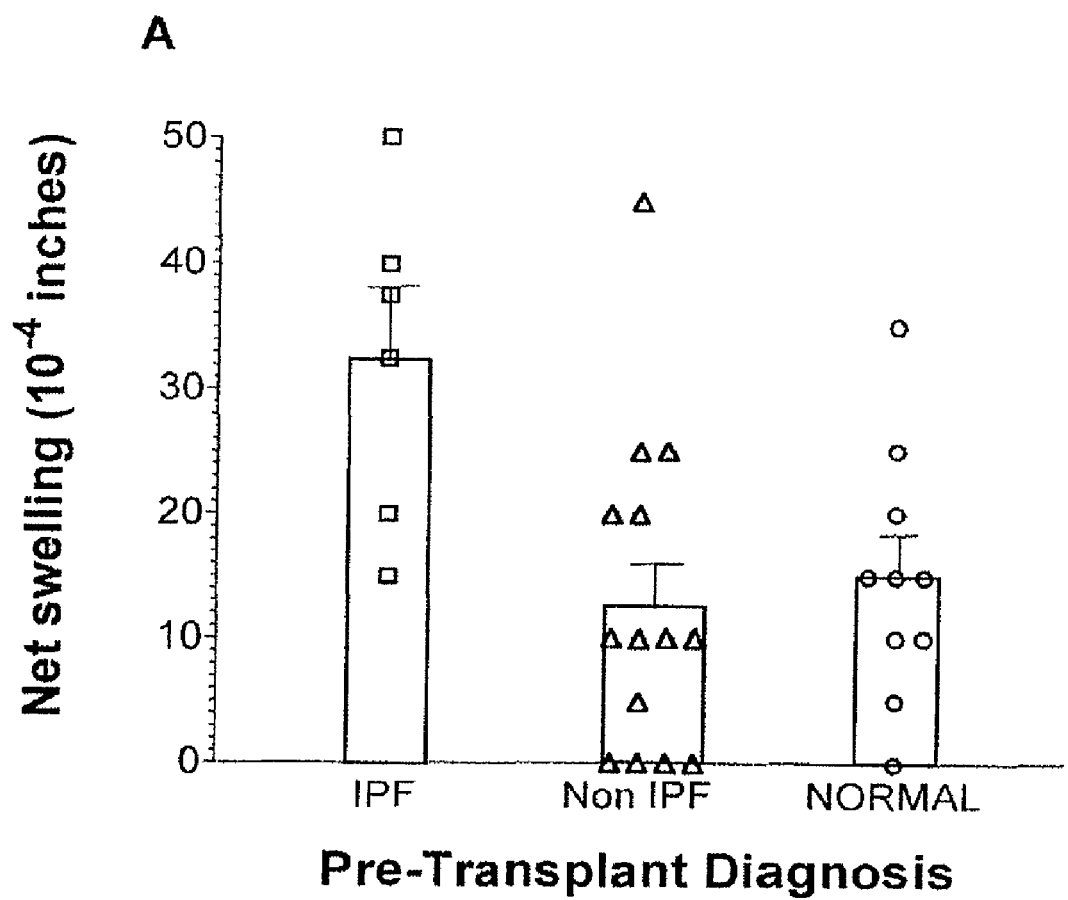

FIG. 5. Plot showing delayed type hypersensitivity (DTH) response to Type V Collagen in patients awaiting lung transplantation. The DTH response is a marker for T cell activation and reflects what we have reported in the rat lung transplant model. Patients with IPF but not other forms of lung disease have a significantly greater DTH response to Type V Collagen. This shows that these patients already have T cells activated against this self-antigen.

Figure 6:
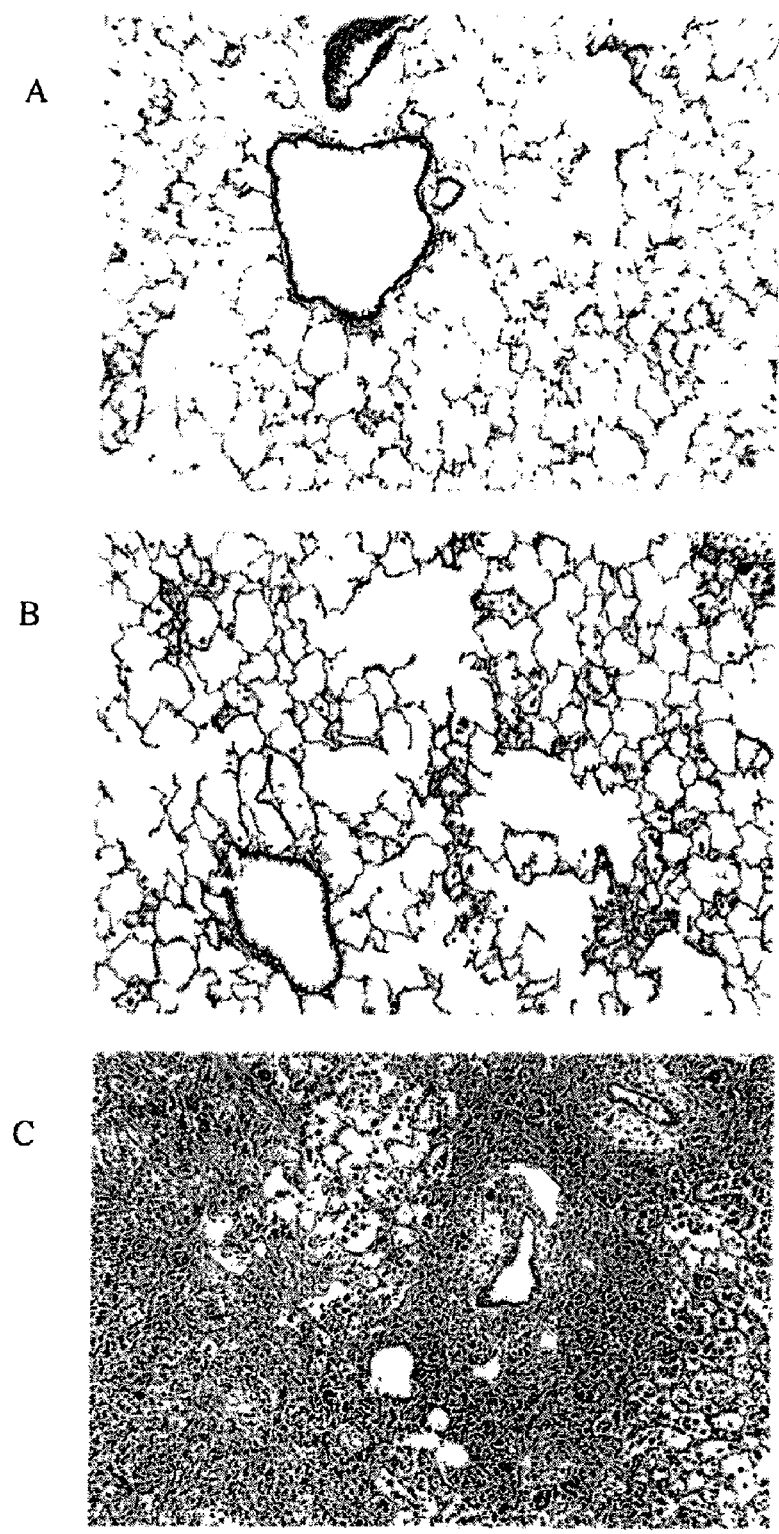
Figure 9A:
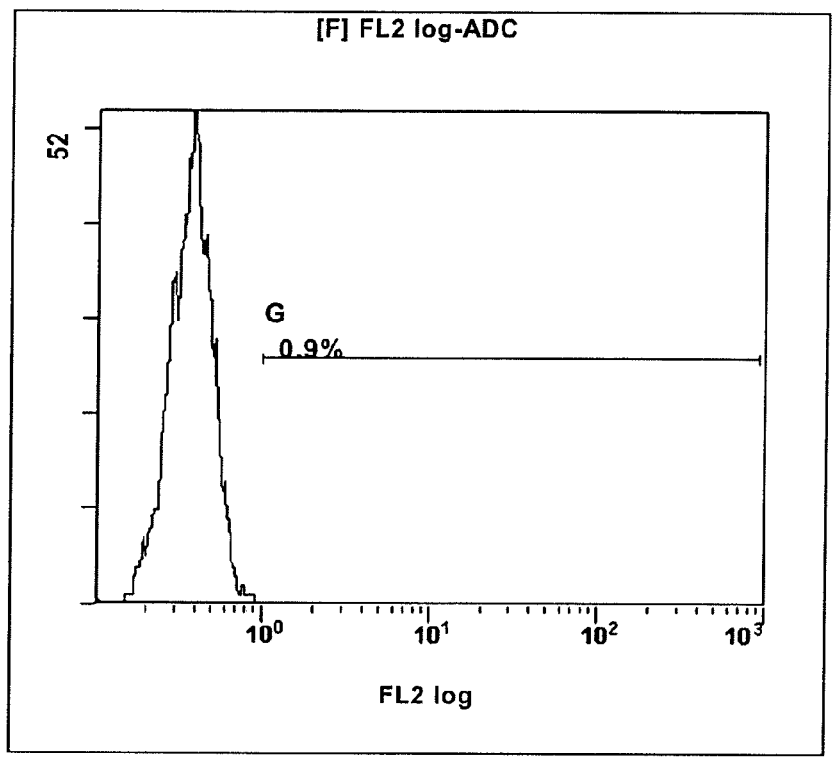
Figure 9B:
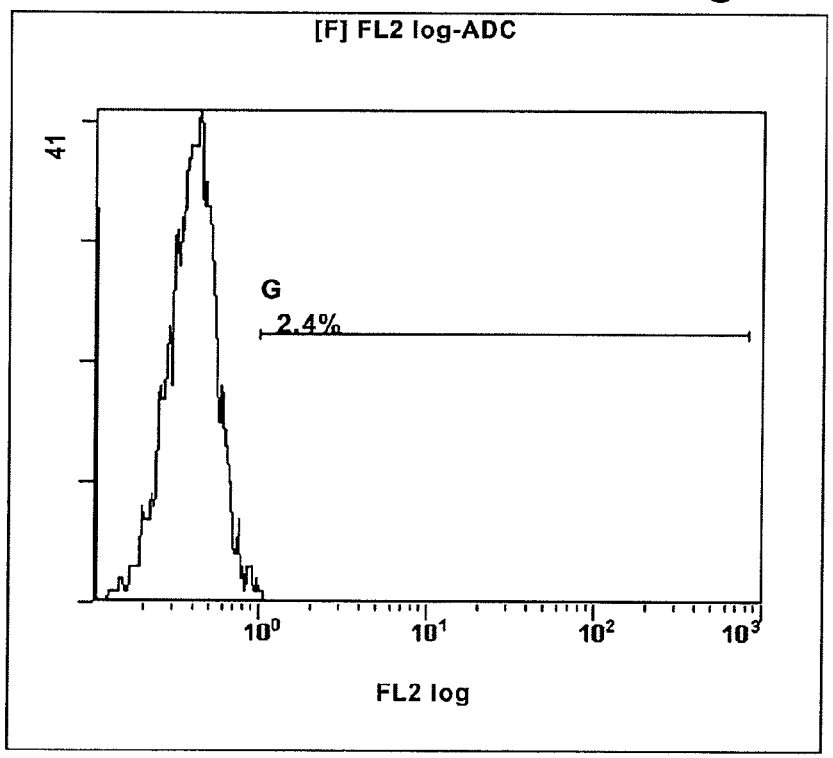
Figure 9C:
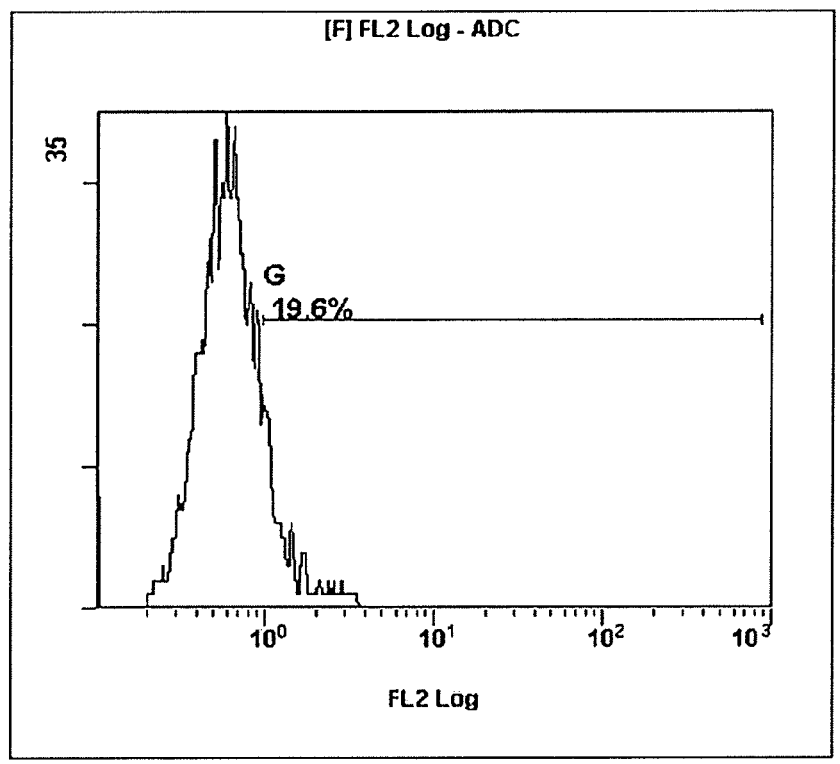
Figure 9D:
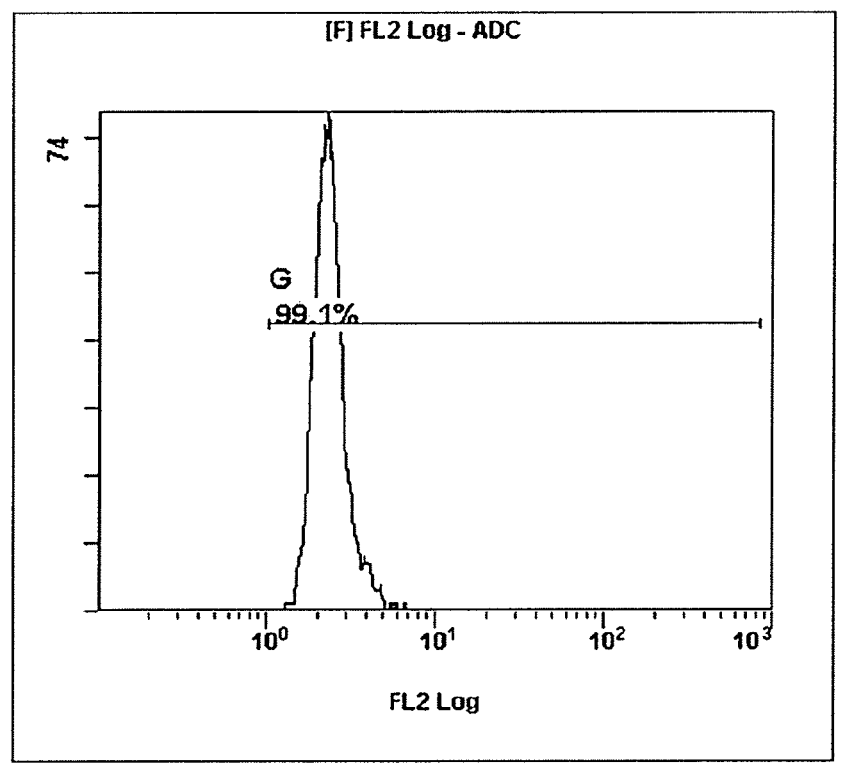
Figure 9E:
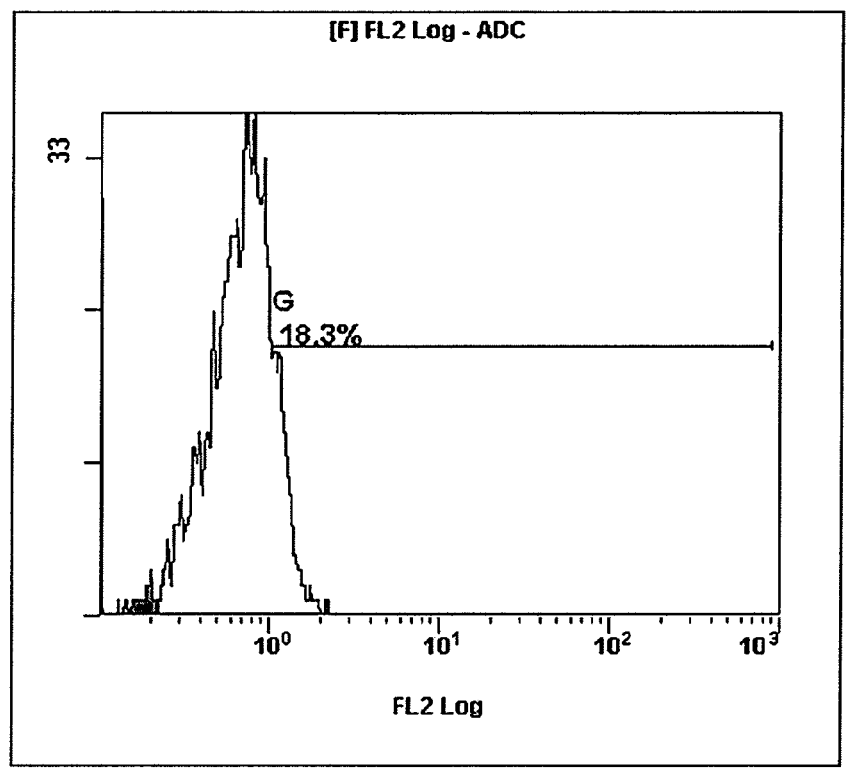
Figure 9F:
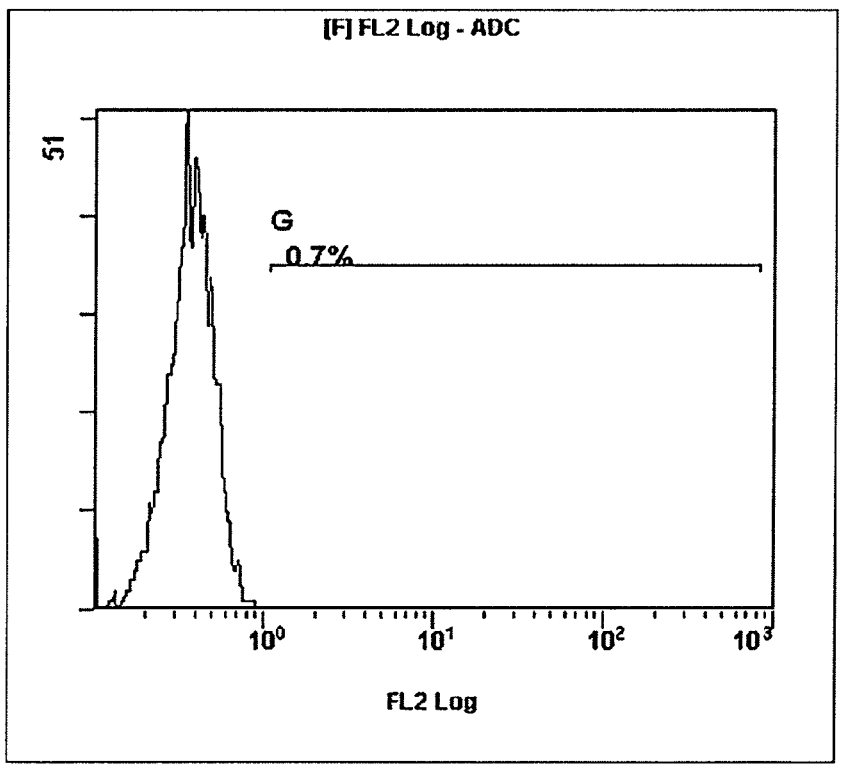
Figure 9G:
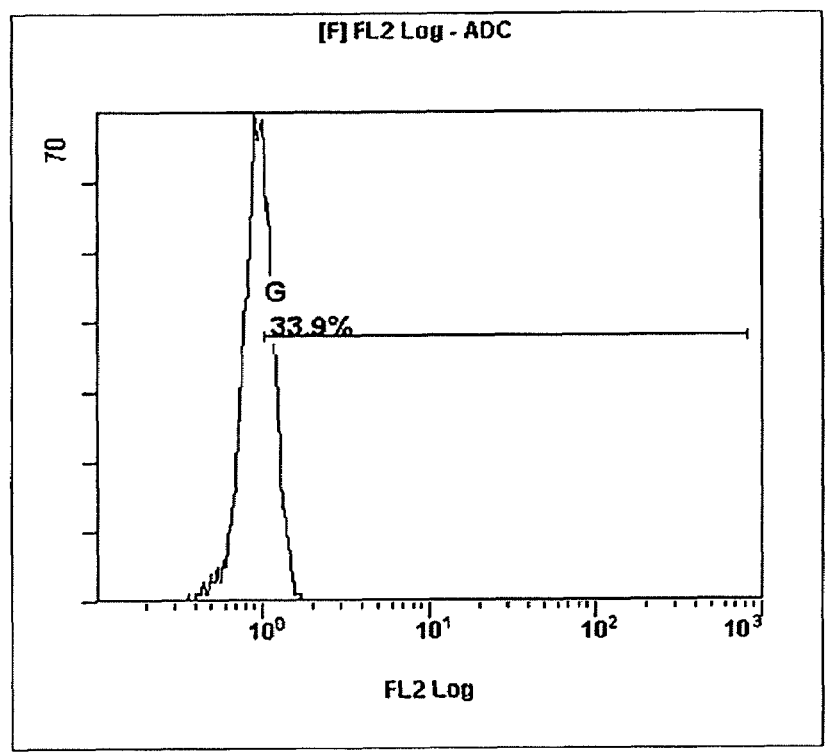
Figure 9H:
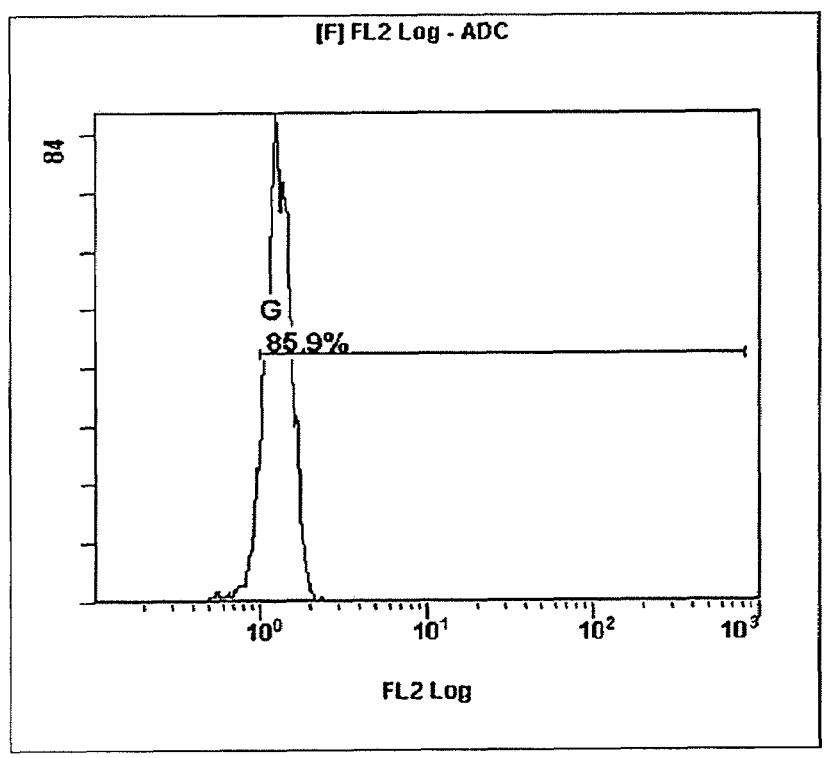
Figure 9I:
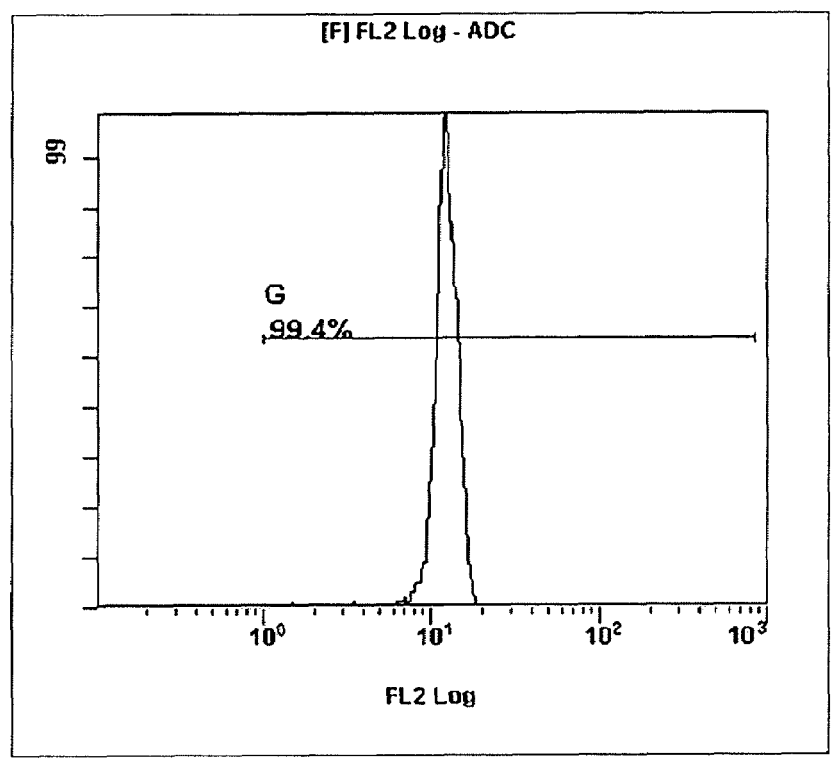
Figure 9J:
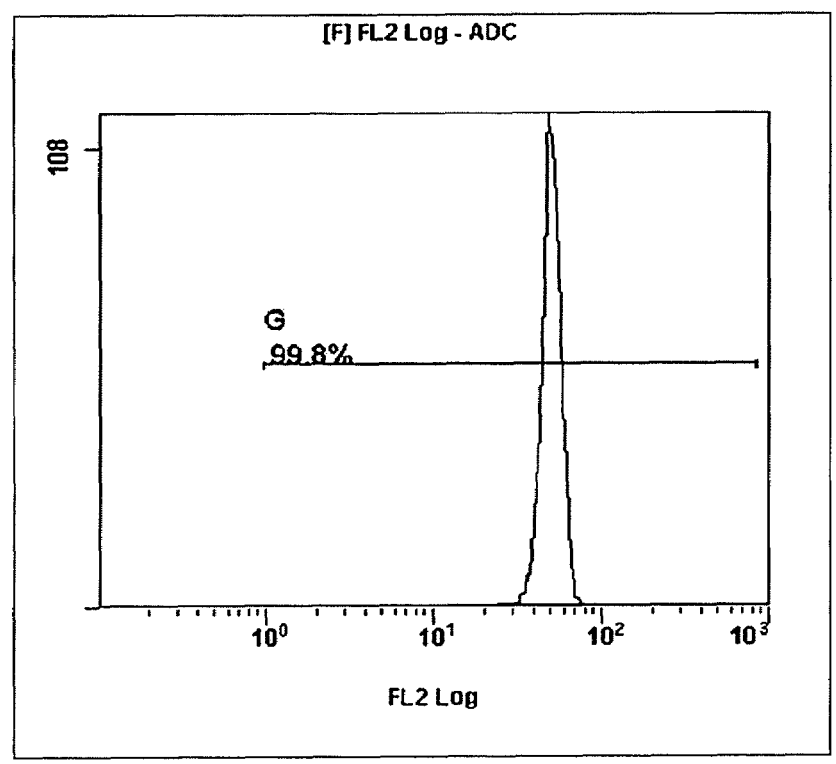
Figure 9K:
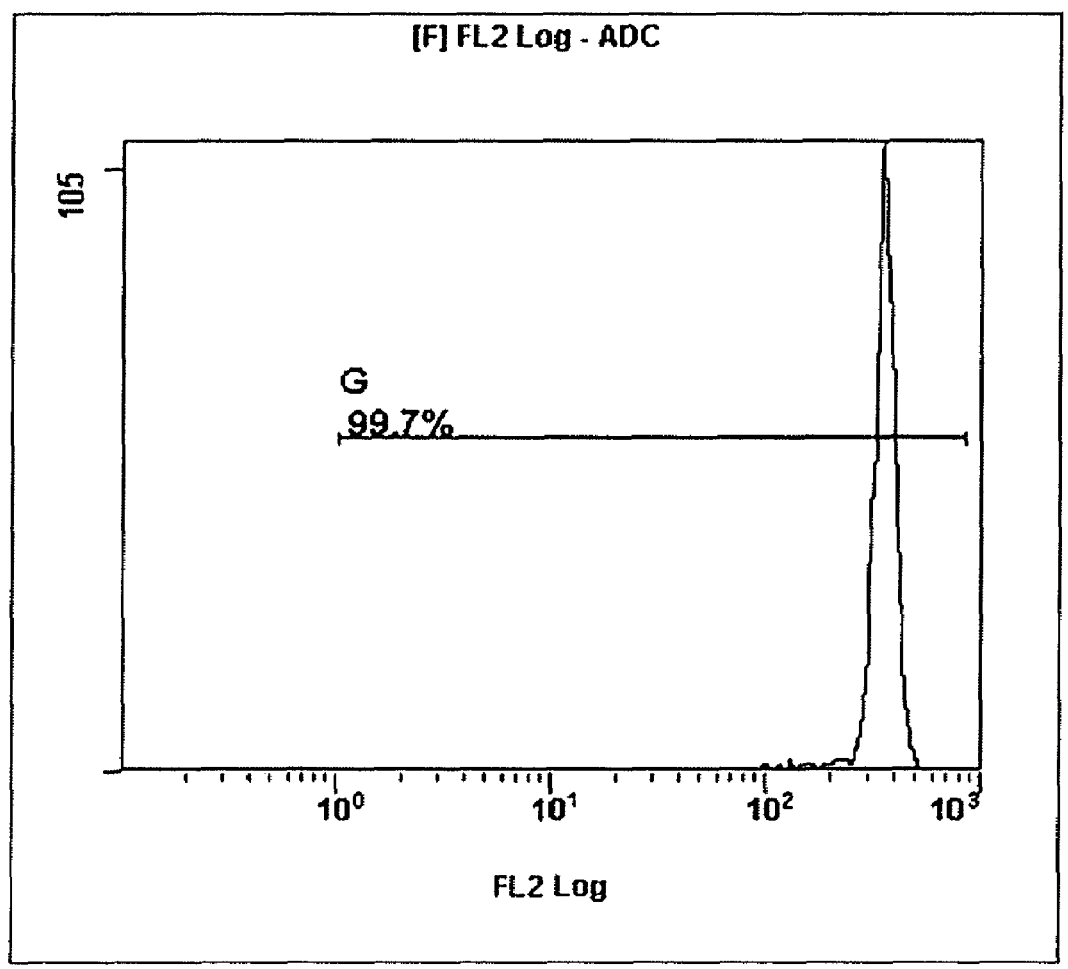

FIG. 6. Photomicrographs of stained lung tissue showing the effects of pathology of lung isografts transplanted into untreated WKY rat (A), a WKY rat previously immunized with Hen Egg Lysozyme (B), or a WKY rat previously immunized with Type V Collagen (C). The data shows that prior sensitization from col(V), but not HEL, results in destruction of the lung 30 days post-transplant. No rats received any immunosuppressive drugs or other treatments. The data is representative of 6 rats each for the HEL and col(V) groups and greater than SO rats in the untreated group.

FIG. 7. Table 1, summary of patient demographics. These conditions were diagnosed in patients having undergone lung transplantation procedures correlated with various post operative pathologies.

FIG. 8. Table 2 summary of data tracking various factors associated with BOS.

FIG. 9. Graphical illustration of data collected using an antibody bead based assay designed to detect different levels of anti-collagen V antibodies in sera samples. Peak shifts to right are indicative of high levels of anti-collagen V antibodies; Panels A, normal; B, #519; C, #420; D, #457; E, #458; illustrate data collected on samples taken from Patients Panels; F, negative control; G, $256_{pg}$; H, 1 ng, I, 32 ng, J, 160 ng, and K, 100 µg, illustrates data from various controls in which various levels of anti-collagen V antibodies were added to sera.

Figure 10:
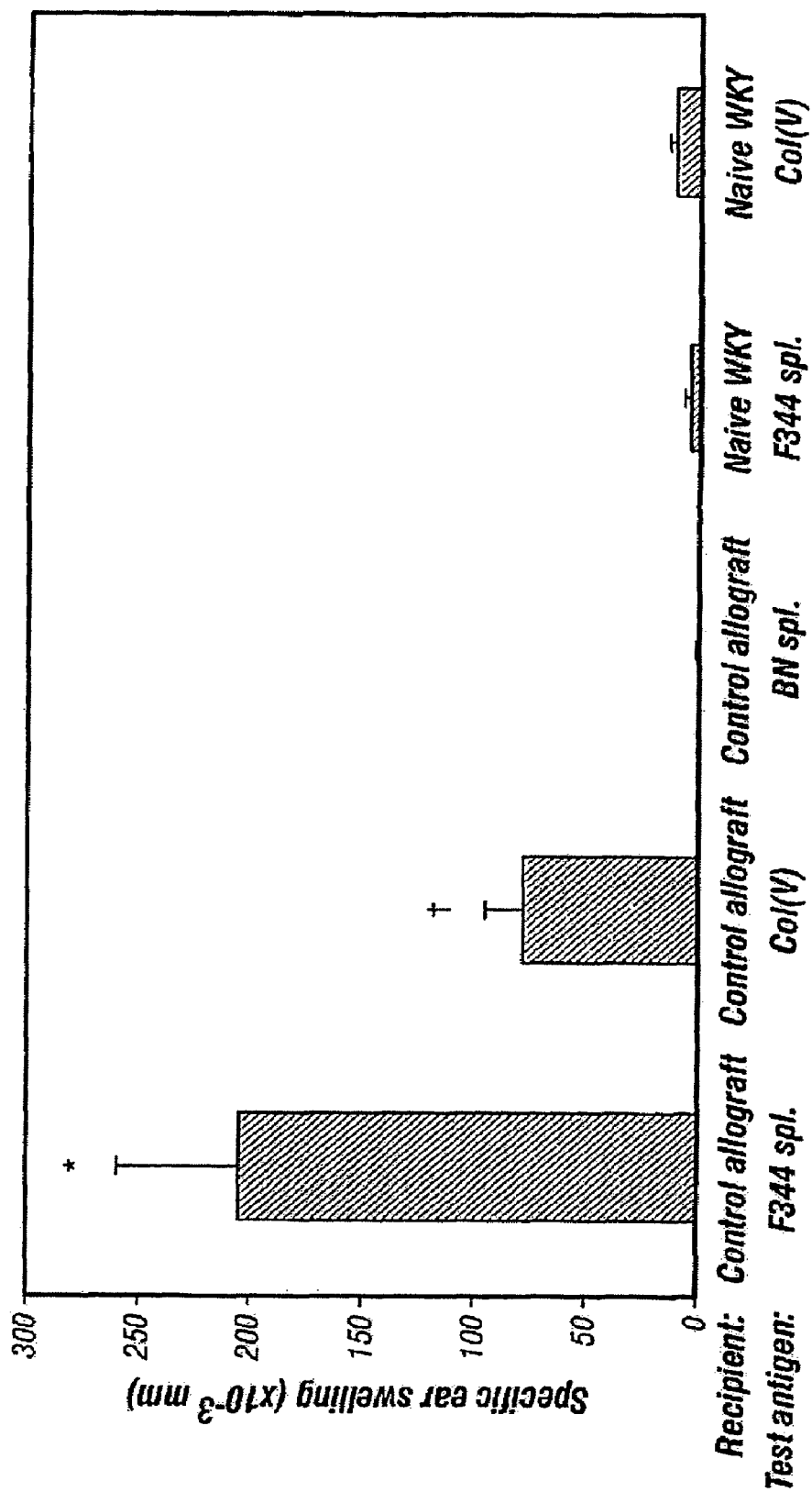

FIG. 10. Data illustrating reduction of DTH responses to donor alloantigens, col(V), and third party alloantigens in control allograft recipients two weeks post-transplantation. Naïve WKY rats were used as controls. Animals received $10^7$ irradiated (3000 rad) donor-derived F344 splenocytes, third party (BN) splenocytes, or 15 µg of col(V) into the right pinnae and diluent into the left pinnae. The ear thickness was measured with a micrometer caliper (Mitutoyo, Field tool Supply, Chicago, Ill.) in a blinded fashion immediately before and 24 hr after injection and the specific ear swelling calculated as described in Methods. Data represent the mean±SEM of specific ear swelling in mm×$10^{-3}$ of four rats in each group. [*$p<0.0001$ compared to nave WKY rats challenged with F344 splenocytes or col(V) and †$p<0.0001$ compared to naïve WKY rats challenged with col(V) or F344 splenocytes].

Figure 11B:
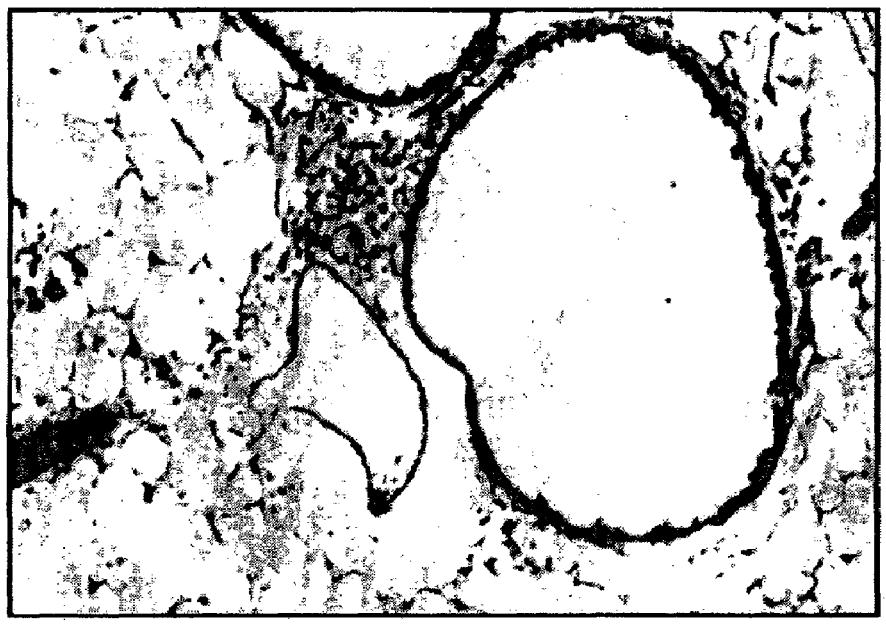
Figure 11A:
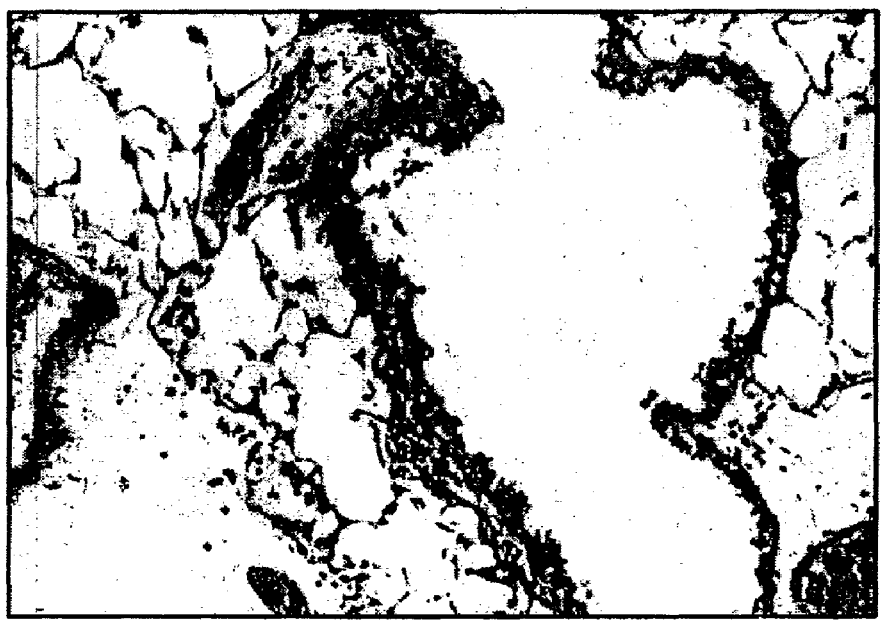

FIG. 11A, and FIG. 11B. Lung histology in BALB/c mice after four weekly instillations of $1.5\times10^5$ allogeneic (C57BL/6) BAL cells alone, col(II), or col(XI) (50 µg each) weekly for four weeks followed by four weekly instillations of C57BL/6 BAL cells. FIG. 11A shows peribronchiolar and perivascular mononuclear cell infiltrates in lungs of BALB/c mice that received instillations of BAL cells from C57BL/6 mice. Similar pathologic lesions were observed in lungs of BALB/c mice that received weekly instillations of col(II) (FIG. 11B) or col(XI).

Figure 12:
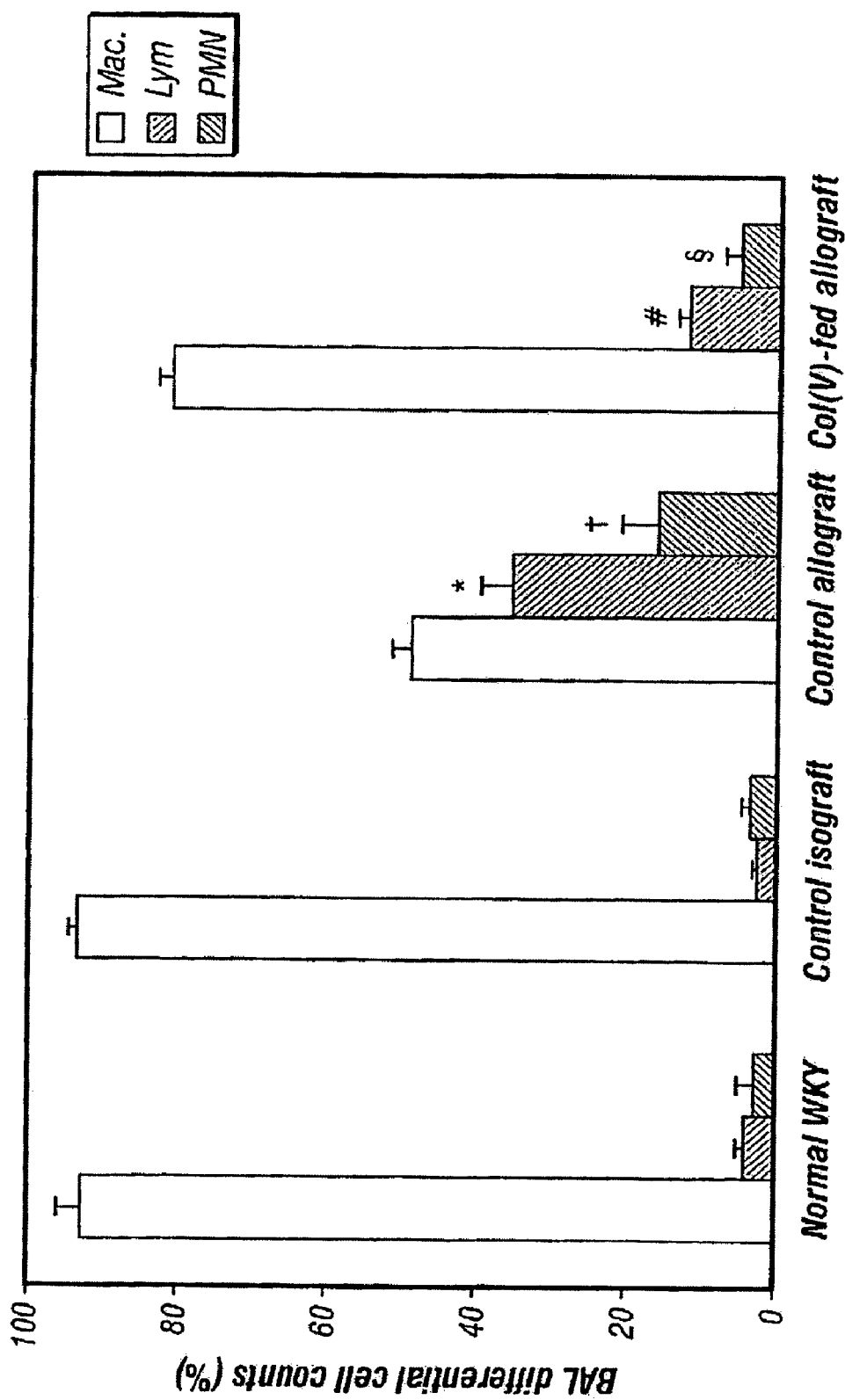

FIG. 12. Graph showing BAL fluid differential cell counts in normal WKY lungs, control isograft lungs, control allograft lungs, and col(V)-fed allograft lungs. At two weeks post-transplantation, transplanted lungs underwent BAL. Differential cell counts were determined by counting 300 cells/field on cytospin preparations utilizing light microscopy. Mac, macrophages; Lym, lymphocytes; PMN, polymorphonuclear cells. Data represent the mean±SEM of four normal WKY lungs, four control isografts, five control allografts, and five col(V)-fed allografts. (*$p<0.038$ for PMN's and †$p<0.000001$ for lymphocytes compared to normal or isograft lungs, #p<0.023 for PMN's and §p<0.0001 for lymphocytes compared to control allografts).

Figure 13A:
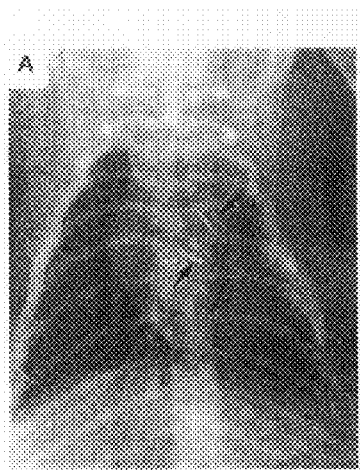
Figure 13B:
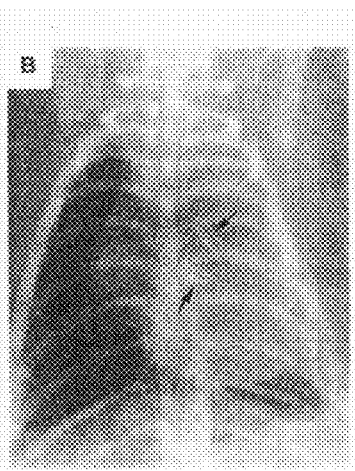
Figure 13C:
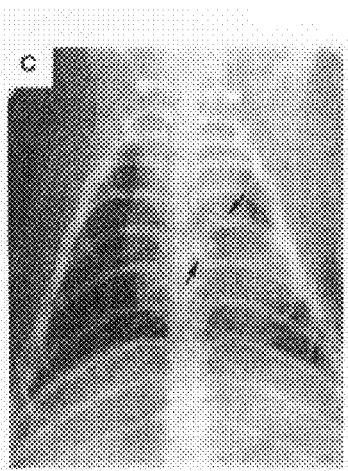

FIG. 13A, FIG. 13B, and FIG. 13C. Serial chest x-rays of transplant recipients two weeks post-transplantation. The short-white lines in the left lung field (arrowheads) represent the cuffs used for vascular anastomoses. Control isograft recipients show normal chest x-rays in FIG. 13A. X-rays of control allograft recipients revealed severe infiltrates and complete opacification of the allograft indicative of severe rejection in FIG. 13B. Col(V)-fed allograft recipients show only mild infiltrates at two weeks post-transplantation in FIG. 13C Chest x-rays representative of five rats in each group.

Figure 14C:
Figure 14F:
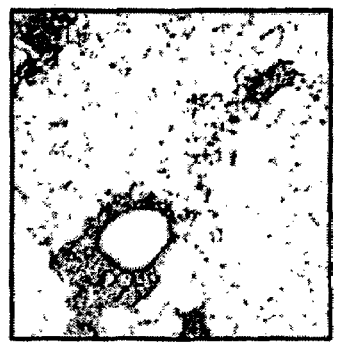
Figure 14B:
Figure 14E:
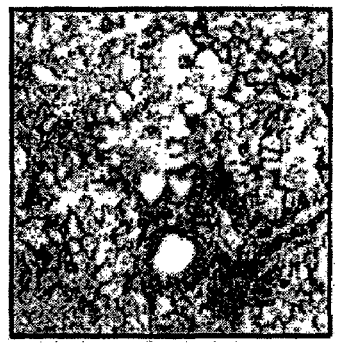
Figure 14A:
Figure 14D:

FIG. 14A, FIG. 14B, FIG. 14C, FIG. 14D, FIG. 14E, and FIG. 14F. Upper panel: Gross anatomy of control isograft lungs FIG. 14A, control allograft lungs FIG. 14B, and col(V)-fed allograft lungs FIG. 14C two weeks post-transplantation (posterior view). The left (L) lung is the transplanted lung and the right (R) is the native lung in each panel. The control allograft lung ("L" in panel b) was dark brown in color, shrunken, and of firm consistency compared to the native lung. However, the col(V)-fed allograft lung ("L" in panel c) had the appearance of the isograft lung ("L" in panel a). Control isograft lungs (FIG. 14A) show no pathologic lesions and are identical to normal WKY lungs. Photographs representative of five rats in each group. Lower panel: Histology of control isografts FIG. 14D, control allografts FIG. 14E, and col(V)-fed allografts FIG. 14F two weeks post-transplantation. Control isografts show normal airway and vascular structures (FIG. 14D). Control allografts show extensive perivascular, peribronchial, and alveolar mononuclear cell infiltrates consistent with severe rejection (FIG. 14E). In contrast, col(V)-fed allografts show only mild to moderate perivascular and peribronchial mononuclear cell infiltrates (FIG. 14F). Photomicrographs representative of five rats in each group (100× magnification).

FIG. 15. Table 3, reported grading of rejection pathology the table includes data from controls and from animal models for transplant rejection.

Figure 16:
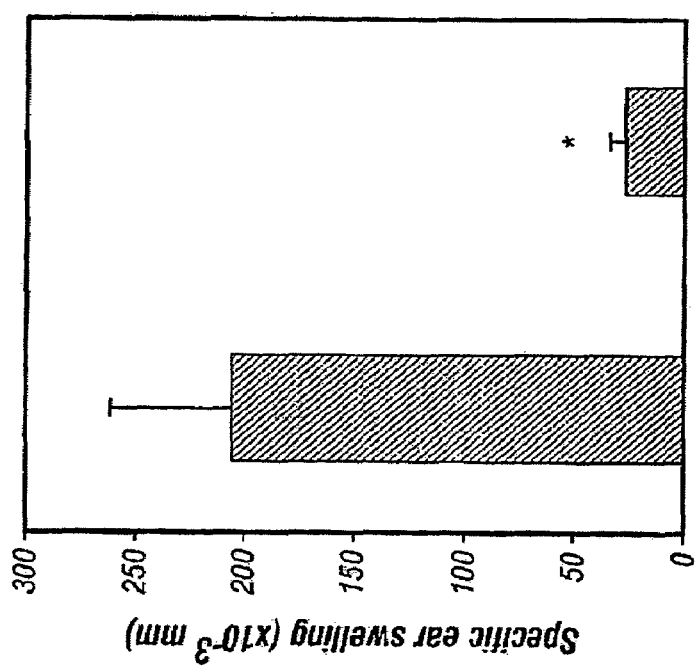

FIG. 16. Graph of data illustrating reduction of DTH responses to donor alloantigens by oral administration of col(V). Control allograft recipients and col(V)-fed allograft recipients two weeks post-transplantation were challenged in the right pinnae with $10^7$ irradiated (3000 rad) donor-derived F344 splenocytes, and diluent in the left pinnae. The ear thickness was measured with a micrometer caliper (Mitutoyo, Field tool Supply, Chicago, Ill.) in a blinded fashion immediately before and 24 hr after injection and the specific ear swelling. Data represent the mean±SEM of specific ear swelling in mm×$10^{-3}$ of four rats in each group. (*p<0.02 compared to control allografts).

Figure 17:
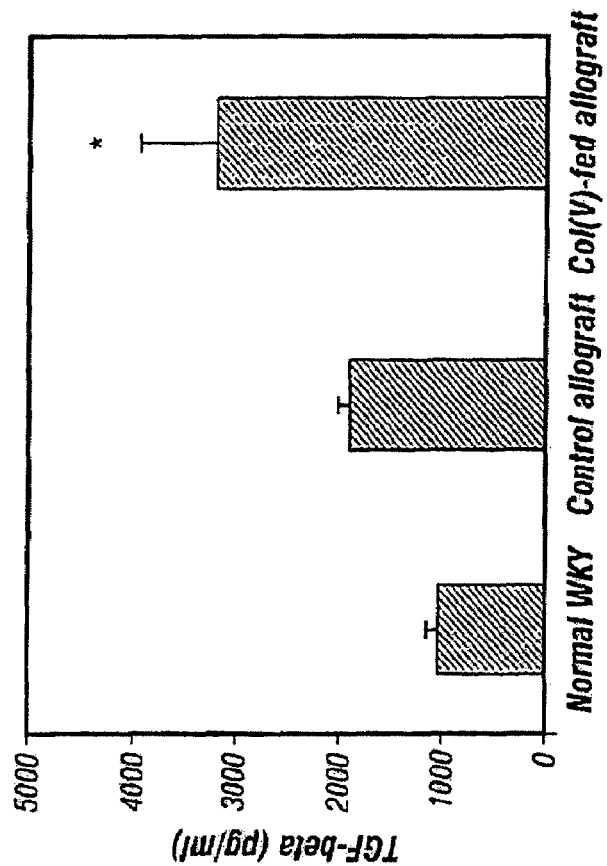

FIG. 17. Graph of TGF-β levels in serum of normal WKY rats, control allograft recipients, and col(V)-fed allograft recipients. Levels of TFG-β in serum were determined by ELISA. Data represent mean±SEM of four rats in each group. (*p<0.05 compared to control allografts).

Figure 18:
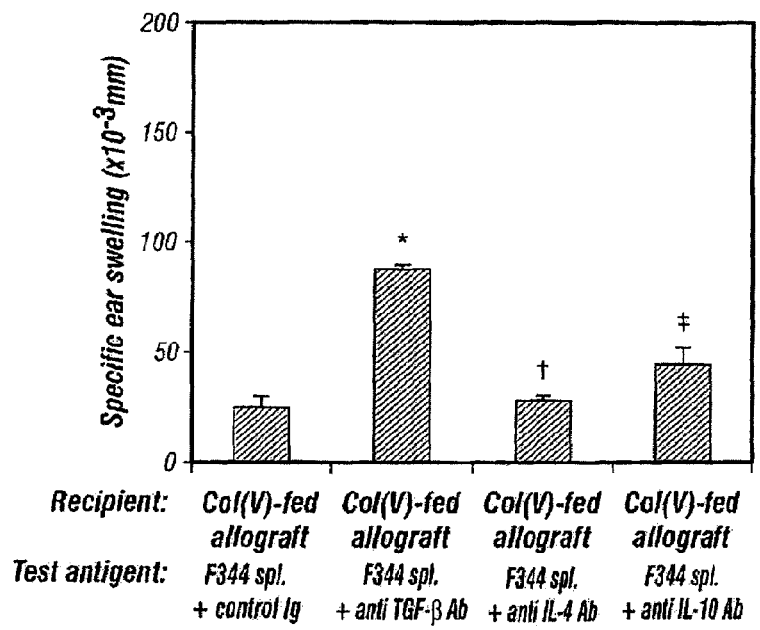

FIG. 18. Graph of data illustrating that neutralization of TGF-β restores DTH responses to donor alloantigens in col (V)-fed allograft recipients. Col(V)-fed WKY rats were challenged in the right pinnae with $10^7$ irradiated (3000 rad) donor-derived F344 splenocytes mixed with either 5 μg of polyclonal anti-TGF-β Ab or anti-IL-4 or IL-10 Ab in PBS two weeks post-transplantation. The left pinnae received an equal volume of diluent plus splenocytes, and served as the control site. For negative controls, a separate group of col(V)-fed allografts received control immunoglobulins with splenocytes into the right pinnae and an equal volume of diluent plus splenocytes into the left pinnae. The ear thickness was measured with a micrometer caliper in a blinded fashion immediately before and 24 h after injection and the specific ear swelling calculated as described below. Spl, splenocytes. Data represent the mean±SEM of specific ear swelling in mm×$10^{-3}$ of four rats in each group [*p<0.03 and †,‡p>0.05 compared to col(V)-fed allografts challenged with antigens mixed with control immunoglobulin.] The restoration of the DTH responses in col(V)-fed allografts with anti-TFG-β, anti-IL-4, and anti-IL-10 antibodies relative to control allografts was 75.7%, 24.3% and 39.9%, respectively.

Figure 19:
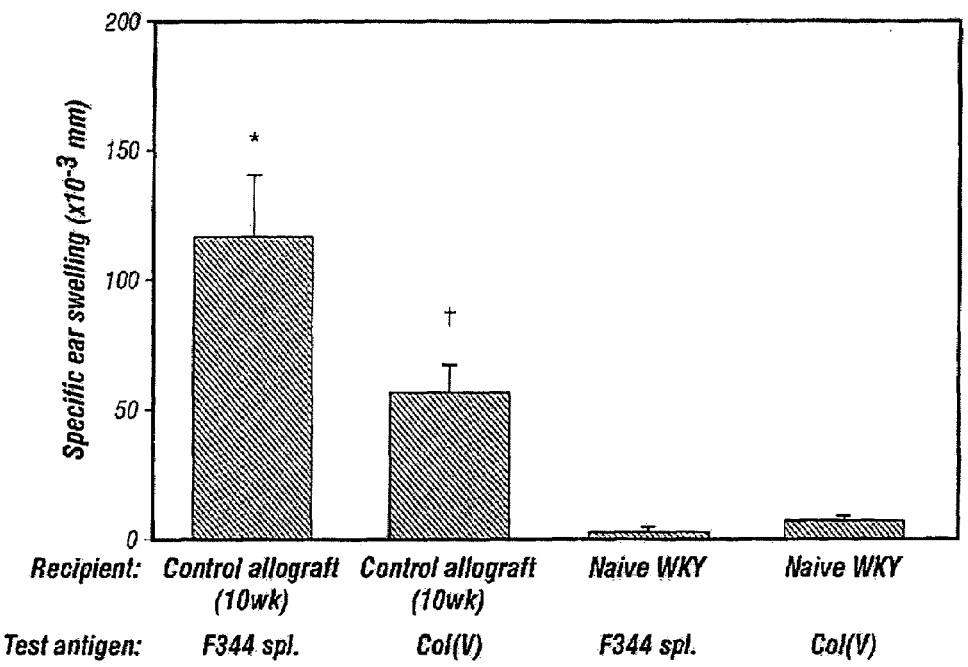

FIG. 19. Graph of data illustrating DTH responses to donor alloantigens, col(II), col(V), col(XI), and third party alloantigens in control allograft recipients ten weeks post-transplantation. Animals received 10' irradiated (3000 rad) donor-derived F344 splenocytes, third party (BN) splenocytes, or 15 μg of col(II), col(V), or col(XI) into the right pinnae and diluent into the left pinnae. The ear thickness was measured with a micrometer caliper in a blinded fashion immediately before and 24 h after injection. The specific ear swelling was calculated as described below. Spl, splenocytes. Data represent the mean±SEM of specific ear swelling in mm×$10^{-3}$ of three rats in each group [*p<0.05 compared to nave WKY rats challenged with F344 splenocytes or col(V)].

Figure 20:
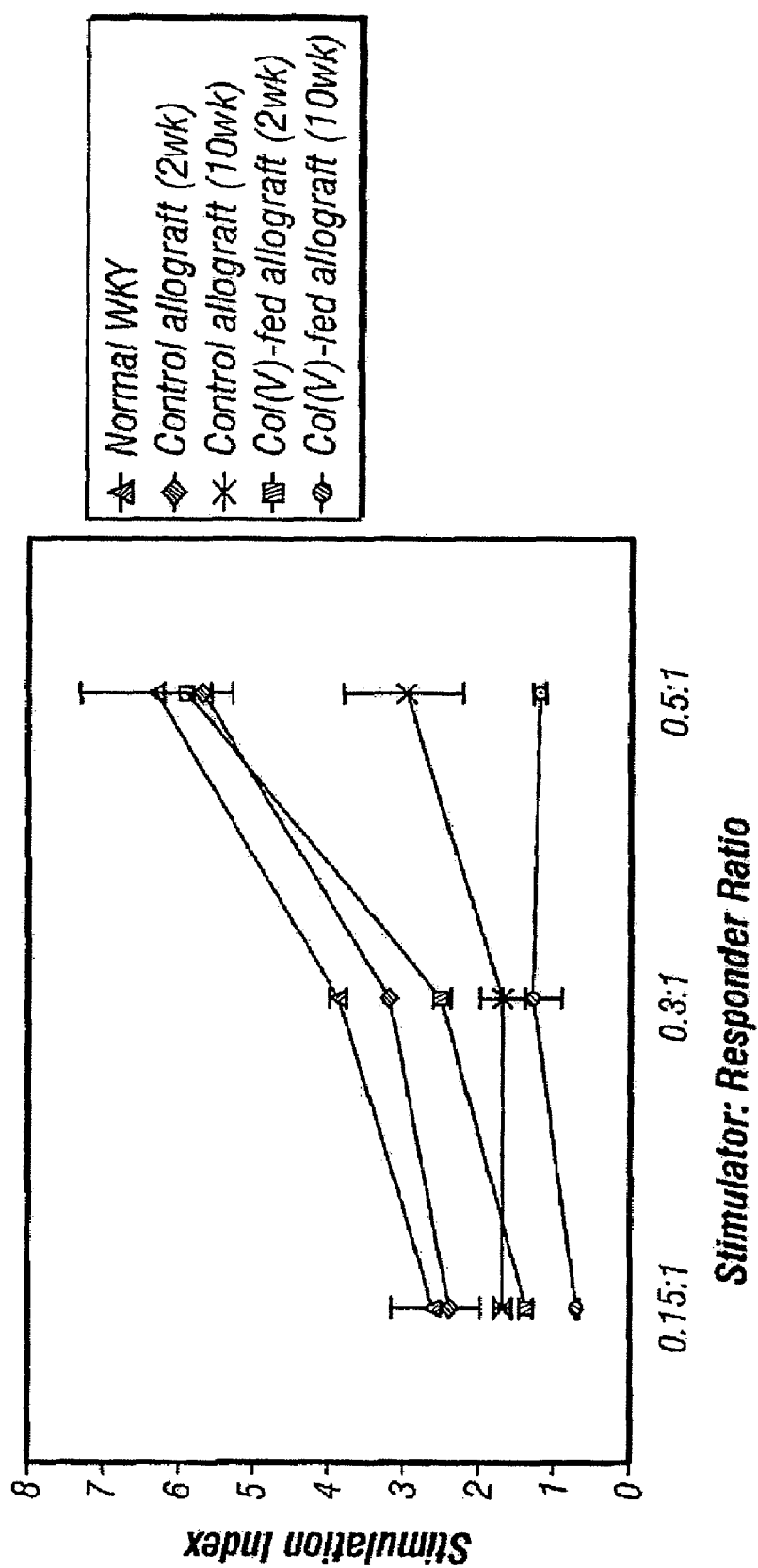

FIG. 20. Mixed leukocyte reaction. Varying ratios of mitomycin-C-treated F344 splenocytes (stimulators) were incubated with $3 \times 10^5$ lymph node T-lymphocytes (responders) from WKY rats (Normal), or WKY rats that were fed col(V). Eighteen hours prior to the completion of a 5 day incubation, the cells were pulsed with $^3$H and proliferation determined by counts/minute (cpm) of thymidine incorporation. Stimulation index equals the multiples of proliferation in lymph node lymphocytes induced by varying quantity of stimulator cells relative to proliferation of lymph node lymphocytes alone. Data representative of three experiments.

FIG. 21A, FIG. 21B, FIG. 21C, and FIG. 21D. Upper panel: Gross anatomy of control allograft lungs FIG. 21A, and col(V)-fed allograft lungs FIG. 21B ten weeks post-transplantation. The left (L) lung is the transplanted lung and the right (R) is the native lung in each panel. The control allograft lung was dark brown in color, shrunken, and of firm consistency compared to the native lung. However, the col (V)-fed allograft lung had a nearly normal appearance with only slight discoloration. Lower panel: Photomicrograph of histology of control allografts FIG. 21C and col(V)-fed allografts FIG. 21D ten weeks post-transplantation. Control allografts developed extensive interstitial nomonuclear cell infiltrates, fibrosis, and obliteration of small airways by granulation tissue, which are pathologic lesions of BO. In contrast, col(V)-fed allografts only had mild alveolar infiltrates, without interstitial inflammation which describes the pathology of mild acute rejection (grade A2). Photomicrographs representative of five rats in each group.

Figure 22:
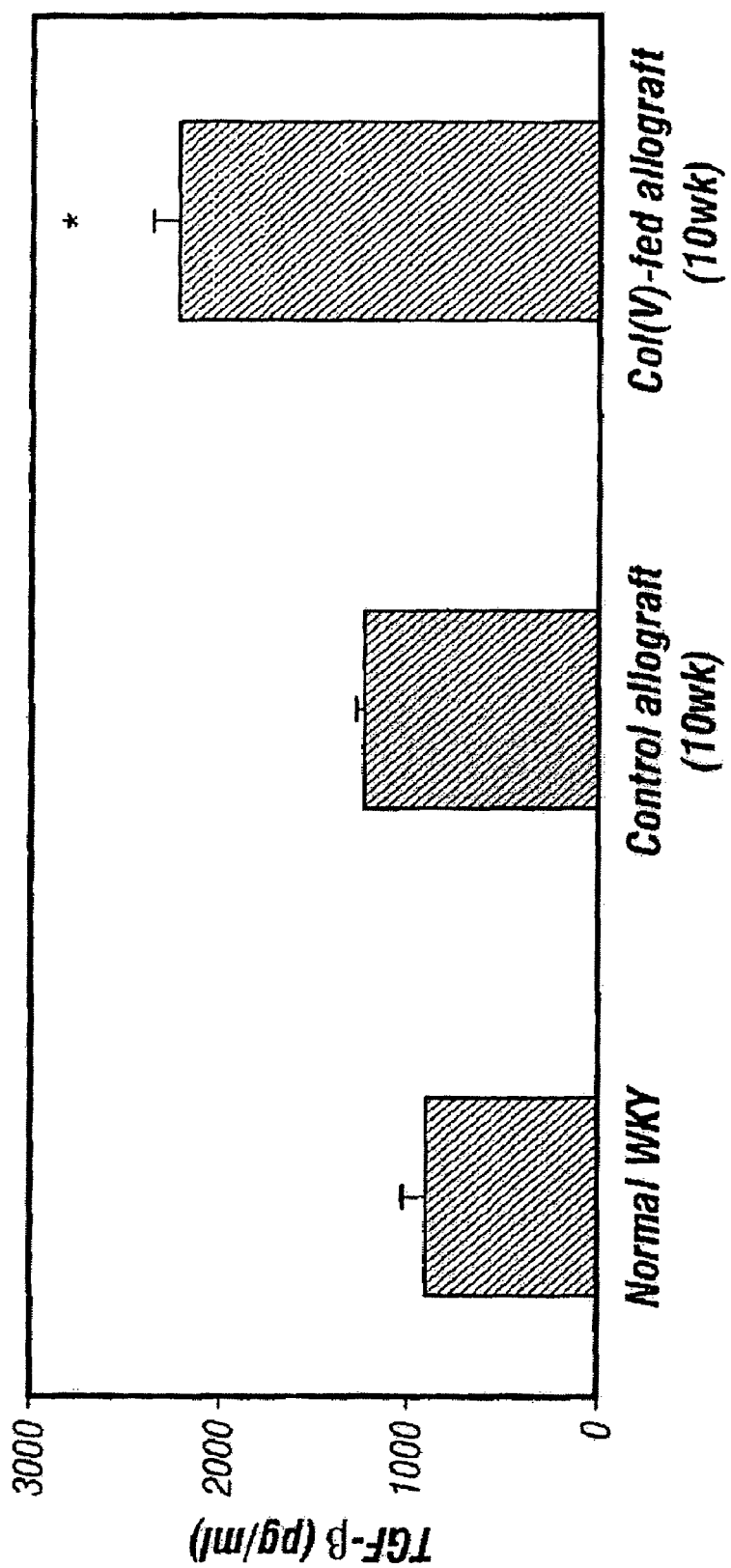

FIG. 22. Graphical illustration of TFG-β levels in serum of normal WKY rats, control allograft recipients, and col(V)-fed allograft recipients ten weeks after transplantation. Levels of TFG-β in serum were determined by ELISA. Data represent mean±SEM of three rats in each group. (*p<0.05 compared to control allografts).

Figure 23:
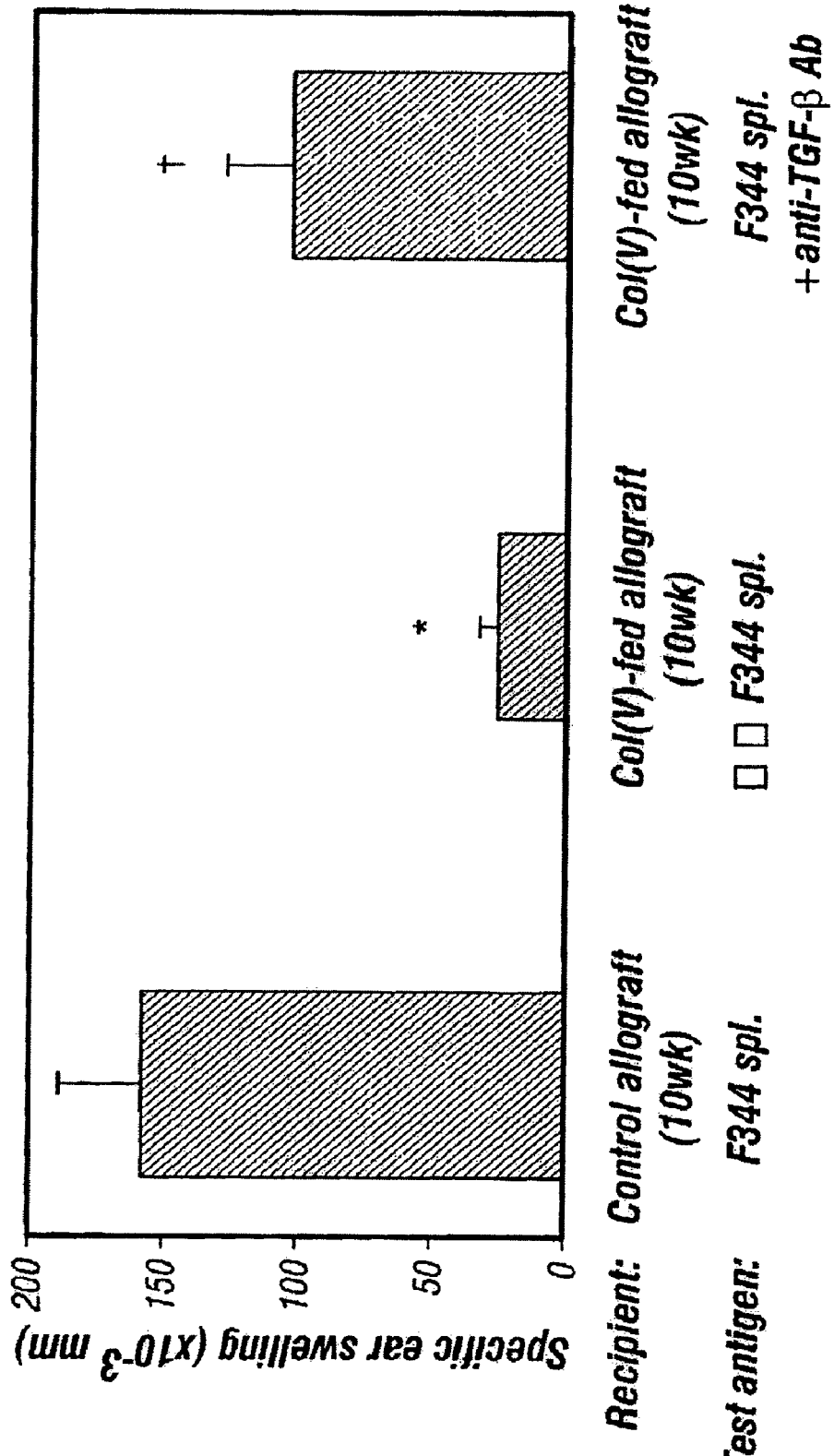

FIG. 23. Graphical representation of Neutralization of TGF-β in DTH Response; Col(V)-fed WKY rats received $10^7$ irradiated (3000 rad) donor-derived F344 splenocytes mixed with 5 μg of polyclonal chicken anti-rat TFG-β Ab in to the right pinnae and diluent into the left pinnae. For negative controls, a separate group of col(V)-fed allografts received $10^7$ irradiated (3000 rad) donor-derived F344 splenocytes mixed with 5 μg of control chicken immunoglobulins or control goat immunoglobulins into the right pinnae and diluent into the left. The Specific Ear Swelling was determined as described.

Figure 24:
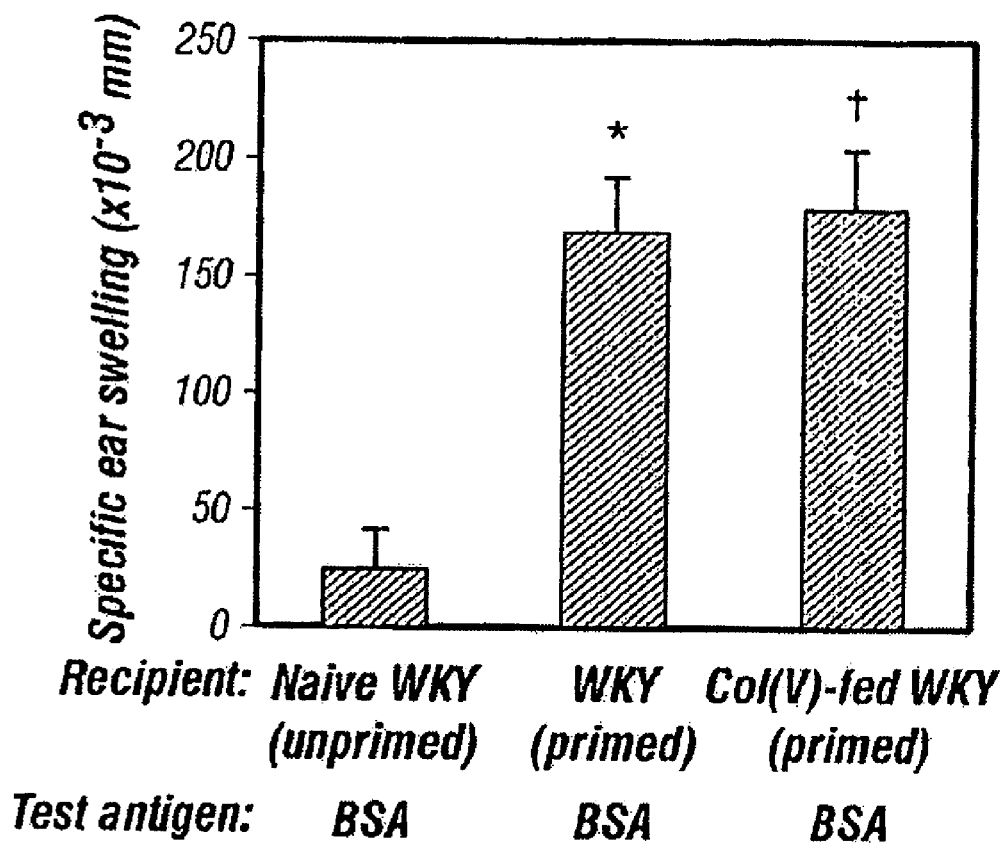

FIG. 24. Graphical representation of DTH responses to BSA in naïve and col(V)-fed WKY rats. Naïve and col(V)-fed WKY rats were primed by s.c. injection of 100 μg of BSA in adjuvant and seven days later challenged with 2% heat aggregated BSA solution in the right pinnae and diluent in the left. The ear thickness was measured with a micrometer caliper in a blinded fashion immediately before and 24 h after injection and the specific ear swelling calculated as described above. Unprimed WKY rats served as controls. Data represent the mean±SEM of specific ear swelling in mm×$10^{-3}$ of four rats in each group (*$p<0.018$ compared to unprimed naïve WKY rats and †p ? 0.05 compared to primed WKY rats).

FIG. 25. Table 4 is a listing of experimental groups used in example 6.

FIG. 26. Table 5 is a summary of results of the experiments reported in example 8.

DESCRIPTION

For the purposes of promoting an understanding of the principles of the invention, reference will now be made to the preferred embodiments thereof, and specific language will be used to describe the same. It will nevertheless be understood that no limitation of the scope of the invention is thereby intended, such alterations, modifications, and further applications of the principles of the invention being contemplated as would normally occur to one skilled in the art to which the invention relates.

A number of explanations and experiments are provided by way of explanation and not limitation. No theory of how the invention operates is to be considered limiting, whether proffered by virtue of description, comparison, explanation or example.

The compositions and methodologies disclosed and implied herein are useful for both human and other lower animal (e.g., pets, zoo, or domestic animals) applications. Accordingly, the following examples and discussion are presented by way of guidance and explanation and not limitation.

As used herein the term 'assessing' as used, for example, in the phrase, 'assessing a patient for . . . " includes, but is not limited to diagnosing, screening, evaluating, monitoring and the like for any discernable parameter that is shown to correlate with a given disease, disorder or condition, and the like. The term assessing as used herein includes, but is not limited to, at least one of the following activities: diagnosing patients to determine if they have a specific or general medical condition; monitoring patients with a known or suspected medical condition to track the progress of the disease or the efficacy of a treatment regime; screening patients to estimate the likelihood that they will develop a given medical condition; evaluating the probability that a given patient has or is at risk for developing a given disease or medical condition; detecting the presence of or propensity or susceptibility to developing a disease, syndrome, or condition; and predicting the long or short term prognosis for developing and/or recovering from a given medical condition, disease, disorder or the like.

As used herein the term 'medical condition' includes syndromes, diseases, conditions and the like.

Studies in the rat lung transplant model have shown that the lung is rejected due to a specific anti-Type V collagen autoimmune response. For additional discussion see: U.S. Patent Application Publication No. 2003/0078208A based on U.S. patent application Ser. No. 10/243,797 filed on Sep. 13, 2003 by David S. Wilkes and incorporated herein by reference in its entirety; and, "Type V Collagen Modulates Alloantigen-Induced Pathology and Immunology in the Lung," by Davic C. Mares, et. al., in *Am. J. Respir, Cell Mol. Biol, Vol.* 23, pp. 62-70, 2000. Collagen type V [col(V)] is a minor collagen present in the lung (Madri and Furthmayr, 1980) and is located in the peribronchiolar connective tissues (Madri and Furthmayr, 1979), alveolar interstitium (Konomi, et al., 1984), and capillary basement membranes (Madri and Furthmayr, 1979). The α-1 chain of α1 (V) is nearly 76% homologous to the α2-chain of type XI collagen [α2(XI)] (Cremer, et al., 1994), and the gene for α2(XI) is located in the MHC class II loci of mice and humans (Hanson, et al., 1989), and shares amino acid sequences with MHC class II (Wilson, et al., 1995). MHC-derived peptides have been utilized to induce tolerance in allografts other than the lung. The present inventors selected col(V) to modulate immune responses in lung allografts due to the possible presence of MHC-"like" sequences in col(V).

Referring now to the results of example 1 (presented below), lung transplant patients with an increased autoimmune response to collagen appear to be at a higher risk for transplantation rejection. In accordance with these and other observations, one embodiment is a method for predicting and/or following the progression of lung transplant rejection by measuring either cellular or humoral autoimmune response to collagen in a patient awaiting or having undergone a lung transplant. In one embodiment the biomarker for lung transplant rejection followed is autoimmunity to Type V collagen and/or epitopes of Type V collagen.

It has been reported in the medical literature that self antigens, such as myosin and heat shock proteins can become the target of immune responses during cardiac and skin allograft rejection (Fedoseyeva, et al., 1999; Duquesnoy, et al., 1999; Birk, 1999). It is also reported that lung allograft rejection in rodents is associated with T cell responses to collagen type V (Mares, et al., 2000), a minor collagen found in the lung and skin that is essential for tissue elasticity and compliance (Schwarze, et al., 2000). Fragments of col(V) are released into the bronchoalveolar lavage (BAL) fluid after lung transplantation and adoptive transfer of col(V)-specific T cells induces "rejection-like" pathology in transplanted lung isografts (Hague, et al., 2002). Oral tolerance induced by feeding col(V) to rats prior to lung transplantation abrogated acute rejection and the onset of BO (Yasufuku, et al., 2001; Yasufuku, et al., 2002).

One formal possibility is that patients who receive a lung transplant may develop cellular and/or humoral immunity to col(V), and that this autoimmune response increases their risk of developing BO. Some of the results of example 2 (presented below) are consistent with col(V) immuno-reactivity developing after lung transplantation and representing a major risk factor for brochiolitis obliterans syndrome (BOS).

The histopathology of BO suggests that inflammation and response to injury result in a final common pathway, the development of lesions leading to graft failure. The scarcity of this syndrome outside of the lung transplant setting indicates that alloimmune mechanisms play a central role in this process. However, the fact that acute rejection and MHC mismatch did not necessarily lead to BOS suggests that other immune factors may be important. The results of example 2 (presented below) suggest that lung transplantation may induce the development of de novo autoimmunity to a self antigen, collagen type V (Estenne, et al., 2002). Indeed, the relative risk imparted by col(V) autoimmunity after lung transplant observed in this study was on the order of 8-10-fold greater than factors such as the incidence of acute rejection episodes, previously identified as a post-transplant risk for BOS (Sharples, et al., 2002).

Preliminary analysis of the T cells responsible for col(V) DTH reactivity in the peripheral blood of lung transplant recipients indicates that the majority are CD4$^+$, although a role for col(V)-specific CD8+ T effector cells cannot be excluded (Burlingham, W., Rodriguez, D. and Jankowska-Gan, E., unpublished). In the rat model, a col(V)-specific, MHC class II-restricted CD4$^+$ T-cell clone derived by in vitro culture from a rejecting lung transplant was able to mediate lung rejection pathology in a left lung isograft, with some pathology spreading to the native right lung (Hague, et al., 2002). No damage to native lungs was seen when the same clone was injected into a normal rat, these results suggest that ischemia and reperfusion injury accompanying the isograft procedure were required to initiate immunopathology. Not all clones of T cells isolated from rejecting allografts were pathogenic, and some appear to be protective (D. Wilkes, unpublished), suggesting that CD4$^+$ T regulatory cells specific for col(V) or other tissue antigens may play a role in restraining the autoimmune pathology. Indeed, the rapid progression to graft loss after BOS onset in patient L3, and the stabilization of function in some patients with anti-col(V) autoimmunity (FIG. 1B, left panel and 1C, middle panel), was correlated with loss or gain of a regulated DTH response to donor antigens (W. Burlingham and E. Jankowska-Gan, unpublished) a phenomenon described previously in kidney transplantation in humans (VanBuskirk, et al, 1998: Burlingham, et al., 2000, Cai, et al., 2004), and non-human primates (Torrealba, et al., 2004).

HLA DR mismatch is a well-known risk factor for early acute rejection of organ transplants (Ayoub, et al., 1982). This could partly explain why DR mismatch is associated with BOS (van den Berg, et al., 2001). It is also possible that HLA DR matching plays a beneficial role in lung transplantation by establishing conditions for immune regulation directed to donor and self antigens (Rodriguez, et al., 2004).

There is a well-established connection between B cell autoimmunity to collagen Type IV and Goodpasture's syndrome (Hudson, et al., 2003), which was confirmed in the present study at the T cell level using the trans-vivo DTH assay (FIG. 3B). Release of collagen IV from the kidney due to T cell mediated injury predisposes the system to local B cell immunity and anti-glomerular basement membrane IgG deposition in a rat model of this disease. Similarly, release of col(V) from the ischemically-injured lung transplant in the context of alloreactivity might activate col(V)-specific effector T cells, promoting local col(V)-specific B cell response and deposition of C'-fixing IgG in the sub-epithelial matrix.

One result of example 2, reported herein, is finding that a pre-existing col(V)-specific autoimmunity exists in patients with IPF. The etiology of IPF remains a mystery, as does the reason for the poor prognosis of these patients after lung transplantation (REF). Whether or not anti-col (V)-specific T cells contribute to the fibrotic process underlying this lung disease, or to poor early outcomes in lung transplantation for IPF, remains to be determined, although these data are clearly consisting with a connection between these phenomena.

The unexpected results of example 2 suggest treating patients diagnosed with or at risk for developing IPF by restoring or reinforcing self-tolerance to col(V) prior to transplantation. One embodiment is a method of treating IPF by administering col(V) either by oral therapy (Yasufuku, et al., 2001; Yasufuku, et al., 2002) interstitially into the lung or by other desensitization strategies on a dosage regiment designed to increase the patient' tolerance for collagens including, but not necessarily limited to collagen Type V and antigenic components and variants thereof.

Still another embodiment is an antibody based assay for diagnosing or monitoring diseases that include an autoimmune response.

Detecting the presence of antibodies to collagen in accordance with some embodiments may be accomplished using any of a number of immunoassay procedures, such as by ELISA procedures. A wide range of immunoassay techniques is available as can be seen by reference to standard immunoassay textbooks these include, but are not limited to single-site and two-site or "sandwich" assays of the non-competitive types, as well as the traditional competitive binding assays.

Sandwich assays are among the most useful and commonly used antibody based assay methods and may be used to practice various embodiments. A number of variations of the sandwich assay technique exist, and all are intended to be encompassed by various embodiments. Briefly, in a typical assay to detect antibodies in a sample, an unlabelled antigen is immobilized on a solid substrate and the sample to be tested is contacted with the bound antigen molecule. After a suitable period of incubation, i.e. for a period of time sufficient to allow formation of an antibody-antigen complex, a second antibody such as anti-human IgG, labeled with a reporter molecule capable of producing a detectable signal, is then added and incubated, allowing time sufficient for the formation of an antibody-antigen-labeled antibody. Any un-reacted material is washed away, and the presence of the antibody to be detected in the sample is determined by observation of a signal produced by the reporter molecule. The results may either be qualitative, e.g., by simple observation of the visible signal, or may be measured by comparing the signal generated by a sample of interest with a control sample containing known amounts of antibody to be detected. Variations on this assay include a simultaneous assay, in which both the sample and labeled antibody are added simultaneously to the bound antigen. These techniques are well known, including any minor variations as will be readily apparent to those in the art.

In the typical sandwich assay, antigen is immobilized, for example by being either covalently or passively bound to a solid surface. In some embodiments the solid surface is typically glass or a polymer, the most commonly used polymers being cellulose, polyacrylamide, nylon, polystyrene, polyvinyl chloride or polypropylene. The solid supports may be in the form of tubes, beads, discs, or micro-plates, or any other surface suitable for conducting an immunoassay. Various binding processes are well-known in the art and generally consist of cross linking, covalent binding or physical adsorption of the antigen to a given surface. The immobilized antigen is then washed in preparation for the addition of the test sample. An aliquot of the sample to be tested is then contacted with the immobilized antigen and incubated for a period of time sufficient (e.g. 2-40 minutes) and under suitable conditions (e.g. 25° C.) to allow binding of any antibody to collagen present in the sample. The actual length of contact time, buffer conditions, temperatures and the like are readily adjustable parameters and are typically readily arrived at for a given test. Following the incubation period, the immobilized antigen including any bound antibody is washed and dried, and incubated with a second antibody specific for the bound antibody, for example anti-human IgG. The second antibody is linked to a reporter molecule which is used to indicate the binding of the second antibody to the antibody-immobilized antigen complex.

The term "moiety" as used herein includes molecules, atoms, chemical functional groups, and the like.

The term "reporter molecule" as used in the present specification, includes molecules which, by their chemical nature, provide an analytically identifiable signal which allows the detection of antigen-bound antibody. Detection may be either qualitative or quantitative. The most commonly used reporter molecules in this type of assay include enzymes, fluorophores or radionuclide-containing molecules (i.e. radioisotopes), chemiluminescent molecules and the like. In the case of an enzyme immunoassay (EIA), an enzyme is conjugated to the second antibody, generally by means of glutaraldeyde or periodate. As will be readily recognized, however, a wide variety of different conjugation techniques exist, which are readily available in the art and optimal or near optimal conditions for specific assays and tests can be readily arrived at with only minimal experimentation. Commonly used reporter enzymes in these types of assays include, but are not limited to, horseradish peroxidase, glucose oxidase, beta-galactosidase and alkaline phosphatase, amongst others. The substrates to be used with specific enzymes are generally chosen for the production, upon hydrolysis by the corresponding enzyme, of a detectable change in a given signal associated with the presence of the reporter molecule or atom. It is also possible to employ fluorogenic substrates, which yield a fluorescent product rather than the chromogenic substrates noted above. In most cases, the enzyme-labeled antibody is added to the first antibody-antigen complex, allowed to bind, and then the excess reagent is washed away. A solution containing the appropriate substrate is then added to the complex of antibody-antigen-labeled antibody. The substrate will react with the enzyme linked to the second antibody, producing a detectable visual signal, which may be further quantitated, usually using a spectrophotometric instrument, to give indication of the amount of antibody which was present in the sample. The term, "reporter molecule" also extends to use of cell agglutination or inhibition of agglutination, such as glass or latex beads, and the like. Additionally, the reporter can be a radioactive group or atom whose presence is detected by, for example, scintillation counting.

Alternately, fluorescent compounds such as fluorescein and rhodamine, may be chemically coupled to antibodies without significantly altering their binding capacity. When activated by illumination with light of a particular wavelength, the fluorochrome-labeled antibodies adsorbs light energy, inducing a state of excitability in the molecule, followed by emission of the light at a characteristic color, in some embodiment the emitted signal is visually detectable with a light microscope while in other embodiments the signal may be outside the visible spectra. As in the EIA, the fluorescent labeled antibody is allowed to bind to the first antibody-antigen complex. After washing off the unbound reagent, the remaining tertiary complex is then exposed to light of the appropriate wavelength and the fluorescence observed indicates the presence of the antibody of interest. Immunofluorescence and EIA techniques are both very well established in the art of are readily adaptable for use with various embodiments disclosed herein. In addition, other reporter molecules, such as radioisotope, chemiluminescent, fluorescent, or bioluminescent molecules and the like, may also be employed.

In order to practice some embodiments it may be necessary to obtain pure or partially pure collagen or an epitope or antigenic portion thereof. These materials for example Type V collagen or antigenic portions thereof can be readily obtained by a variety of means including, but not limited to, animal sources, human cadavers, or recombinant means to name a few. Additional methods include partial digests of collagen such as Type V collagen.

One aspect comprises diagnosing diseases such as Idiopathic Pulmonary Fibrosis by identifying evidence of an autoimmune response to lung connection tissue such as Type V collagen. Evidence of connective tissue may include Type V collagen and epitopes of the same. As clearly illustrated in example 3, one approach which can be used to identify and or track patients with IPF or at a heightened for developing IPF or BO or BOS is to measure the level of anti-Type V collagen antibody in patient's bodily fluids.

Another aspect includes treating patients diagnosed with medical conditions, or thought to have medical conditions, or thought be at heightened risk for developing medical conditions related to autoimmune rejection of collagen found in lung tissue by administering a safe and therapeutically effective amount of a compound such as Type V collagen and various antigenic components of Type V collagen and/or analogues thereof. These compounds can be administered by any means known in the field including oral feeding, intrapulmonary instillation, inhalation, injection and the like. The effective amount of the therapeutic compound and the duration of the treatment will likely depend on each patient and can be readily calibrated to induce a therapeutic effect, e.g., at least a partial suppression of a patient's autoimmune response to collagens such as Type V collagen or some fragment thereof.

Additional general discussions of the therapeutic value of using MCH epitopes to treat diseases or medical conditions involving the immune system can be found in, for example, U.S. Pat. No. 6,911,220, issued to Sachs on Jun. 28, 2005 and U.S. Patent Publication No. 2003/0078208 A1 (Wilkes) published on Apr. 24, 2003, both of which are herein incorporated by references in their entireties.

In one embodiment patients diagnosed with, or thought to be suffering from, a pulmonary disease or disorder which includes or is caused by an autoimmune response can be treated with immunosuppressive drugs, including, for example, Cyclosporine. For a further general discussion of Cyclosporine including a discussion of some of its effects on the immune system the reader is directed to U.S. Pat. Nos. 6,410,696 issued to Davalian, et al. on Jun. 25, 2005 and 5,990,274 issued to Wang on Nov. 23, 1999, both of which are incorporated herein by reference in their entirety.

EXAMPLES

Example 1

In order to determine if post-transplant lung patients were also developing autoimmunity specific for Type V collagen, we performed delayed type hypersensitivity (DTH) assays using leukocytes from 8 lung transplant recipients and 5 renal transplant recipients (which have Goodpasture's syndrome, a collagen (col) Type IV-autoimmunity) and three different collagens. As shown in FIG. 3 Panel A, T cells from lung transplant recipients responded to col(V), but not col(IV) or col(II), while T cells from patients with Goodpasture's syndrome had significantly higher DTH responses to col(IV) without responses to col(V) or col(II). This key discovery indicates that lung transplant patients may have anti-Type V collagen autoimmunity.

We next determined if an anti-Type V collagen autoimmune response could be seen in any patients awaiting a lung transplant, thus reflecting a pre-existing condition which could predispose certain patients to poor lung function and rejection. An analysis of the anti-col(V) DTH response in 23 patients with various end-stage lung diseases awaiting lung transplantation showed that one specific group does have an anti-Type V collagen autoimmune response. As shown in FIG. 5, patients with Idiopathic Pulmonary Fibrosis (IPF) displayed an anti-col(V) DTH response that was twice as high as that seen in patients with any other disease. This key discovery indicates that IPF may be caused by an autoimmune response to Type V Collagen.

To further support this finding, patients awaiting lung transplantation due to several different causes were tested for their autoimmune response to either col(V) or col(II). As shown in FIG. 3 Panel B, only T cells from IPF patients displayed an autoimmune response that was specific to Type V collagen. It is also interesting to show that patients with IPF transplanted at the University of Wisconsin had significantly lower 1 year graft survival (p=0.05) (FIG. 3 Panel C), which suggests that a pre-existing autoimmune response to Type V collagen can result in a faster loss of lung function and death. The results shown in FIGS. 3 and 5 indicate that IPF can be caused by an autoimmune response to Type V collagen, that these patients will reject their lungs at a faster rate due to this autoimmune response, and that this represents an additional group of patients who will respond to oral tolerance therapy with Type V collagen.

To support the idea that a pre-existing autoimmune response to Type V collagen, as seen in IPF patients, would result in lung destruction we used our rat transplant model. WKY rats were immunized with either nothing (FIG. 6a), hen egg lysozyme (HEL) (FIG. 6b) or Type V collagen (FIG. 6c) and then transplanted with an isograft lung. As seen, rats immunized with either nothing or HEL showed normal lung pathology. In contrast, rats with an active immune response to Type V collagen destroyed their isograft lung within about 30 days. These data further are consistent with an autoimmune response to Type V collagen indicative of a higher risk of rejection of transplanted lung and lung tissue than that expected in lung transplant recipients that do not exhibit an autoimmune response to Type V collagen.

Example 2

Bronchiolitis obliterans syndrome (BOS) is the leading cause of graft loss after lung transplantation. Collagen Type V (col(V)), a minor collagen in the lung extracellular matrix, has been implicated in the pathogenesis of rat lung allograft rejection. To test the hypothesis that autoimmunity to col(V) after human lung transplantation predisposes to BOS, we analyzed delayed-type hypersensitivity (DTH) responses in the peripheral blood and antibody responses in the bronchoalveolar lavage (BAL).

From 1988-June 2003, all lung transplants performed at the University of Wisconsin (n=229) were analyzed retrospectively for risk factors predisposing patients to BOS. DTH or antibodies to col(V) or col(II) were measured in 56 of these recipients, 10 normal controls, and 25 patients awaiting transplantation.

All subjects were consented using IRB-approved informed consent procedures at the University of Wisconsin and Indiana University School of Medicine. Of the 229 patients receiving primary lung transplants at the University of Wisconsin Hospital and Clinics from 1988-June 2003, 3 were excluded from analysis due to technical failures.

All patients underwent protocol bronchoalveolar lavage (BAL) and transbronchial biopsy (TBB) at 0.5, 1, 3, 6, 9 and 12 months post-transplant, and later when clinically indicated. TBB tissue was screened for cytomegalovirus (CMV) inclusions and cellular infiltrates. The col(V) study patients (n=56) included 29 enrolled in a post-transplant DTH study protocol initiated in 2000, 23 patients from whom stored BAL were tested retrospectively for antibody to col(V), and 4 patients tested only for DTH beginning at year 3-6 post-transplant. Otherwise, blood samples were drawn for the DTH assay at approximately 6, 12, and 18 months, and yearly thereafter. Non-smoking adult blood donors, and volunteers undergoing bronchoscopy and collection of BAL fluid, served as a negative control group. Five patients post-kidney transplant for Goodpasture's syndrome were also recruited as control blood donors in DTH tests.

BOS level I, the primary study end point, was diagnosed by a sustained drop in FEV1 to <80% of the maximum post-transplant value at least 90 days after transplantation (9).

IgG was affinity purified from the BAL fluid of patients and controls by passage over a commercially prepared Protein G Sepharose column (Pharmacia, Piscataway, N.J.) per manufacturer's protocol. All eluted fractions were frozen at −80° C. until use.

Antibodies to col(V) were analyzed using a western-blotting technique as described previously, except that sheep anti-human IgG isotype-specific antibodies were used for detection. Bovine col(II) and col(V) (Collaborative Biomedical Products—Becton, Dickinson, Bedford Mass.) or col(V) extracted from human placenta were used as the target antigens.

CB-17 SCID mice were purchased from Harlan Sprague Dawley, Inc (Indianapolis, Ind.) or were bred locally. All animals were housed and treated in accordance with NIH guidelines.

The trans-vivo DTH assay was performed by co-transfer of human PBMC and antigens into the footpads of SOID mice as described previously. Human col(V), col(IV) (Fluka, Inc., Buchs, Switzerland) or bovine col(II) (5 µg/injection; Southern Biotech, Birmingham, Ala.) were the test antigens. Footpad thickness was measured before and 24 hours after injection using a dial thickness gauge. Background swelling, due to PBMC with buffer alone, was subtracted to determine antigen-specific response. Swelling responses of $\geq 25 \times 10^4$ inches over background were considered positive.

BOS-free survival rates were estimated using the methods of Kaplan and Meier and compared between groups using a log-rank test. The criteria for a negative col(V) DTH or Ab response was stringent—patients with either a faintly positive anti-Col(V) band on Western blot or a minimally positive DTH response ($25 \times 10^4$ inches) were considered positive, even if all other time-points were negative. Cox's proportional hazards model was used to evaluate the association between suspected risk factors, some of which were time-varying, and BOS-free survival. P-values<0.05 were considered significant. All analyses were performed using SAS statistical software release 6.12, SAS Institute Inc. (Cary, N.C.). Pre-transplant col(V) DTH responses were compared between an IPF patient subgroup and other groups using a Kruskal-Wallis test.

Referring now to Table 1 (FIG. 7), summarized here are the demographics and incidence of BOS in 226 lung transplant recipients at the University of WI, Madison. BOS developed in 86 (38%) patients. There were more single (n=133) as compared to bilateral lung transplants (n=93). The mean follow-up period was 3.7 years. The composition of the overall population and that of the col(V) study subset were similar with respect to the incidence of BOS, mean follow-up time, and proportion of patients in each disease category.

We have previously reported that IgG2 production was selectively increased in BAL fluid during episodes of lung allograft rejection. As illustrated in FIG. 1A, IgG antibodies isolated from BAL of lung transplant patients L3 (BOS level III—graft loss) and L41 (No BOS) bound strongly to col(V), but not col(II) in Western blot. Both bovine and human col(V)

were recognized equally by the BAL IgG (data not shown), indicating that the target epitope is conserved across species. In contrast to patients L3 and L41, weak or absent binding to col(V) was observed in BAL samples of L31, which did not develop BOS (FIG. 1A); negative results were also seen with IgG isolated from BAL of normal volunteers (n=10; data not shown).

Next we examined the relationship of anti-col(V) autoimmunity in the periphery, using the trans-vivo DTH test, and locally, by BAL antibody analysis, to the development of BOS. The clinical course, of the same three patients, is shown in FIG. 1B. Patient L3 had a strong and specific anti-col(V) DTH reactivity at the earliest time post-transplant tested (180 d.), when FEV-1 was still at a maximum level. A strong col(V) antibody response was also detected just prior to development of BOS (black rectangle), when the values for FEV-1 were hovering around 80% of maximum. Both DTH and antibody response to col(V) were detected during the onset of BOS, but DTH reactivity was lost at BOS end stage (grade III) on day 450.

Patient L41 is an example of a patient with strong early responses to col(V), but no sustained drop in allograft function. Anti-col(V) antibody(2+) was detected on days 48 through 213 and all PBMC samples obtained from day 188 through 460 were DTH-positive to col(V). Since d.500 the anti-col(V) DTH response has been variable and generally declining. After an episode of acute rejection on day 980, pulmonary function has stabilized at approximately 82% of maximum FEV1, just above the cutoff for BOS-1.

Patient L31 had a weak antibody response to col(V) at day 49 and a minimally positive anti-col(V) DTH response at day 400, but never developed strong autoimmune reactivity. The patient has maintained excellent graft function for >5 years, and in the most recent PBMC sample (day 1600) remains negative for anti-col(V) DTH response.

These three patterns of col(V) responses and allograft function are representative of those seen in the 56 patient study subgroup. FIG. 1C shows the post-transplant time course of 4 additional patients in each category. Each line represents % max FEV1 for a single patient and each red symbol represents a positive test for col(V) (either antibody in the BAL or $\geq$25 net foot-pad swelling in the DTH assay). Each green symbol indicates a test with a negative anti-col(V) result.

All four patients in the first category (anti-col(V)+, BOS+), like patient L3, showed a positive DTH or antibody test result prior to loss of graft function. Patients in the third category (anti-col(V)-, BOS-) rarely had a response to col(V) and all continue BOS-free with follow-up of 3-6 years. The patients in the middle category are perhaps the most interesting since they all managed to maintain excellent graft function 1-3 years after transplant despite repeated positive tests for anti-col(V) response.

The results of a retrospective analysis of risk factors associated with either BOS or graft loss or BOS alone as the end point are shown in Table 2 (FIG. 8). Pre-transplant factors predisposing to a significantly higher (p<0.05) risk of BOS in the entire patient population included having a 2 DR mismatch with the donor (RR=1.64 vs. 0 or 1DR mismatch), and having a disease category of chronic obstructive pulmonary disease, COPD (RR=1.7) or "other" (RR=1.9). Pre-transplant factors predisposing to a lower incidence of BOS or graft loss included an original disease of cystic fibrosis (CF) or having received a bilateral lung transplant, the main treatment for this disease category (both RR=0.35). Post-transplant risk factors for BOS were also assessed. As expected, the incidence of acute rejection episodes was associated with a 1.4 to 1.5-fold higher risk of BOS that was highly significant. However, neither the transplant of a CMV+ donor lung into a CMV- recipient, nor biopsy-proven CMV in the post-transplant period, was significantly associated with BOS.

Referring again to FIG. 8, Table 2 summarizes the analysis of poor function (BOS I or graft loss) or BOS I development in 56 lung transplant recipients analyzed for responses to col(V) using a Cox proportional hazards model. In this subset of patients, acute rejection was again risk for poor function. The highest RR for poor graft function (12.3) was found in patients with a positive DTH to col(V) at the time-point proximal to BOS onset. DTH response to control col(II) showed no correlation with development of BOS(RR=1.0) indicating that the DTH response to col(V) is a specific marker of BOS risk. FIG. 2 graphically demonstrates the association of DTH responses to col(V) with BOS development. Patients with good lung function (>80% max FEV1) at day 370 (top panel) and at day 760 post-transplant (bottom panel) were divided into col(V)+ vs. col(V)- responders based on antibody and/or DTH analysis and Kaplan-Meier analysis was performed with time to BOS I as the end point. More than half of the patients with anti-col(V) reactivity prior to either time point developed BOS within the next 2 year, whereas patients with negative response to col(V) were predominately BOS-free.

The level of anti-col(V) antibodies in BAL was significantly associated with the development of BOS or graft loss from any cause (RR=2.3), and with the risk of BOS alone (RR=2.08). When the two indicators, DTH or antibody to col(V), were combined, the RR for BOS or graft loss was 12.7 and that for BOS could not be calculated because all patients who developed BOS had either a positive DTH or antibody response to col(V) at some previous time point Table 2, (FIG. 8).

In order to determine if anti-col(V) responses seen in post-transplant lung patients is simply a reflection of a pre-existing condition which could predispose certain patients to poor function (that is would patients with COPD have higher pre-transplant anti-col(V) responses while those with CF have lower responses), we analyzed the anti-col(V) DTH response in 23 patients with various end-stage lung diseases awaiting lung transplantation. As shown in FIG. 3 Panel A, patients with most end-stage lung disease do not have anti-col(V) DTH responses which are significantly different from that seen in normal subjects with no known lung disease. The exception is patients with IPF. The anti-col(V) DTH response in these patients was twice as high as that seen in patients with any other disease. Interestingly, patients with IPF transplanted at the University of Wisconsin had significantly lower 1 year graft survival (p=0.05, data not shown), but similar 5 year survival and rate of BOS development (Table 1) (FIG. 7).

In an effort to determine if the development of autoimmunity to collagen in post-transplant lung patients was specific for Type V collagen, we performed DTH assays using col(II), col(IV), and col(V) on 8 lung transplant recipients and 5 renal transplant recipients with Goodpasture's syndrome (collagen Type IV-autoimmunity). As shown in FIG. 3 Panel B, lung transplant recipients responded to col(V), but not col(IV) or col(II), while patients with Goodpasture's syndrome had significantly higher DTH responses to col(IV) without responses to col(V) or col(II).

Example 3

Bead Assay for the detection of humoral or antibody-mediated immune responses against Type V collagen. This assay will detect antibodies to Type V collagen as may be present in serum and/or lung lavage fluid from patients that have an autoimmune response Type V collagen. Type V collagen-coated beads along with other necessary diction reagents are provided for this assay. The end-user may provide serum and/or lung lavage fluid, and common reagents such as PBS or these reagents can be assembled in a kit, for carrying out the assay. Briefly, a typical assay is as follows:

1) Streptavidin-coated beads (5 um, binding capacity 10-20 μg/1×10/7 beads (Polyscience, Warrington, Pa.)) were washed two times with sterile PBS. Beads (1×10/7) were suspended in 100 μl of PBS with 40 μg of human Type V collagen and incubated for 60 minutes at 4° C.

2) A positive control was generated by following the same procedures in 1 above, using 20 μm of rabbit antibody to human collagen V antibody (bioten) (Abeam, Cambridge, Mass.).

3) For each assay, 1×106 conjugated beads were washed two times in PBS, and incubated in 100 μl PBS plus 50 μl serum of lung lavage fluid. After incubating for 30-minutes at room temperature, the beads were washed three times with PBS containing 10/% FCS.

4) The beads were suspended in 100 μl of sterile PBS+10% FBS and incubated for about 30 minutes at room temperature with secondary antibody. Typically, 5 μl of anti-human IgG antibody conjugated with R-PE was used (Sigma, Saint Louis). The beads were washed three times in PBS containing 10% FCS, suspended in 300 μl of PBS/FCS solution and analyzed using a flow cytometer. The results of an example of this assay are summarized in FIG. 9.

For the positive control, known amounts of anti-collagen-V anti-sera were added to the bead assay. As panels A, B, C, D, and E of FIG. 9 illustrates, increased amounts of anti-collagen V antibodies results in a significant shift to the right of the mean fluorescent channel. Thus, this method can detect different amounts of antibodies present in a patient's serum. Referring still to FIG. 9, panels F, G, H, I, J, and K illustrate the detection of anti-collagen V antibodies from the serum of four patients compared to serum samples obtained from healthy human subjects. As illustrated by the traces, a sample from patient #457 shows the largest shift to the right, suggesting that this patent has the highest level of anti-collagen V antibodies. Patients #458 and 420 show small shifts indicative of lower levels of antibody than patient #457, whereas, patient 519 does not appear to have any antibodies which react in this assay.

As shown by the results summarized in FIG. 9, patient #457 shows the largest shift to the right suggesting that this particular patient has the highest level of anti-col(V) antibodies. In contrast, samples collected from patients #458 and #420 illustrate only small shifts in fluorescent's peak; whereas, patient #595 does not appear to have any antibodies at all in this particular sample. These data are illustrative of a method for detecting the presence idiopathic pulmonary disease (IPD) or other autoimmune based lung disorder or disease and/or assessing the likelihood that a given patient undergoing a lung transplant will likely reject the transplanted organ. This method of diagnosing lung disease or assessing a given patient's likelihood of developing BOS generally involves collecting a sample of bodily fluid, for example, sera or interstitial fluid or tissue from the patient and analyzing the sample for the presence of antibody to Type V collage.

Example 4

Induction of Oral Tolerance, in test animals, a model for modulating a human or animal patient's autoimmune response to collagen or an antigenic component of collagen. Pathogen-free, MHC (RT1)-incompatible male rats utilized were: Fischer 344 (F344, $RT1^{1v1}$), Brown Norway (BN, $RT1^n$), and Wistar Kyoto (WKY, $RT1^1$) rats (250-300 g) at the time of transplantation, purchased from Harlan Sprague Dawley (Indianapolis, Ind.) or Taconic (Germantown, N.Y.) and housed in the Laboratory Animal Resource Center at Indiana University School of Medicine (Indianapolis, Ind.) in accordance with institutional guidelines.

Briefly, Type V collagen was prepared as follows. Purified human Type V collagen [col(V)] was diluted in 0.005M acetic acid (0.5 mg/ml) and stored at 4° C. until it was used in the assay. The quantity of col(V) was assessed by determination of the hydroxyproline content in the samples (Woessner, 1961).

In this particular test Type V Collagen was administered orally to WKY male rats. The animals (180-200 g) were fed with either 10 μg or 50 μg of col(V), col(II) or col(XI) solution dissolved in 0.5 ml of saline by a gastric gavage utilizing a 16-gauge ball-point stainless steel animal feeding needle (Braintree Scientific, Braintree, Mass.) as previously described (Stark and Ostrow, 1990). As a control similar animals were fed with diluent alone. Animals were fed every other day, for either eight or four feedings. Seven days after the last feeding, these rats received F344 lung allografts by orthotopic transplantation. WKY lung grafts transplanted into WKY recipients (isografts) were used as controls.

Delayed-type Hypersensitivity (DTH) responses were determined by a modification of procedures described by Sayegh, et al., 1992; Yoshino, et al., 1995; and Yamagami, et al., 1999. In brief, two weeks post-lung transplantation, control or col(V)-fed WKY rats received $10^7$ irradiated (3000 rad) donor-derived F344 or third party (BN) splenocytes in 30 μl of PBS into the right pinnae by subcutaneous (s.c.) injection using a 26 gauge needle. The left pinnae received an equal volume of diluent to serve as the control site. A separate group of nave or allograft recipient WKY rats were tested with 15 μg of col(V) in 30 μl volume injected into the right pinnae and diluent into the left. Naïve WKY rats were used as negative controls. The ear thickness was measured with a micrometer caliper (Mitutoyo, Field Tool Supply, Chicago, Ill.) in a blinded fashion immediately before and 24 hr after injection. Antigen-specific DTH response was calculated according to the following formula: specific ear swelling= (right ear thickness @ 24 hr–right ear thickness @ 0 hr)–(left ear thickness @ 24 hr–left ear thickness @ 0 hr)×10–3 mm (Yamagami, et al., 1999). All data reported as the mean of triplicate measurements.

The orthotopic transplantation of left lung isografts (WKY→WKY), or allografts (F344→WKY) was performed as previously reported (Sekine et al., 1997), utilizing a procedure initially described by (Marck et al., 1983 and Prop et al., 1985). Similar to the inventors' prior report (Sekine, et al., 1997), survival exceeded 90% in all transplantation groups. No immunosuppressive therapy was given at any time during the experimental period.

Transplanted lungs were monitored by serial chest radiographs on days 1, 6, and 13 post-transplantation. The radiographic changes were graded as follows: grade 1, normal; grade 2, mild infiltrates; grade 3, moderate infiltrates; and grade 4, severe infiltrates or complete opacification.

Five transplantation groups were studied: lungs from WKY rats transplanted into WKY recipients (WKY→WKY, control isografts); F344 lungs transplanted into diluent fed WKY recipients (F344→WKY, control allografts); F344 lungs transplanted into col(V)-fed WKY recipients (F344→col(V)-fed WKY, col(V)-fed allografts); F344 lungs transplanted into col(II)-fed WKY recipients (F344→col(II)-fed WKY, col(II)-fed allografts); and F344 lungs transplanted into col(XI)-fed WKY recipients (F344→col(XI)-fed WKY, col(XI)-fed allografts). Preliminary experiments demonstrated that diluent feeding had no effect on development of allograft pathology, bronchoalveolar lavage (BAL) differential cell counts, or DTH responses compared to allografts transplanted into unfed WKY rats.

BAL fluid was collected by ketamine-anesthetizing lung transplant recipients one and two weeks after transplantation. In brief, BAL of native and transplanted lungs were performed by selective cannulation of right and left mainstem bronchi with a 16-gauge catheter secured by suture. During a period of time in which the contralateral bronchus was clamped 3 ml aliquots of sterile PBS (37° C.) were instilled into each main stem bronchus and aspirated. Cell-free BAL supernatants obtained from centrifuged specimens was stored at −70° C. until it was used. BAL fluid differential cell counts were performed utilizing light microscopy to count 300 cells per high power field on cytospin preparations to determine the quantity of macrophages, lymphocytes, and polymorphonuclear (PMN) cells in the sample.

In order to detect the presence of pathology in the lungs, transplanted lungs from each group were harvested, fixed by an intratracheal instillation of 4% glutaraldehyde, sectioned, stained with hematoxylin and eosin, examined under light microscopy, and graded according to the histologic criteria established by the Lung Rejection Study Group (Yousem, et al., 1996) in a blinded fashion without prior knowledge of the transplantation group.

Statistical analyses of PMN and lymphocyte counts in BAL fluid were performed initially by ANOVA to determine if differences were present amongst the groups. If differences were found than a post hoc analysis utilizing a Student-Newman-Keuls test was performed to determine which group was different. P values<0.05 were determined to be significant. Since data for DTH in control allograft and nave WKY rats challenged with different antigens was found to be non-normally distributed, a rank-sum two-way ANOVA with interaction was utilized to determine differences amongst the groups. P values<0.05 were determined to be significant. Differences in DTH responses to donor alloantigens between control allografts and col(V)-fed allografts were determined utilizing a Mann-Whitney U test. P values<0.05 were determined to be significant. Differences between airway and vascular pathologic scores were determined initially utilizing the Kruskal-Wallis test followed by a post hoc analysis utilizing the Mann-Whitney U test. P values<0.03 were determined to be significant.

The inventors have previously shown that col(V) is a target of the local immune response to lung alloantigens in mice. Next they demonstrated that col(V) is recognized as an antigen during lung allograft rejection. DTH responses have been reported to correlate with the extent of rejection in various rodent models of organ transplantation other than the lung (VanBuskirk, et al., 1998; Lowry, et al., 1985; Joo, et al., 1995). As an in vivo test of the cellular immune response, the systemic DTH response to alloantigen was performed. The DTH responses to F344 splenocytes, col(V), and BN splenocytes (third party) in WKY rats two weeks after receiving F344 lung allografts and in nave, non-transplanted WKY rats was examined. FIG. 10 illustrates that WKY rats that received F344 allografts had significant DTH responses to F344 splenocytes [p<0.0001 compared to nave WKY rats tested with either F344 splenocytes or col(V)]. WKY rats that received F344 allografts also had significant DTH responses to col(V) [p<0.0001 compared to nave WKY rats tested with either F344 splenocytes or col(V)] (FIG. 11). Statistically, there were no differences between the DTH responses of control allografts to F344 splenocytes and col(V) (p>0.05). Data showing that WKY rats that received F344 lung allografts had no DTH response to third party alloantigens (BN splenocytes, RT1″) demonstrates that the immune response to F344 allografts is allo-specific. In addition these data are consistent with col(V) being recognized as an antigen during lung allograft rejection.

Prior reports have shown that oral administration of antigens that are targets of the immune response during rejection of allografts, other than the lung, induces tolerance to the donor organ (Ishido, et al., 1999). To determine if oral administration of col(V) to lung allograft recipients prior to transplantation induces immunological tolerance to the donor lung, WKY recipients were fed col(V) prior to transplantation as described above. Preliminary experiments demonstrated that eight feedings of 10 μg of col(V) every other day (total dose of 80 μg) followed by left orthotopic lung transplantation seven days after the last feeding had the greatest effect on the BAL cell counts and rejection pathology in this model. Therefore, this feeding regimen was utilized for all subsequent studies. Col(V)-fed recipients underwent left lung transplantation and were harvested at the completion of the experimental period as described above.

FIG. 12 illustrates the differential cell counts in BAL fluid from transplanted lungs of control WKY isograft recipients, control WKY allograft recipients, and col(V)-fed WKY allograft recipients two weeks post-transplant, and normal WKY rats. There were no differences in BAL differential cell counts in normal lungs as compared to isograft lungs. Similar to (Yagyu, et al, 1990), PMN's and lymphocytes were significantly increased in control allograft BAL compared to normal or isograft lungs (p<0.039 for PMN's and p<0.00001 for lymphocytes). In contrast, feeding col(V) prior to transplantation resulted in a significant reduction in BAL PMN's and lymphocytes compared to control allografts (p<0.023 for PMN's and p<0.0001 for lymphocytes). Acute allograft rejection is usually associated with an increase of total cell counts in allograft BAL fluid (Hirt, et al., 1999). However, at two weeks post-transplant, the control WKY allograft lungs are usually undergoing severe rejection and due to destruction of the allograft, sufficient BAL could not be performed reliably to determine BAL total cell counts. In contrast, col(V)-fed allograft recipients showed less severe rejection which allows easier BAL resulting in higher cell counts. For these reasons, comparison of total cell counts between the groups could not be done. Collectively, these data demonstrate that oral immunization with col(V) is associated with fewer PMN's and lymphocytes in allograft BAL fluid during acute rejection.

To determine if col(V) feeding diminished DTH responses to alloantigens, control WKY allograft recipients and col(V)-fed WKY allograft recipients were challenged in the right pinnae with whole allogeneic (F344) splenocytes and PBS in the left pinnae. The DTH response was measured 24 hr later and the specific ear swelling was determined. As shown in FIG. 10, untreated control WKY allograft recipients undergoing severe acute rejection had a strong DTH response after challenge with donor antigen. In contrast, the col(V)-fed WKY allograft recipients that had less severe allograft rejection also had a significant reduction of the DTH response to donor antigens.

The impaired immune response to alloantigen induced by col(V) could have been due to global immune hyporesponsiveness (Faria and Weiner 1999), and not tolerance. Therefore, to determine if col(V)-fed WKY rats could respond to other antigens, these rats received lipopolysaccharide (LPS) (Sigma, St. Louis, Mo.) either intratracheally (200 µg/kg to 1 mg/kg) or intravenously (1-5 mg/kg), which are doses known to induce severe inflammatory reactions in the lung and systemically 24 to 48 h after injection or instillation (Delclaux, et al. 1999). Rats were challenged one week after their last feeding of col(V). The disease induced is analogous to pneumonia and sepsis caused by gram-negative bacteria. Similar to normal WKY rats, instillation of LPS into lungs or injected I.V. into col(V)-fed WKY rats induced severe illness (ruffled fur and prostration) and inflammation in recipient lungs. These data show that feeding col(V) prior to transplantation prevented allograft rejection by inducing tolerance, and not global immune hyporesponsiveness, to donor antigens.

Collectively, these data illustrate that col(V), but not col(II) or col(XI), down-regulates lung allograft rejection by induction of oral tolerance and not global immune hyporesponsiveness. Furthermore, oral tolerance induced by col(V) down-regulates DTH responses to donor alloantigens.

Diminished PMN and lymphocyte counts in allograft BAL fluid are associated with less severe radiographic and histologic lesions during acute lung allograft rejection. To determine the rate of progression of lung infiltrates, transplant recipients were monitored by serial chest radiographs on days 1, 6, and 13 post-transplantation and graded as described above. Control isografts did not have any pulmonary infiltrates at all monitored time points (FIG. 12A). In the control allografts serial x-rays revealed gradual development of infiltrates in the left lung at 6 days post-transplant which resulted in severe infiltrates and complete opacification of the allograft by the end of the second week (FIG. 12B). However in col (V)-fed allografts the development of infiltrates was much slower compared to controls. The x-rays were normal at day 6 and only mild infiltrates were present at two weeks post-transplantation (FIG. 12C).

Referring now to FIG. 13 the upper panels of show the gross anatomy of the native and isograft WKY lungs, and the native and allograft lungs from control allograft and col(V)-fed allograft rats harvested at two weeks post-transplantation. FIG. 13A shows that the isograft (left-L) and the native lung (right-R) of WKY rat recipient are normal in appearance. In contrast, the left allograft lung in the control allograft group was dark brown in color, shrunken, and of a firm consistency compared to the native lung (FIG. 13B). As a result of inflammation and rejection, fusion of the parietal and visceral pleura was usually observed in control allograft lungs. The transplanted left lung in col(V)-fed allograft recipients (FIG. 13C) had the appearance of the native (normal) or isograft lung (FIG. 13A) and no pleural adhesions.

Fewer PMN's and lymphocytes in allograft BAL fluid, less severe infiltrates in the allografts on chest x-ray, and preserved gross anatomy suggested that feeding col(V) prior to transplantation down-regulated development of rejection pathology. The photomicrographs of the lower panels of FIG. 14 show the representative histology of control isografts, control allografts, and col(V)-fed allografts two weeks post-transplantation. Similar to a prior report (Prop, et al., 1985), all control isograft lungs had normal histology without signs of rejection (FIG. 14D). Control allografts revealed extensive perivascular, peribronchial, and alveolar mononuclear cell infiltrates consistent with severe acute rejection (FIG. 14E). In contrast, only mild to moderate perivascular and peribronchial infiltration were detected in the col(V)-fed allograft lungs (FIG. 14F).

Table 3 in FIG. 15 shows the grading of rejection pathology at two weeks post-transplantation using standard criteria. Acute vascular rejection was graded in A0-A4 according to the presence and extent of perivascular mononuclear cell infiltrates, and acute airway rejection graded B0-B4 according to the extent and intensity of airway inflammation (Yousem, et al. 1996). All isograft control lungs revealed normal structure of the lung (A0±0, B0±0). The control WKY allografts had severe vascular and airway rejection (A3.8±0.2, B4.±0.0, respectively). In contrast, col(V)-fed WKY allografts showed mild to moderate vascular and airway rejection (A2.8±0.2, B2.6±0.2, respectively). Col(II) and col(XI) fed allografts had rejection pathology similar to untreated allografts (FIG. 15). These data show that col(V)-fed WKY allografts had less severe rejection pathology than all other allografts ($p<0.028$ for A scores and $p<0.009$ for B scores).

These data show that feeding col(V) down-regulates lung allograft rejection indicating that orally tolerized lung allograft recipients should have a diminished DTH response after re-challenge with donor alloantigens. To determine if col(V) feeding diminished immune responses to alloantigens, control allograft recipients and col(V)-fed allograft recipients were challenged in the right pinnae with whole allogeneic F344 splenocytes and PBS in the left pinnae. The DTH response was measured 24 hr later and the specific ear swelling was determined. As shown in FIG. 14, untreated control allograft recipients undergoing severe acute rejection had a strong DTH response after challenge with donor antigen (same data for control allografts shown in FIG. 10). In contrast, the col(V)-fed allograft recipients had a significantly reduced DTH response to donor antigen ($p<0.02$ compared to control allograft). These data indicate that feeding col(V) prior to transplantation prevented allograft rejection by inducing tolerance to donor antigens.

Two weeks post-transplantation, the time of onset of severe rejection (grade 4), allograft lungs underwent BAL for determination of differential cell counts, and collection of serum. Native and transplant lungs were harvested en bloc, fixed, sectioned, stained, and graded for rejection pathology using standard criteria (Yousem, et al. 1996). All interpretations and grading of rejection pathology were performed by Oscar W. Cummings, M.D., pulmonary pathologist, who was blinded to the treatment groups, as previously reported (Wilkes, et al. 1998). FIG. 14 shows the gross anatomy of isograft WKY lungs and the native and allograft lungs from control WKY allografts, and col(V)-fed WKY allograft recipients harvested at two weeks post-transplantation. In control WKY allograft animals, FIG. 14B shows that the transplanted (left) lung was dark brown in color, and shrunken compared to the native lung. In contrast, the transplanted left lung in col(V)-fed WKY allograft recipients (FIG. 14C) had the appearance of the native (normal) or isograft lung (FIG. 14A). The gross appearance of allografts lungs in WKY rats fed col(II), or col(XI) was similar to untreated allograft lungs. As expected, isograft lungs appeared normal (FIG. 14A).

FIG. 14 also illustrates histology of control WKY isografts, control WKY allografts, and col(V)-fed WKY allografts two weeks post-transplantation. WKY isograft lungs had normal histology (FIG. 14D). Control WKY allografts revealed extensive perivascular, peribronchial, and alveolar mononuclear cell infiltrates consistent with severe acute rejection (FIG. 14E). In contrast, only mild to moderate perivascular and peribronchial infiltration were detected in the col(V)-fed WKY allograft lungs (FIG. 14F). Allografts lungs in WKY rats fed col(II) or col(XI) had pathology similar to untreated allograft lungs (see FIG. 15).

Although, oral tolerance has been shown to be of benefit in down-regulating alloreactivity in organs other than the lung (Ishido, et al., 1999), oral tolerization in lung transplantation was first reported in Wilkes U.S. patent application Ser. No. 10/243,797, filed Sep. 13, 2002. Utilizing a rat model of lung transplantation, data in the present invention show that oral administration of col(V) to lung allograft recipients prior to lung transplantation down-regulates rejection responses. Immunological, radiological, and histological analysis of col (V)-fed compared to control allograft recipients show that feeding col(V) is associated with diminished PMN and lymphocyte counts in allograft BAL fluid, less severe infiltrates in the allografts on chest x-ray, preservation of gross anatomy of the allograft, and reduction of rejection pathology. Finally, orally tolerized allograft recipients have diminished DTH responses to donor alloantigens.

It has been shown previously that col(V) is a target of the local immune response to alloantigens in mice. Type (V) Collagen is a minor type collagen present in the lung, located in the peribronchiolar connective tissues, alveolar interstitium, and capillary basement membrane. These tissues have been shown to be sites of pathologic lesions in response to alloantigens in the inventors murine model (Wilkes, et al., 1999) and are sites of rejection activity in human lung allograft recipients (Trulock, 1997).

Oral administration of antigens is an effective method of inducing peripheral T-cell tolerance. This phenomenon often referred to as oral tolerance; has been well studied in various models of autoimmune diseases in animals including encephalomyelitis, uveitis, diabetes, myasthenia gravis, and arthritis. However, the mechanisms for inducing tolerance are not completely understood. All of the known mechanisms for tolerance induction, including clonal anergy, clonal deletion, and regulation by IL-4, IL-10, or TGF-β mediated active suppression may have a role in oral tolerance (Faria and Weiner, 1999). Generally, higher doses of antigen are reported to induce anergy or clonal deletion (Chen, et al., 1995; Whitacre, et al., 1991), whereas low doses induce cytokine regulation and active suppression (Faria and Weiner, 1999; Chen, et al., 1994). In the animal model of cardiac transplantation, oral administration of allogeneic splenocytes has been shown to be effective in tolerance induction by bypassing Th1 activation and selectively stimulating induction of Th-2 derived inhibitory cytokines such as IL-4 (Ishido, et al., 1999).

Inbred, pathogen-free, MHC (RT1)-incompatible male F344 (RT1$^{1v1}$) and WKY (RT1$^1$) rats (250-300 g) were utilized for transplantation surgery. All rats were purchased from Harlan Sprague Dawley (Indianapolis, Ind.). The orthotopic transplantation of left lung allografts was performed as previously reported (Sekine, et al. 1997), and utilized a procedure described by Marck and colleagues (1983). No rats receive any immuno-suppression. Rejection pathology was graded at various time points post-transplantation. The F344→WKY transplant model is associated with development of mild acute rejection (grade 1) by the end of the first week, moderate to severe rejection (grade 2-3) by the end of the $2^{nd}$ week, and severe—grade 4 rejection by the end of the $3^{th}$ week post-transplantation (Matsumura, et al. 1995). In addition, the F344→WKY model is the only animal model of lung transplantation that develops bronchiolitis obliterans (BO) reproducibly (Hirt, et al. 1999). Therefore, this model offers the unique opportunity to study the pathogenesis of acute and chronic rejection.

Different feeding regimens were tested to observe any differences in the induction of oral tolerance. Data show that the multiple feedings of low dose of col(V) (10 μg) were more suppressive of rejection episodes compared to higher doses (50 μg). Thus, in the model of oral tolerance used herein, regulation by Th2 cytokines (IL-4, IL-10) or activated suppression mediated by TGF-β also appears to play an important role in tolerance induction.

The induction of transplantation tolerance has become a major goal of transplant research, and over the years different techniques have been utilized to induce transplantation tolerance. Donor specific blood transfusion (Zheng, et al., 1999), bone marrow transplantation (Huang, et al., 2000), thymic injection of allogeneic cells (Garrovillo, et al., 1999), or systemic immunization with donor MHC derived peptides (Sayegh and Krensky, 1996) have been shown to induce transplantation tolerance in various animal models. However, these techniques would have limited utility in the potential lung allograft recipient due to the fact that the donor cells utilized for tolerance induction would not be available in sufficient time to induce tolerance prior to transplantation. In experimental autoimmune models of low dose oral tolerance, regulatory cells following oral tolerization are triggered in an antigen-specific fashion but suppress in an antigen nonspecific fashion. Therefore, it may not be necessary to identify the target auto-antigen itself, but it might suffice to orally administer a protein capable of inducing regulatory cells that secretes suppressive cytokines (Faria and Weiner, 1999). The model of oral tolerance in lung transplantation used herein shows that orally administered col(V), which is not donor-specific, is capable of suppressing alloreactivity and inducing transplantation tolerance. The inventors envision that the oral treatment of transplant recipients with col(V) prior to transplantation will provide therapy for preventing rejection in lung transplantation and for treating diseases known or thought to be caused by an autoimmune reaction to Type V collagen and or antigenic components thereof. For additional discussion of the results, reported in examples 4 thru 10 including figures and references cited therein the reader is directed to U.S. patent application Ser. No. 10/243,792 filed on Sep. 13, 2002, to Wilkes, which is now U.S. Patent Publication No. 2003/0078208 A1, which is herein incorporated by reference in its entirety.

Example 5

Elucidation of Additional MHC-"like" Peptides and Collagens useful for the Prevention of Allograft Rejection and to Tolerize Animals to Collagens and collagen-like molecules. Pathogen-free, MHC (RT1)-incompatible male rats were utilized for the study: Wistar Kyoto (WKY, RT1$^1$), Fischer 344 (F344, RT1$^{1v1}$), and Brown Norway (BN, RT1$^n$) rats (250-300 g at the time of transplantation). All rats were purchased from Harlan Sprague Dawley (Indianapolis, Ind.) and housed in the Laboratory Animal Resource Center at Indiana University School of Medicine (Indianapolis, Ind.) in accordance with institutional guidelines.

Collagen type II [col(II)] for use in the experiment was isolated from canine cartilage as previously reported (Mayes, et al. 2000), or purchased from Collaborative Biomedical Products, (Bedford, Mass.). Both preparations were solubilized in 0.005M acetic acid and dialyzed to yield a final concentration of 0.5 mg/ml.

Bovine collagen type XI [col(XI)] from fetal calf cartilage (Morris and Bachinger 1987) was purchased from Biogenesis, Sandown, N.H., and diluted in 0.005M acetic acid (0.5 mg/ml) and stored at 4° C. until it was used.

Human type V collagen [col(V)], extracted from human placenta and purified by differential NaCl precipitation (Mares, et al. 2000), was a gift from Dr. Jerome Seyer (VA Hospital, Hampton, Va.). In brief, placental tissues were minced, washed, and suspended in 0.5 M acetic acid containing 0.5 M NaCl, and digested by pepsin at 4° C. Supernatants were aspirated from centrifuged specimens, the pellet collected and the extraction procedure repeated. The supernatants were combined from the two digests, and col(V) was purified from the supernatants by differential NaCl precipitation from 0.5 M acetic acid (Mayes, et al. 2000). The intact col(V) was diluted in 0.005M acetic acid (0.5 mg/ml) until use. The quantity of collagens was assessed by determination of the hydroxyproline content in the samples as previously reported (Mares, et al. 2000).

Collagen as prepared in the above was administered orally to WKY rats. The rats were fed with 10 µg of col(II), col(V), or col(XI) dissolved in 0.5 ml of saline by a gastric gavage utilizing a 16-gauge ball-point stainless steel animal feeding needle (Braintree Scientific, Braintree, Mass.). Control animals were fed with diluent alone. Animals were fed every other day for eight feedings. Seven days after the last feeding, these rats were utilized as recipients of lung allografts (described below).

The orthotopic transplantation of left lung isografts (WKY→WKY), or allografts (F344→WKY) was performed as previously reported (Sekine, et al. 1997), utilizing a procedure previously described, and (Prop, et al. 1985). In brief, after the donor rats (F344 or WKY) were anesthetized with an i.m. injection of ketamine (40 mg/kg) and xylazine (5 mg/kg), the chest was shaved, sternotomy incision made, and the heart and lungs were removed en bloc. The left lung was than resected and heparinised Lactated Ringer's solution was infused into the pulmonary artery. The donor lung was wrapped in sterile gauze saturated with saline and placed on ice (4° C.) in a sterile beaker until transplantation.

Recipient rats were anesthetized with an s.c. injection of atropine (0.05 mg/kg), followed by an inhalation of 2% halothane. The airway was cannulated with a 14-gauge Teflon catheter and the rat was mechanically ventilated using a rodent ventilator (Analytical Specialties Co., St. Louis, Mo.) utilizing 100% oxygen, and the inhalation of 1.5-2% isoflurane for maintenance anesthesia. Once a thoracotomy incision was made in the left 4th intercostal space, and hemostats placed on the left pulmonary vessels and bronchus, the left lung was resected. The pulmonary vessels of the donor lung were anastomosed to the recipient by a plastic cuff and 7-0 silk sutures (Kono, Chiba, Japan). The donor and recipient bronchi were sutured together utilizing 8-0 Prolene sutures (Ethicon, Sommerville, N.J.). Immediately after completion of the anastomosis of the bronchus, the hemostat was removed and ventilation was restored. After the left thoracotomy incision was closed over a 16-gauge chest tube utilizing 3-0 silk suture (Ethicon), maintenance anesthesia was discontinued and the animal was allowed to recover. Once spontaneous respiration resumed, the cannula was removed from the airway, and the chest tube removed. The ischemic time of the donor lung was approximately 1 h and the total operating time for harvesting and transplanting the donor lung was approximately 2 h. All transplantation procedures were performed by K. Y. under a surgical microscope (Micro Tech, Colorado Springs, Colo.) under sterile conditions. The F344→WKY transplant model is associated with the development of mild acute rejection by the end of the first week and moderate to severe acute rejection by the end of the second week (Matsumura, et al. 1995). Survival exceeded 90% in all transplantation groups. No immunosuppressive therapy was given at any time during the experimental period.

Transplanted lungs were monitored by serial chest radiographs on days 1, 6, and 13 post-transplantation. The radiographic changes were graded as follows: grade 1, normal; grade 2, mild infiltrates; grade 3, moderate infiltrates; and grade 4, severe infiltrates or complete opacification.

Five transplantation groups were studied: lungs from WKY rats transplanted into WKY recipients [control isografts]; F344 lungs transplanted into diluent fed WKY recipients [control allografts]; F344 lungs transplanted into col(V)-fed WKY recipients [col(V)-fed allografts]; F344 lungs transplanted into col(II)-fed WKY recipients [col(II)-fed allografts]; and F344 lungs transplanted into col(XI)-fed WKY recipients [col(XI)-fed allografts].

Bronchoalveolar lavage (BAL) fluid was collected from ketamine-anesthetized lung transplant recipients two weeks after transplantation as previously reported (Sekine, et al. 1997). In brief, BAL of native and transplanted lungs were performed by selective cannulation of right and left mainstem bronchi with a 16-gauge catheter secured by suture. The sample was collected while clamping the contralateral bronchus, 3 ml aliquots of sterile PBS (37° C.) were instilled into each main stem bronchus and aspirated. Cell-free BAL supernatants obtained from centrifuged specimens was stored at −70° C. until it was used. BAL fluid differential cell counts were performed utilizing light microscopy to count 300 cells per high power field on cytospin preparations to determine the quantity of macrophages, lymphocytes, and polymorphonuclear (PMN) cells.

Delayed-Type Hypersensitivity (DTH) responses were determined by a modification of a procedure described by (Yamagami, et al. 1999). In brief, two weeks post-lung transplantation, control or col(V)-fed WKY rats received 107 irradiated (3000 rad) donor-derived F344 or third party (BN) splenocytes in 30 µl of PBS into the right pinnae by s.c. injection using a 26 gauge needle. The left pinnae received an equal volume of diluent, and served as the control site. Naïve WKY rats were negative controls. A separate group of nave or allograft recipient WKY rats were tested with 15 µg of col(II), col(V), or col(XI) in 30 µl volume injected into the right pinnae and diluent into the left. The ear thickness was measured with a micrometer caliper (Mitutoyo, Field Tool Supply, Chicago, Ill.) in a blinded fashion immediately before and 24 h after injection. Antigen-specific DTH response was calculated according to the following formula: Specific Ear Swelling=(right ear thickness @ 24 h−right ear thickness @ 0 h)−(left ear thickness @ 24 h−left ear thickness @ 0 h)×10$^{-3}$ mm (Yamagami, et al. 1999). All data reported as the mean of triplicate measurements.

In separate experiments, nave and col(V)-fed WKY rats were primed with 100 µg of low endotoxin bovine serum albumin (BSA) (Sigma, St. Louis, Mo.) dissolved in 100 µl of an emulsion of adjuvant (Titermax, CytRx Corp., Norcross, Ga.). Each rat was primed s.c. with the emulsion at the base of the tail. Seven days later rats were challenged with 2% heat aggregated BSA solution into the right pinnae and diluent into the left (Henningsen, et al. 1984). Unprimed rats were controls for these studies. The ear thickness was measured immediately before and 24 h after injection and the Specific Ear Swelling calculated as described above.

Neutralization of TGF-β at the DTH site was performed by a modification of a procedure described by (Bickerstaff, et al. 2000). In brief, two weeks post-lung transplantation, col(V)-fed WKY rats received 107 irradiated (3000 rad) donor-derived F344 splenocytes mixed with 5 µg of polyclonal chicken anti rat TGF-β Ab, or 5 µg of polyclonal goat anti rat IL-4 or IL-10 Ab (all R&D Systems, Minneapolis, Minn.) in 30 µl of PBS into the right pinnae by s.c. injection using a 26 gauge needle. The left pinnae received an equal volume of diluent, and served as the control site. For negative controls, a separate group of col(V)-fed allografts received 10$^7$ irradiated (3000 rad) donor-derived F344 splenocytes mixed with 5 µg of control chicken immunoglobulins or control goat immunoglobulins (R&D Systems, Minneapolis, Minn.) into the right pinnae and diluent into the left. The Specific Ear Swelling was determined as described above. Control immunoglobulins had no effect on the DTH response.

As a model of acute lung injury alveolar or intravenous instillation of lipopolysaccharide (LPS) (Sigma, St. Louis, Mo.) was performed by a modification of a procedure described by (O'Leary, et al. 1997). Briefly, normal WKY rats or col(V)-fed WKY rats, one week after last feeding, were anesthetized with a s.c. injection of atropine (0.05 mg/kg), followed by an inhalation of 2% halothane. The airway was cannulated with a 14-gauge Teflon catheter and the rat was mechanically ventilated with a rodent ventilator (Analytical Specialties Co., St. Louis, Mo.) utilizing 100% oxygen, and the inhalation of 1.5-2% isoflurane for maintenance anesthesia. After disappearance of spontaneous respiration, LPS (1 mg/kg at 1 mg/ml) was instilled into the airway and mechanically ventilated for 10 minutes. Maintenance anesthesia was discontinued and the animal was allowed to regain consciousness. Once spontaneous respiration resumed, the cannula was removed from the airway. In separate experiments, rats were injected intravenously into the tail veins with LPS (4 mg/kg at 1 mg/ml). 24 h after challenge, BAL was performed and the lungs were harvested for assessment of pathology.

TGF-β levels in serum of the experimental groups were quantitated by ELISA utilizing the TGF-$β_1$ immunoassay system (Promega, Madison, Wis.) per manufacture's protocol. IL-4 and IL-10 levels in serum were quantitated by ELISA utilizing Cytoscreen immunoassay kits (BioSource International, Camarillo, Calif.) per manufacture's protocol. The sensitivity of the TGF-β, IL-4, and IL-10 assays were 32, 2, and 5 pg/ml, respectively.

Pathology was assessed by examining native and transplanted lungs from each group. Lung samples were harvested, fixed, sectioned, stained, and graded for rejection pathology using standard criteria (Yousem, et al. 1996) by a pathologist (O. W. C.) in a blinded fashion without prior knowledge of the transplantation group as previously reported (Sekine, et al. 1997).

Statistical analyses of PMN and lymphocyte counts in BAL fluid were performed initially by ANOVA to determine if differences were present amongst groups. If differences were found than a post hoc analysis utilizing a Student-Newman-Keuls test was performed to determine which group was different. P values<0.05 were determined to be significant. Since data for DTH in control allograft and nave WKY rats challenged with different antigens was found to be non-normally distributed, a rank-sum two-way ANOVA with interaction was utilized to determine differences amongst groups. P values<0.05 were determined to be significant. Differences in DTH responses to donor alloantigens between control allografts and col(V)-fed allografts were determined utilizing a Mann-Whitney U test. P values<0.05 were determined to be significant. Differences between airway and vascular pathologic scores were determined initially utilizing the Kruskal-Wallis test followed by a post hoc analysis utilizing the Mann-Whitney U test. P values<0.03 were determined to be significant. The Student's t test for multiple comparisons was utilized for analysis of cytokines. P values<0.05 were determined to be significant.

DTH responses to donor antigens, an in vivo test of cellular immunity, have been reported to correlate with the extent of rejection in various rodent models of organ transplantation other than the lung (VanBuskirk, et al. 1998; Lowry, et al. 1985). The present inventor has reported that col(V) is a target of the local immune response to lung alloantigens in mice (Mares, et al. 2000). Therefore, it was determined that the systemic DTH response to alloantigen in nave rats and lung allograft recipients to determine if col(V) is recognized as an antigen during lung allograft rejection. It was also determined whether lung allograft recipients develop a DTH response to col(V). DTH responses to F344 (donor) splenocytes and col (V) were examined in WKY rats two weeks after receiving F344 lung allografts, the time at which severe acute rejection begins to develop (Matsumura, et al. 1995), and in nave, non-transplanted WKY rats. To determine the specificity of the DTH response to alloantigens and col(V), DTH responses to col(II), col(XI), and third party antigens, BN splenocytes were determined. Col(II), a major component of the articular cartilage, is not present in the lung, and is not homologous to col(V) (Smith, et al. 1985). In contrast col(XI) has homology to col(V) (Morris and Bachinger 1987), but similar to col(II), it is found in articular cartilage and is not present in the lung. For these reasons, col(II) and col(XI) served as controls for col(V).

Utilizing Specific Ear Swelling as a measurement of DTH responses, FIG. 10 shows that control allograft recipients developed significant DTH responses to F344 splenocytes and col(V) two weeks post-transplantation [†$p<0.0001$ compared to nave WKY rats challenged with F344 splenocytes or col(V), and †$p<0.0001$ compared to nave WKY rats challenged with col(V) or F344 splenocytes] (FIG. 10). In contrast, control allografts did not have DTH responses to third party (BN) antigens, col(II), or col(XI) (FIG. 8). Naïve WKY rats did not have DTH responses to col(II), or col(XI). These data confirm other studies showing that DTH responses are indicative of immune activation during allograft rejection, which is specific to donor, but not third party alloantigens (VanBuskirk, et al. 1998). In addition, it confirms the present inventor's results in mice (Mares, et al. 2000) that col(V), but not col(II) or col(XI), is a target of the immune response to lung alloantigens.

Prior reports have shown that oral administration of antigens that are targets of the immune response during rejection of allografts, other than the lung, induces tolerance to the donor organ (Ishido, et al. 1999). To determine if oral administration of collagens to lung allograft recipients prior to transplantation induces immunological tolerance to the donor lung, WKY recipients were fed col(II), col(V), or col(XI) prior to transplantation as described above, followed by an assessment of serial chest x-rays, allograft BAL differential cell counts, pathologic grading, and DTH responses to donor antigens.

FIG. 12 shows the differential cell counts in BAL fluid from the experimental groups two weeks post-transplantation, the time of onset of severe acute rejection (Matsumura, et al. 1995), and in normal WKY rats. There were no differences in BAL differential cell counts in normal compared to isograft lungs. Similar to prior reports (Prop, et al. 1985; Yagyu, et al. 1990), PMN's and lymphocytes were significantly increased in control allograft BAL compared to normal or isograft lungs (*$p<0.00001$ for lymphocytes and †$p<0.038$ for PMN's compared to normal or isograft lungs) (FIG. 12). In contrast, feeding col(V) prior to transplantation resulted in a significant reduction in BAL PMN's and lymphocytes compared to control allografts (‡$p<0.0001$ for lymphocytes and §$p<0.023$ for PMN's compared to control allografts) (FIG. 12).

Acute allograft rejection is usually associated with an increase of total cell counts in allograft BAL fluid (Matsumura, et al. 1995). However, at two weeks post-transplant, the control WKY allograft lungs are usually undergoing severe rejection and due to destruction of the allograft, sufficient BAL could not be performed reliably to determine BAL total cell counts. In contrast, col(V)-fed allograft recipients show less severe rejection which allows easier BAL resulting in higher cell counts. For these reasons, comparison of total cell counts between the groups could not be done. Collectively, these data demonstrate that oral immunization with col(V) is associated with fewer PMN's and lymphocytes in allograft BAL fluid during acute rejection.

In acute lung allograft rejection diminished PMN and lymphocyte counts in allograft BAL fluid is usually associated with less severe radiographic and histologic lesions. To determine the rate of progression of lung infiltrates, transplant recipients were monitored by serial chest radiographs on days 1, 6, and 13 post-transplantation and graded as described above. As shown in FIG. 13, control isografts did not have any pulmonary infiltrates at all monitored time points (grade 1) (FIG. 13A). In the control allografts serial x-rays revealed gradual development of mild infiltrates (grade 2) in the left lung at 6 days post-transplant (data not shown), which resulted in severe infiltrates and complete opacification of the allograft (grade 4) by the end of the second week (FIG. 13B). However in col(V)-fed allografts, the development of infiltrates was much slower compared to controls. The x-rays were normal (grade 1) at day 6 and only mild infiltrates (grade 2) were present at two weeks post-transplantation (FIG. 13C).

The upper panels of FIG. 14 show the gross anatomy of the native and isograft WKY lungs, and the native and allograft lungs from control allograft and col(V)-fed allograft rats harvested at two weeks post-transplantation. The isograft (left-L) and the native lung (right-R) were normal in appearance (FIG. 14A). The transplanted lung in control allograft recipients was dark brown in color and shrunken compared to the native lung (FIG. 14B). In contrast, the transplanted left lung in col(V)-fed allograft recipients (FIG. 14C) had the appearance of the native (normal) or isograft lung (FIG. 14A).

Fewer PMN's and lymphocytes in allograft BAL fluid, less severe infiltrates in the allografts on chest x-ray, and preserved gross anatomy suggested that feeding col(V) prior to transplantation down-regulated development of rejection pathology. The lower panels of FIG. 14 show the representative histology of control isografts, control allografts, and col (V)-fed allografts two weeks post-transplantation. All control isograft lungs had normal histology without signs of rejection (FIG. 14D). Control allografts revealed extensive perivascular, peribronchial, and alveolar mononuclear cell infiltrates consistent with severe acute rejection (FIG. 14E). In contrast, only mild to moderate perivascular and peribronchial infiltration were detected in the col(V)-fed allograft lungs (FIG. 14F).

The data in FIG. 15 illustrates the grading of rejection pathology at two weeks post-transplantation. Acute rejection was graded A0-A4 according to the presence and extent of perivascular and interstitial mononuclear cell infiltrates, and B0-B4 according to the extent and intensity of the airway inflammation (Yousem, et al. 1996). All control isograft lungs revealed normal histology of the lung (A 0±0, B 0±0). The control allografts had severe vascular and airway rejection (A 3.8±0.2, B 4±0, respectively). In contrast, col(V)-fed allografts showed mild to moderate vascular and airway rejection (A 2.8±0.2, B 2.6±0.2, respectively) (*p<0.028 for A scores and $^\dagger$p<0.009 for B scores compared to control allografts) (FIG. 15, Table 3). Experiments showed that feeding col(II) or col(XI) had no effect on development of allograft pathology compared to control allografts (FIG. 15, Table 3). These data show that feeding col(V) down-regulated acute rejection pathology.

Data showing that feeding col(V) down-regulates lung allograft rejection suggested that orally tolerized lung allograft recipients should have diminished DTH responses to donor alloantigens. To determine if col(V) feeding diminished immune responses to alloantigens, control allograft recipients and col(V)-fed allograft recipients were challenged in the right pinnae with whole allogeneic F344 splenocytes and PBS in the left pinnae and DTH responses determined. As shown in FIG. 16 (and previously shown in FIG. 10), untreated control allograft recipients had a strong DTH response after challenge with donor antigen. In contrast, compared to control allograft recipients, the DTH response to donor antigen was reduced significantly in col(V)-fed allograft recipients (*p<0.02) (FIG. 16).

The impaired immune response to alloantigen induced by col(V) could have been due to global immune hyporesponsiveness (Faria and Weiner 1999), and not immune tolerance. Therefore, to determine if col(V)-fed WKY rats could respond to other antigens, these rats received LPS either intratracheally (1 mg/kg) or intravenously (4 mg/kg) which are doses known to induce severe inflammatory reactions in the lung and systemically 24 hrs after challenge (O'Leary, et al. 1997). The disease induced is analogous to pneumonia and sepsis caused by gram-negative bacteria. Similar to normal WKY rats, instillation of LPS into lungs or injected i.v. into col(V)-fed WKY rats induced severe illness (ruffled fur and prostration) and massive influx of PMN's and lymphocytes into the lung as observed in BAL differential cell counts and pathology (Data not shown).

In order to further investigate if the impaired immune response induced by col(V) feeding was antigen-specific, we determined if feeding col(V) affected DTH responses to an unrelated nominal antigen, BSA, a T-lymphocyte-dependent antigen in rats (Henningsen, et al. 1984). Naïve and col(V)-fed WKY rats were primed by s.c. injection of 100 μg of BSA in adjuvant and seven days later challenged with 2% heat aggregated BSA solution in the right pinnae and diluent in the left. DTH responses were determined 24 h after injection. Unprimed WKY rats served as controls for these studies. As shown in FIG. 24, injection of BSA into the pinnae of unprimed rats did not induce significant ear swelling. In contrast, injecting BSA into unfed primed WKY rats induced significant ear swelling (*p<0.018 compared to unprimed naïve WKY rats) (FIG. 19). However col(V) feeding did not affect the DTH responses to BSA $^\dagger$p>0.05 compared to primed WKY rats) (FIG. 24). Collectively, these data show that col(V)-induced suppression of lung allograft rejection is mediated by immune tolerance, and not global immune hyporesponsiveness.

Systemic production of TGF-β, IL-4, and IL-10 are cited frequently as cytokines responsible for suppressing immune responses in oral tolerance (Faria and Weiner 1999). Therefore, it was next determined if oral tolerance induced by col(V) is associated with up-regulated production of TGF-β, IL-4, and IL-10 during lung allograft rejection. Utilizing commercial ELISAs, TGF-β, IL-4, and IL-10 were quantitated in serum of the experimental groups. FIG. 17 shows that serum TGF-β levels in normal WKY rats, control allografts, and col(V)-fed allografts two weeks post-transplantation. As expected, low levels of TGF-β were present in the serum of normal WKY rats (Ying and Sanders 1998). There was a slight increase of TGF-β in control allografts. In contrast, TGF-β levels were up-regulated markedly in serum of col (V)-fed allografts (*p<0.05 compared to control allograft recipients) (FIG. 17). Neither IL-4 nor IL-10 was detectable in serum of the same rats (data not shown).

Although IL-4 and IL-10 were not detected in the serum, this did not preclude their activity systemically in down-regulating cellular immune responses to donor alloantigens.

To determine whether TGF-β, IL-4, or IL-10 had a role in suppression of immune responses to alloantigens, we utilized neutralizing antibodies to these cytokines in the DTH assay to donor antigens. Utilizing a modification of a procedure reported by (Bickerstaff, et al. 2000), two weeks post-lung transplantation, col(V)-fed WKY rats received $10^7$ irradiated (3000 rad) donor-derived F344 splenocytes mixed with 5 μg of polyclonal anti TGF-β, Ab or 5 μg of polyclonal anti IL-4 or IL-10 Ab in PBS into the right pinnae. The left pinnae received an equal volume of diluent plus splenocytes, and served as the control site. For negative controls, a separate group of col(V)-fed allografts received control immunoglobulins with splenocytes into the right pinnae and an equal volume of diluent plus splenocytes into the left pinnae. As shown in FIG. 18 and previously shown in FIG. 10 and FIG. 16, untreated control allograft recipients had a strong DTH response after challenge with donor antigen which was reduced significantly in col(V)-fed allograft recipients. However, col(V)-fed allografts significantly recovered DTH responses when anti-TGF-β antibodies were mixed with donor splenocytes and injected into the pinnae of the ears [*$p<0.03$ compared to col(V)-fed allografts challenged with antigens mixed with control immunoglobulin] (FIG. 18). In contrast, mixing donor splenocytes with neutralizing antibodies to IL-4 or IL-10 was less effective in restoring DTH responses to donor antigens [†‡$p>0.05$ compared to col(V)-fed allografts challenged with antigens mixed with control immunoglobulin] (FIG. 18). The restoration of the DTH responses in col(V)-fed allografts with anti-TGF-β, anti-IL-4, and anti-IL-10 antibodies relative to control allografts was 75.7%, 24.3%, and 39.9%, respectively (FIG. 18).

Example 6

The Effect of Col(V) for Oral Tolerance on Development of Acute Lung Allograft Rejection is Dose Dependent. F344 (RT1$^{1v1}$) and WKY (RT1$^1$) male rats (200-250 g) are purchased from Harlan Sprague Dawley (Indianapolis, Ind.). All left lung allografts (F344) or isografts (WKY) are transplanted orthotopically into WKY recipients as previously described (Sekine, et al. 1997).

Referring now to FIG. 25, Table 4, which includes a summary of data collected in this example. Type V collagen was isolated from either human placenta from normal births, or normal lung tissue specimens obtained at the time of lung cancer resection. Gerald N. Smith Jr., Ph.D., with extensive expertise in collagen biochemistry, provided purified Type V collagen for these studies.

WKY rats are immunized with collagen prior to transplantation surgery using gastric gavage as reported in preliminary data and submitted manuscript. All rats are fed every other day for either 4 or 8 days as described in the table. Similar to preliminary data, after a one week recovery period post-feeding, the left lung of F344 rats (allografts) or WKY rats (isografts) is transplanted orthotopically into WKY recipients. No rats in this experiment received immunosuppressive drugs. Twenty rats are included in each feeding group for each collagen type. Referring now to FIG. 25, Table 4 includes an explanation of the experimental groups used in this example reported on herein.

Twenty four hours prior to end of a two week period post-transplantation, which is the time for severe rejection to develop (Matsumura, et al. 1995), 10 recipient rats are tested for DTH responses to donor antigens, followed by harvesting thoracic organs. BAL is performed on the native and allograft lung by selectively cannulating the right and the left mainstem bronchi, respectively, and instilling a total of 5 ml of PBS at 37° C. (Sekine, et al. 1997). Cell free BAL is obtained from centrifuged specimens and supernatants stored at −80° C. Blood is collected by vena cava and cardiac puncture, specimens centrifuged to separate serum, and stored at −80° C.

Delayed-Type Hypersensitivity (DTH) Responses studies are performed by injection of irradiated donor (F344) splenocytes into the right ear of WKY rats 24 hr prior to completion of the two week post-operative period as reported in preliminary data and manuscript (Yasufuku, et al. Submitted). Data is reported as "specific ear swelling". Preliminary studies have confirmed other reports showing that the maximal DTH response occur 24 hour after ear injection (Yamagami, et al. 1999), and, therefore, all DTH measurements will be performed 24 h post-ear injection. Preliminary studies confirmed that DTH testing has no effect on systemic cellular or humoral responses. By comparing the DTH responses to donor antigens in isograft and allograft control recipients compared to collagen-fed WKY rats, it can be determined if different doses of col(V) have differential effects on DTH response to donor antigens.

After euthanasia, the thoracic organs are removed en bloc and studied histologically. Briefly samples of the thoracic organs were fixed by intratracheal instillation of 4% glutaraldehyde, embedded in paraffin, sectioned at 5-7 μm, and stained with hematoxylin and eosin (H&E) for histologic studies by light microscopy. The histologic lesions are graded by standard histologic criteria for human lung allograft rejection (Yousem, et al. 1996) in a blinded manner. (Wilkes, et al. 1995). Acute rejection is characterized by varying intensity of perivascular and peribronchiolar mononuclear cells infiltrates (Yousem, et al. 1996). Since differences in cellular infiltrates between groups may be more subtle than accounted for in the accepted criteria of acute rejection, infiltrates will also be quantified by counting the perivascular and peribronchiolar mononuclear cells present on digitized H&E-stained tissue sections (cells/μm$^2$) utilizing Sigma Scan software (Jandel Scientific, Chicago, Ill.). The digitizing procedures are currently in use in our laboratories.

Cytotoxic T-lymphocytes have key roles in the pathogenesis of lung allograft rejection (Trulock 1997), and impaired cellular cytotoxicity has been shown to be a key mechanism by which oral tolerance prevents disease activity (Faria and Weiner 1999; Mayer 2000; Garside and Mowat 1997). To determine whether diminished rejection activity in col(V) tolerized lung allograft recipients is associated with impaired anti-donor cellular cytotoxicity, peripheral lymph node cells are isolated from normal F344 (donor) rats, loaded with $^5$Cr (New England Nuclear, Boston, Mass.), and placed in 96 well flat bottom plates (target cells, 5×103/well) in complete media. Effector cells (splenic T-lymphocytes from recipient-WKY rats in each group) are incubated in varying ratios with targets (E/T ratios of 1:1, 5:1, 10:1. and 100:1) at 37° C. for 4 hours. Pure splenic T-cells (>95% pure) are isolated utilizing anti-CD3 magnetic beads (Dynal Corp, Lake Success, N.Y.), and confirmed by flow cytometry. Cytotoxicity is determined by specific $^{51}$Cr release induced by effector cells in each E/T ratio compared to release from loaded target cells, alone.

Other investigators have confirmed that lung allograft rejection in rats and humans is associated with apoptosis in cells present in alveolar, vascular, and bronchiolar tissues, and that apoptosis is detected infrequently during allograft acceptance (Blankenberg, et al. 2000). It has also been previously shown that the local immune response to alloantigens includes induction of apoptosis in vascular endothelium and bronchiolar epithelium in mice. In addition, immunization with col(V), which induces anergy to donor antigens, prevents alloantigen-induced apoptosis in this model.

In order to determine the ability of col(V)-induced oral tolerance to prevent apoptosis in lung allografts, TdT-mediated dUTP Nick End Labeling (TUNEL) assay kits (In Situ Cell Death Detection Kit, Boehringer Mannheim, Indianapolis, Ind.) are utilized to detect apoptosis in lung allograft tissue sections two weeks post transplantation. The quantity of apoptotic cells in perivascular and peribronchiolar tissues is quantitated on digitized eosin-counterstained tissue sections using (cells/$\mu m^2$) utilizing Sigma Scan software (Jandel Scientific, Chicago, Ill.).

To determine production of IL-4, IL-10, TGF-$\beta$, CTGF, and nitric oxide, all potential mediators of immune suppression induced by col(V), as well as the time course of synthesis post-transplant, the dose of col(V) that is most effective in preventing rejection pathology is used to feed another group of rats. In brief, allograft control rats and col(V)-fed allograft recipients are sacrificed 2, 4, 6, 8, 10, 12, and 14 days post-transplantation, and serum levels of IL-4, IL-10, TGF-$\beta$ quantitated by ELISA (R&D Systems, Minneapolis, Minn.) per manufacturer's protocol (n=5 five rats at each time point). RNase protections assays (Pharmingen, San Diego, Calif.) are utilized to detect mRNA for these cytokines in peripheral lymph nodes and splenocytes. Controls are serum, lymph nodes and splenocytes from normal WKY rats.

CTGF levels in serum of control allografts, col(V) fed allografts, and normal rats are determined by ELISA by Dr. George Martin, Ph.D., Scientific Director of Fibrogen, San Francisco, Calif., the leading expert in the structure and function of CTFG. Northern blotting is utilized to detect mRNA for CTGF in peripheral lymph nodes, and spleen utilizing probes supplied by Dr. Martin. Protein and mRNA expression is assayed for at the same time points described for IL-4, IL-10, and TGF-$\beta$.

Nitric oxide levels in serum are detected at various time points described above in control allografts and col(V)-fed allografts at the various time points post-transplantation described above, as well as in normal WKY rats. Production of stable metabolic nitrites and nitrates in serum is determined by Greiss reaction utilizing spectrophotometric analysis of serum (Kallio, et al. 1997).

Example 7

The Effect of Dose of Col(V) for Oral Tolerance on Development of Chronic Lung Allograft Rejection (Bronchiolitis Obliterans). Pathogen-free, MHC (RT1)-incompatible male rats were utilized for the study: Fischer 344 (F344, RT1$^{1v1}$), Brown Norway (BN, RT1") and Wistar Kyoto (WKY, RT1$^1$) rats (250-300 g at the time of transplantation). All rats were purchased from Harlan Sprague Dawley (Indianapolis, Ind.) and housed in the Laboratory Animal Resource Center at Indiana University School of Medicine (Indianapolis, Ind.) in accordance with institutional guidelines.

Collagen type II [col(II)] was isolated from canine cartilage as previously reported. Purified human type V collagen [col(V)] and type XI collagen [col(XI)] was a gift from Dr. Jerome Seyer (VA Hospital, Hampton, Va.). Collagens were diluted in 0.005M acetic acid (0.5 mg/ml) and stored at 4° C. until its use.

WKY rats were fed orally with 10 $\mu$g of col(V) dissolved in 0.5 ml of saline by a gastric gavage utilizing a 16-gauge ball-point stainless steel animal feeding needle (Braintree Scientific, Braintree, Mass.) as previously reported. Control animals were fed with diluent alone. Animals were fed every other day for eight feedings. Seven days after the last feeding, these rats were utilized as recipients of lung allografts.

The orthotopic transplantation of left lung isografts (WKY→WKY), or allografts (F344→WKY) was performed as previously reported, utilizing a procedure initially described by (Marck, et al. 1983, and Prop, et al. 1985). The F344→WKY transplant model is associated with the development of severe acute rejection by the end of the second week. In addition, this model is the only animal model of lung transplantation that develops bronchiolitis obliterans (BO) reproducibly. Survival exceeded 90% in all transplantation groups. No immunosuppressive therapy was given at any time during the experimental period.

Three transplantation groups were studied: lungs from WKY rats transplanted into WKY recipients [control isografts]; F344 lungs transplanted into diluent fed WKY recipients [control allografts]; and F344 lungs transplanted into col(V)-fed WKY recipients [col(V)-fed allografts]. Recipients were sacrificed at two and 10 weeks post-transplantation.

Delayed-Type Hypersensitivity (DTH) responses were determined as above, by a modification of a procedure initially described by (Sayegh, et al. 1994, and Yamagami, et al. 1999). In brief, 10 weeks post-lung transplantation, control or col(V)-fed WKY rats received 107 irradiated (3000 rad) donor-derived F344 or third party (BN) splenocytes in 300 of PBS into the right pinnae by s.c. injection using a 26 gauge needle. The left pinnae received an equal volume of diluent, and served as the control site. Naïve WKY rats were negative controls. A separate group of nave or allograft recipient WKY rats were tested with 15 $\mu$g of col(II), col(V), or col(XI) in 300 volume injected into the right pinnae and diluent into the left. The ear thickness was measured with a micrometer caliper (Mitutoyo, Field Tool Supply, Chicago, Ill.) in a blinded fashion immediately before and 24 h after injection. The specific ear swelling was calculated according to the following formula: Specific Ear Swelling=(right ear thickness @ 24 h–right ear thickness @ 0 h)–(left ear thickness @ 24 h–left ear thickness @ 0 h).times.×10–3 mm. All data reported as the mean of triplicate measurements.

Neutralization of TGF-$\beta$ at the DTH site was performed as previously reported by a modification of a procedure described by (Bickerstaff, et al. 2000). In brief, 10 weeks post-lung transplantation, col(V)-fed WKY rats received 107 irradiated (3000 rad) donor-derived F344 splenocytes mixed with 5 $\mu$g of polyclonal chicken anti rat TGF-$\beta$ Ab (R&D Systems, Minneapolis, Minn.) in 30 $\mu$l of PBS into the right pinnae. The left pinnae received an equal volume of diluent, and served as the control site. For negative controls, a separate group of col(V)-fed allografts received 107 irradiated (3000 rad) donor-derived F344 splenocytes mixed with 5 $\mu$g of control chicken immunoglobulins or control goat immunoglobulins (R&D Systems, Minneapolis, Minn.) into the right pinnae and diluent into the left. The Specific Ear Swelling was determined as described above. Control immunoglobulins had no effect on the DTH response.

Mixed leukocyte reaction was performed by a modification of a procedure described previously. In brief, F344 splenocytes (stimulators) which were used as a source of antigen-presenting cells (APCs), were treated with mitomycin C (Sigma, St. Louis, Mo.) and cocultured in varying ratios with lymph node T1 lymphocytes (responders) from WKY rats ($3\times10^5$/well) in 200 $\mu$l of medium (RPMI, 2 mM L-Glutamine, $5\times10^{-5}$ M 2-mercaptoethanol, 100 U/ml penicillin, 100 $\mu$l/ml streptomycin, 10% heat-inactivated fetal calf serum) in 96-well, flat-bottom microtiter plates (Costar, Cambridge, Mass.). Eighteen hours before the completion of a 5 day incubation at 37° C. (5% $CO_2$), 1 µCi/ml of $^3$H (Amersham Corp., Arlington Heights, Ill.) was added to each well. Cultures were harvested with an automated cell harvester (Brandel, Gaithersburg, Md.) and analyzed in a liquid scintillation counter (Beckman, Arlington Heights, Ill.). Cellular proliferation was determined as the mean of counts per minute of [$^3$H] thymidine incorporation in triplicate cultures and reported as stimulation index. In separate experiments the same assay was performed using splenocytes from WKY rats of the experimental group as the stimulator and lymph node T lymphocytes from F344 rats as responders.

TGF-β levels in serum of the experimental groups were quantitated by ELISA utilizing the TGF-$β_1$ immunoassay system (Promega, Madison, Wis.) per manufacture's protocol. IL-4 and IL-10 levels in serum were quantitated by ELISA utilizing Cytoscreen immunoassay kits (BioSource International, Camarillo, Calif.) per manufacture's protocol. The sensitivity of the TGF-β, IL-4, and IL-10 assays were, respectfully 32, 2, and 5 pg/ml.

In order to assess pathology native and transplanted lungs from each group were harvested, fixed, sectioned, stained, and graded for rejection pathology using standard criteria by a pathologist (O. W. C.) in a blinded fashion without prior knowledge of the transplantation group as previously reported.

Since data for DTH in control allograft and naïve WKY rats challenged with different antigens was found to be non-normally distributed, a rank-sum two-way ANOVA with interaction was utilized to determine differences amongst groups. Differences in DTH responses to donor alloantigens between control allografts and col(V)-fed allografts were determined utilizing a Mann-Whitney U test. The Student's t test for multiple comparisons was utilized for analysis of MLR and cytokines. P values<0.05 were determined to be significant.

It has been demonstrated that acute lung allograft rejection is associated with immune response to donor antigens as well as col(V). However, recent studies have suggested that immune responses to donor antigens may diminish over time. To determine if immune response to donor antigens and col (V) are present long term after lung transplantation, DTH responses to F344 (donor) splenocytes and col(V) were examined in WKY rats 10 weeks after transplantation of F344 lung allografts. FIG. 19 shows that control allograft recipients have significant DTH responses to donor antigens (F344 splenocytes) and col(V) compared to nave WKY rats (*p<0.05). Significantly, the DTH responses to donor antigen and col(V) at 10 weeks were similar to that observed during acute rejection (two weeks post transplantation). Col(II) or col(XI) (controls) did not induce DTH responses in lung allograft recipients at either time point.

Oral tolerance induction using donor derived antigen has been effective in suppressing cellular immune responses to donor antigens up to two weeks post-transplantation. In addition, deficient antigen presentation has been reported to be another mechanism by which tolerance can modulates immune responses. It was next determined if feeding col(V) down regulated cellular immune responses to donor antigens long term, and examined the effect of col(V)-induced oral tolerance affected antigen presentation. As described above, unfed and WKY rats that were fed col(V) received F344 lung allografts. Two weeks (time of acute rejection) and ten weeks (time of onset of BO) post-transplantation, rats were sacrificed, lymph node lymphocytes isolated and stimulated with donor antigens (F344 splenocytes). FIG. 19 shows that lymph node lymphocytes from normal WKY rats or lymphocytes isolated from WKY rats two or ten weeks post-transplantation of F344 lung allografts had comparable proliferative responses to donor antigens. In contrast, compared to normal or control allografts, col(V)-induced oral tolerance caused significant reductions in proliferative responses to donor antigens at both time points (*p<0.05). In addition, proliferative responses to lymphocytes from col(V)-fed lung allograft recipients were less at 10 weeks compared to two weeks (*p<0.05, FIG. 20).

We next determined if col(V)-induced oral tolerance affected antigen presentation. In brief, splenocytes (source of antigen presenting cells) were isolated from normal WKY rats, or col(V)-fed WKY rats two and 10 weeks post-transplantation of F344 lung allografts, and examined for their ability to induce F344 lymph node lymphocytes to proliferate in a MLR. FIG. 19 shows that splenocytes isolated from col(V)-fed allograft recipients at two and ten weeks induced proliferation comparable to splenocytes isolated from normal WKY rats.

DTH responses to donor antigens have been reported to correlate with rejection activity in various rodent models of organ transplantation. Therefore, data showing diminished DTH responses to donor antigens in col(V)-fed lung allograft recipients at ten weeks suggested reduced rejection pathology in the allografts. FIG. 21 shows the gross anatomy and histology of lung allografts harvested from WKY rats that received F344 lung allografts (control allografts), and col(V)-fed WKY rats that received F344 lung allografts 10 weeks post-transplantation. Control allografts were dark brown, shrunken, and firm (FIG. 21A). In contrast, allografts from col(V)-fed WKY rats had a nearly normal appearance with only slight discoloration (FIG. 21B). At 10 weeks post-transplantation, all control allografts developed extensive interstitial mononuclear cell infiltrates, fibrosis, and obliteration of small airways by granulation tissue which are pathologic lesions of BO (n=5, FIG. 21C). In contrast, allografts harvested from col(V)-fed rats only had mild alveolar infiltrates, without interstitial inflammation which describes the pathology of mild acute rejection (grade A2, n=5, FIG. 21D).

Systemic production of IL-4, IL-10, or TGF-β has been reported commonly as the mechanism of oral tolerance-induced immune suppression. Serum levels of TGF-β in the three experimental groups. 10 weeks after transplantation are shown in FIG. 22. Normal WKY rats have low levels of TGF-β in serum, and a slight, but not significant, increased TGF-β levels in WKY rats that received F344 lung allografts (control allografts—FIG. 22). However, feeding col(V) prior to lung transplantation resulted in significantly increased serum levels of TGF-β (FIG. 25, *p<0.05). Feeding col(V), alone, without lung transplantation did not increase serum TGF-β levels (data not shown). Neither IL-4 nor IL-10 was detected in serum of any group.

Data showing down-regulation of lymphocyte responses to alloantigen and intact presentation of alloantigens in vitro, suggests that col(V)-induced oral tolerance should also be associated with suppressed DTH responses to donor antigens in vivo. As expected, FIG. 23 shows that control allograft recipients have strong DTH responses to donor antigens. However, feeding col(V) prior to transplantation results in significantly diminished DTH responses to donor antigens (FIG. 23, *p<0.05). To determine if increased serum levels of TGF-β was contributing to col(V)-induced oral tolerance, the DTH response to donor antigens was repeated using neutralizing antibodies to TGF-β as reported previously. FIG. 23 shows that neutralizing TGF-β resulted in a significant recovery of DTH responses to donor antigens (*p<0.05, and 75% of DTH response observed in control allografts).

Example 8

Referring now to FIG. 26, Table 5 lists the experimental groups used in Example 8, the determination of whether peptides present in cyanogen bromide digests of α-chains of Col(V) prevent the development of acute rejection, Briefly, these experimental groups are as follows: Allograft Control Intact col(V)-fed 2(V). Type V collagen is isolated from human lungs obtained at autopsy. After lung tissues are minced, washed, and suspended in 0.5 M acetic acid containing 0.2 M NaCl, and digested by pepsin, supernatants are aspirated from centrifuged specimens, the pellet collected and the extraction procedure repeated. The supernatants are combined from the two digests, and stored at −70 C. Type V collagen is purified from the supernatants by differential NaCl precipitation from 0.5 M acetic acid (Piez, et al. 1963). The cycle of solubilization in acetic acid and NaCl precipitation is repeated until a type V preparation with an α-chain ratio α1(V)/α2(V) of approximately 2 is obtained as determined by SDS-polyacrylamide gel electrophoresis (Woodbury, et al. 1989). Separation of α1(V) from α2(V) is achieved by chromatography on DEAE-cellulose (Chiang, et al. 1980). The α1(V) and α2(V) chains are eluted from the column, and quantified by determination of the hydroxyproline content in the effluent.

The α chains of collagen type V are further fractionated by digestion with cyanogen bromide, which cleaves the collagen at methionine residues (Miller, et al. 1971). On completion of digestion, the samples are diluted 50 fold and lyophilized to remove the cyanogen bromide. The extent of digestion is screened on polyacrylamide gels. Individual peptides are isolated by a combination of ion exchange and molecular sieve chromatography.

Twenty WKY rats received intact col(V), or pooled peptides from α1(V), or α2(V) by gastric gavage. The dosage and feeding regimen for intact col(V) or peptides in this Example are the same as determined for intact col(V) in Example 5. Two weeks post-transplantation, the rats in each group are sacrificed and lung harvested.

Example 9

The data presented herein suggest that the methods of the present invention will be effective to prevent or diminish acute or chronic rejection episodes in human transplant recipients similar, if not identical therapy, should also be an effective treatment for Idiopathic Lung Disease or any other type of lung disease or disorder that involves an autoimmune response to collagen found in the lungs. It is contemplated that when a human subject is placed on a list to receive a transplant, the subject will begin receiving effective doses of a molecule that suppresses alloimmune responses, such as collagen compounds as described herein. Patients undergoing treatment will receive the compounds by oral administration, preferably either by oral feeding or intrapulmonary instillation into the recipient.

The dosage will be determined by a number of factors that will be known to the skilled artisan. The subject will receive at least three doses of the compounds per month from the time the subject is placed on the transplant list until the time of transplantation. In some cases, the dosages will be administered every alternate day for four days in order to receive at least three doses of the compound per month. In other cases, the dosages will be administered every alternate day for eight days, for a total dosage of five times per month prior to transplant. In other cases, the subject will receive the compounds at least once per week from the time the subject is placed on the transplant list until the time of transplantation. Depending on the subject, the compounds may be administered at least twice per week from the time the subject is place on the transplant list until the time of transplantation.

Example 10

It is further contemplated that treatment of a human subject who has received a transplant or that is suffer from a lung disease or disorder that involves autoimmunity to collagen for example Type V collagen with a molecule that suppresses alloimmune responses, preferably a collagen compound, will prevent or diminish the onset of acute or chronic pathology in the subject. As above, administration of the compounds can be administered by various means, including, either by oral feeding or by intrapulmonary or intravenous instillation into the recipient (patient).

Again, the dosage amounts will be determined by the skilled artisan based upon a number of factors known to the artisan. In most cases a given patient will likely receive at least three doses of the compounds per month for at least two months or until the symptoms of the disease or disorder improve. These dosages may take the form of one dose every alternate day for four days, as above, for the three doses for the month. The following month, the transplant subject will receive another round of one dose every alternate day for four days. This procedure can be repeated as needed as determined by the skilled artisan. Alternatively, the subject may receive one dose every alternate day for eight days, for a total of five doses for the month, during the months, as needed, following the transplant. In other aspects, the subject may receive the dosages in weekly increments or two times per week, etc., as determined by the skilled artisan.

While the invention has been illustrated and described in detail in the figures and foregoing description, the same is to be considered as illustrative and not restrictive in character, it being understood that only the preferred embodiments have been shown and described and that all changes and modifications that come within the spirit of the invention are desired to be protected. As well, while the invention was illustrated using specific examples, theoretical arguments, accounts, and illustrations, these illustrations and the accompanying discussion should by no means be interpreted as limiting the invention. All patents, patent applications, and references to texts, scientific treatises, publications, and the like referenced in this application are incorporated herein by reference in their entirety.

While exemplary embodiments incorporating the principles of the present invention have been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

REFERENCES

The following references, to the extent that they provide exemplary procedural or other details supplementary to those set forth herein, are specifically incorporated herein by reference.

Ayoub G, Terasaki P., "HLA-DR matching in multicenter, single-typing laboratory data." Transplantation 1982 May 33:515-7.

Bickerstaff, Xia, Pelletier, and Orosz, "Mechanisms of Graft Acceptance: Evidence That Plasminogen Activator Controls Donor-Reactive Delayed-Type Hypersensitivity Responses in Cardiac Allograft Acceptor Mice." 2000.

Birk O S, Gur S L, Elias D, et al. "The 60-kDa heat shock protein modulates allograft rejection." Proc. Natl. Acad. Sci. U.S.A. 1999; 96:5159-63.

Blankenberg, F., Robbins, R., Stoot, J., Vriens, P., Berry, G., Tait, J. and Strauss, H., "Radionuclide Imaging of Acute Lung Transplant Rejection With Annexin V," Chest, 2000; 117:834-840.

Burlingham W J, Jankowska-Gan E, VanBuskirk A M, Orosz C G, Lee J H, Kusaka S., "Loss of tolerance to a maternal kidney transplant is selective for HLA class II: Evidence from trans-vivo DTH and alloantibody analysis." Human Immunology, 2000; 61:1395-402.

Cai J, Lee J, Jankowska-Gan E, et al., "Minor H Antigen HA-1-specific Regulator and Effector CD8+ T Cells, and HA-1 Microchimerism, in Allograft Tolerance," J. Exp. Med. 2004; 199:1017-23.

Chen, Kuchroo, Inobe, Hafier, Weiner, "Regulatory T-cell clones induced by oral tolerance: suppression of autoimmune encephalomyelitis," Science, 265:1237-1240, 1994.

Chen, Inobe, Marks, Gonnella, Kuchroo, Weiner, "Peripheral deletion of antigen-reactive T cells in oral tolerance," Nature, 376:177-180, 1995.

Chiang, Mainardi, Seyer, "Type V(A-B) collagen induces platelet aggregation," J. Lab. Clin. Med., 95:99-107, 1980.

Cremer, Ye, Terato, Owens, Seyer, Kang, "Type XI collagen-induced arthritis in the Lewis rat: characterization of cellular and humoral immune responses to native types XI, V, and II collagen and constituent α-chains," J. Immunol. 153:824-832, 1994.

Fedoseyeva, Zhang, Orr, Levin, Buncke, Benichou, "De novo autoimmunity to cardiac myosin after heart transplantation and its contribution to the rejection process," J. Immunol., 162:6836-42, 1999.

Delclaux, S., Rezaiguia-Delaux, C., Delacourt, C., Brun-Buission, C., Lafuma and Hart A., "Alveolar neutrophils in endotoxin-induced and bacteria-induced acute lung injury in rats," Am. J. Physical Lung Cell Mol. Physiol., 273: L104-L112, 1997; 1040-0605/97.

Duquesnoy R J, Liu K, Fu X F, Murase N, Ye Q, Demetris A J., "Evidence for heat shock protein immunity in a rat cardiac allograft model of chronic rejection," Transplantation, 1999; 67:156-64.

Estenne M, Maurer J R, Boehler A, et al. "Bronchiolitis obliterans syndrome 2001: an update of the diagnostic criteria," J. Heart Lung Transplant 2002; 21:297-310.

Faria and Weiner, "Oral tolerance: mechanisms and therapeutic applications," Adv. Immunol., 73:153-264, 1999.

Garrovillo, Ali, Oluwole, "Indirect allorecognition in acquired thymic tolerance: induction of donor-specific tolerance to rat cardiac allografts by allopeptide-pulsed host dendritic cells," Transplantation, 68:1827-1834, 1999.

Garside and Mowat, "Mechanisms of oral tolerance." Crit. Rev. Immunol, 1997; 17(2):119-37. Hanson, Gorman, Oui, Cheah, Solomon, Trowsdale, "The human α2(XI) collagen gene (COL11A2) maps to the centromeric of the major histocompatibility complex on chromosome 6," Genomics, 5:925-931, 1989.

Hague M A, Mizobuchi T, Yasufuku K, et al. "Evidence for immune responses to a self-antigen in lung transplantation: role of Type V collagen-specific T cells in the pathogenesis of lung allograft rejection," J. Immunol. 2002 Aug. 1; 169: 1542-9.

Henningsen G M, Koller L D, Exon J H, Talcott P A, and Osborne C A, "A sensitive delayed-type hypersensitivity model in the rate for assessing in vivo cell-mediated immunity." J. Immunol. Methods. 1984 May 25; 70(2):153-65.

Hirt, You, Moller, Boeke, Starke, Spranger, Wottge, "Development of obliterative bronchiolitis after allogeneic rat lung transplantation: Implication of acute rejection and the time point of treatment," J. Heart Lung Transplant., 18:542-548, 1999.

Hudson B G, Tryggvason K, Sundaramoorthy M, Neilson E G., "Alport's syndrome, Goodpasture's syndrome, and Type IV collagen," N. Engl. J. Med. 2003; 348:2543-56.

Huang, Fuchimoto, Scheier-Dolberg, Murphy, Neville, Sachs, J. Clin. Invest., 105:173-181, 2000.

Ishido, Matsuoka, Matsuno, Nakagawa, Tanaka, "Induction of donor-specific hyporesponsiveness and prolongation of cardiac allograft survival by jejunal administration of donor splenocytes," Transplantation, 68:1377-1382, 1999.

Joo, Pepose, Stuart, "T-cell mediated responses in a murine model of orthotopic corneal transplantation," Invest. Ophthalmol. Vis. Sci., 36:1530-1540, 1995.

Kallio, E., Koskinen, P., Aavik, E., Vaali, K., and Lemstom, K., "Role of Nitric Oxide in Experimental Obliterative Bronchiolitis (Chronic Rejection) in the Rat," J. Clin. Invest., Vol. 100 No. 12, December 1997, 2984-2994.

Konomi, Hayashi, Nakayasu, Arima, "Localization of type V collagen and type IV collagen in human cornea, lung, and skin," Am. J. Pathol., 116:417-426, 1984.

Krensky and Clayberger, "HLA-derived peptides as novel immunosuppressives," Nephrol. Dial. Transplant., 12:865-878, 1997.

Lowry, Marghesco, Blackburn, "Immune mechanisms in organ allograft rejection. VI. Delayed-type hypersensitivity and lymphotoxin in experimental renal allograft rejection," Transplantation, 40:183-188, 1985.

Madri and Furthmayr, "Isolation and tissue localization of type AB2 collagen from normal lung parenchyma," Am. J. Pathol., 94:323-332, 1979.

Madri and Furthmayr, "Collagen polymorphism in the lung," Human Pathology, 11:353-366, 1980.

Marck, Prop, Widevuur, "Lung transplantation in the rat. III. Functional studies in iso- and allografts," J. Surgical Res., 35:149-158, 1983.

Mares D C, Heidler K M, Smith G N, et al., "Type V Collagen Modulates Alloantigen-Induced Pathology and Immunology in the Lung," Am. J. Respir. Cell Mol. Biol., 2000 Jul. 1; 23:62-70.

Matsumura, Marchevsky, Zuo, Kass, Matloff, Jordan, "Assessment of pathological changes associated with chronic allograft rejection and tolerance in two experimental models of rat lung transplantation," Transplantation, 59:1509-1517, 1995.

Morris and Bachinger, "Type XI collagen is a heterotrimer with the composition (1.α, 2.α, 3.α) retaining non-triple helical domains," J. Biological Chem., 262:11345-11350, 1987.

Murphy, Magee, Alexander, Waaga, Snoeck, Vella, Carpenter, Sayagh, "Inhibition of allorecognition by a human class II MHC-derived peptide through the induction of apoptosis," J. Clin. Invest., 103:859-867, 1999.

O'Leary, Evans, Zuckerman, "In Vivo Dexamethasone Effects on Neutrophil Effector Functions in a Rat Model of Acute Lung Injury," Inflammation, 21:6, 1997.

Oluwole, Chowdhury, Jin, Hardy, "Induction of transplantation intolerance to rat cardiac allografts by intrathymic inoculation of allogeneic soluble peptides," Transplantation, 56(6):1523-1527, 1993.

Piez, K. A., Eigher, E. A. and Lewis, M. S. Biochemistry, 2, 58; 1996.

Prop, Nieuwenhuis, Wildevuur, "Lung allograft rejection in the rat. I. Accelerated rejection caused by graft lymphocytes," Transplantation, 40:25-30, 1985.

Rodriguez D S, Jankowska-Gan E, Haynes L D, et al., "Immune regulation and graft survival in kidney transplant recipients are both enhanced by human leukocyte antigen matching," Am. J. Transplant 2004; 4:537-43.

Sayagh, Watschinger, Carpenter, "Mechanisms of T cell recognition of alloantigen," Transplantation, 57:(9)1295-1302, 1994.

Sayegh, Khoury, Hancock, Weiner, Carpenter, "Induction of immunity and oral tolerance with polymorphic class II major histocompatibility complex allopeptides in the rat," Proc. Natl. Acad. Sci., 89: 7762-7766, 1992.

Sayegh and Krensky, "Novel immunotherapeutic strategies using MHC derived peptides," Kidney Int. Suppl. 53:S13-20, 1996.

Schwarze U, Atkinson M, Hoffman G G, Greenspan D S, Byers P H., "Null alleles of the COL5A1 gene of Type V collagen are a cause of the classical forms of Ehlers-Danlos syndrome (types I and II)," Am. J. Hum. Genet. 2000; 66:1757-65.

Sekine, Nowen, Heidler, Van Rooijen, Brown, Cummings, Wilkes, "Role of passenger leukocytes in allograft rejection—Effect of depletion donor alveolar Macrophages on the local production of TNF-alpha, T helper 1/T helper 2 cytokines, IgG subclasses, and pathology in a rat model of lung transplantation," J. Immunol, 159:4084-4093, 1997.

Sharples L D, McNeil K, Stewart S, Wallwork J., "Risk factors for bronchiolitis obliterans: a systematic review of recent publications," J. Heart Lung Transplant, 2002; 21:271-81.

Smith Jr., Williams, Brandt, "Interaction of proteoglycans with pericellular (1α, 2α, 3α) collagens of cartilage," J. Biol. Chem., 260:10761-10767, 1985.

Stark and Ostrow, "Training Manual Series, Laboratory Animal Technician," American Association for Laboratory Animal Science, 181-182, 1990.

Trulock, "Lung transplantation," Am. J. Respir. Crit. Care Med., 155:789-818, 1997.

VanBuskirk, Wakely, Sirak, Orosz, "Patterns of allosensitization in allograft recipients: long-term allograft acceptance is associated with active alloantibody production in conjunction with active inhibition of alloreactive delayed-type hypersensitivity," Transplantation, 65:1115-1123, 1998.

van den Berg J W, Hepkema B G, Geertsma A, et al., "Long-term outcome of lung transplantation is predicted by the number of HLA-DR mismatches," Transplantation 2001; 71:368-73.

Westra, Prop, Kuijpers, "A paradox in heart and lung rejection," Transplantation, 49:826-828, 1990

Whitacre, Gienapp, Orosz, Bitar, "Oral tolerance in experimental autoimmune encephalomyelitis. III. Evidence for clonal anergy," J. Immunol., 147:2155-2163, 1991.

Wilkes, Heidler, Bowen, Quinlan, Doyle, Cummings, Doerschuk, "Allogeneic bronchoalveolar lavage cells induce the histology of acute lung allograft rejection, and deposition of IGg2a in recipient murine lungs," J. Immunol., 155: 2775-2783, 1995.

Wilkes, Thompson, Cummings, Bragg, Heidler, "Instillation of allogeneic lung macrophages and dendritic cells cause differential effects on local IFY-.gamma. production, lymphocytic bronchitis, and vasculitis in recipient murine lungs," J. Leukoc. Biol. 64:578-586, 1998.

Wilkes, Bowman, Cummings, Heidler, "Allogeneic bronchoalveolar lavage cells induce the histology and immunology of lung allograft rejection in recipient murine lungs. Role of ICAM-1 on donor cells," Transplantation, 67(6):890-896, 1999.

Wilson, Ebringer, Ahmadi, Wrigglesworth, Tiwana, Fielder, Binder, Ettelaie, Cunningham, Joannou, Bansal, "Shared amino acid sequences between major histocompatibility complex class II glycoproteins, type XI collagen and *Proteus mirabilis* in rheumatoid arthritis," Ann. Rheum. Dis., 54:216-220, 1995.

Woessner Jr., "The determination of hydroxyproline in tissue and protein samples containing small proportions of this immino acid," Arch. Biochem. Biophys. 93:440-447, 1961.

Yagyu, Steinhoff, Schfers, Dammenhayn, Haverich, Borst, "Comparison of mononuclear cell populations in brochoalveolar lavage fluid in acute rejection after lung transplantation and *Mycoplasma* infection in rats," J. Heart Transplant., 9:516-525, 1990.

Yamagami, Tsuru, Ohkawa, Endo, Isobe, "Suppression of allograft rejection with anti-alpha beta T cell receptor antibody in rat corneal transplantation," Transplantation, 67:600-604, 1999.

Yasufuku K, Heidler K M, O'Donnell P W, et al., "Oral tolerance induction by Type V collagen downregulates lung allograft rejection," Am. J. Respir. Cell Mol. Biol. 2001 Jul. 25, 26-34.

Yasufuku K, Heidler K M, Woods K A, et al., "Prevention of bronchiolitis obliterans in rat lung allografts by Type V collagen-induced oral tolerance," Transplantation, 2002; 73:500-5.

Yoshino, Quattrocchi, Weiner, "Suppression of antigen-induced arthritis in Lewis rats by oral administration of type II collagen," Arthritis Rheum. 38: 1092-1096, 1995.

Yousem, Berry, Cagle, Chamberlain, Husain, Hruban, Marchevsky, Ohori, Ritter, Stewart, Tazelaar, "Revision of the 1990 working formulation for the classification of pulmonary allograft rejection: Lung rejection study group," J. Heart Lung Transplant, 15:1-15, 1996.

Zheng, Markees, Hancock, Li, Greine, Li, Mordes, Sayegh, Rossini, Strom, "CTLA4 signals are required to optimally induce allograft tolerance with combined donor-specific transfusion and anti-CD154 monoclonal antibody treatment," J. Immunol., 162:4983-4990, 1999.

We claim:

1. A method for screening a patient awaiting a lung transplant for an elevated risk of lung transplant rejection, the method comprising:
   contacting at least a portion of a sample from the patient with Type V collagen or an antigenic component thereof; and
   measuring a Type V collagen-specific immune response;
   wherein the lung transplant rejection comprises chronic rejection or bronchiolitis obliterans; and
   wherein the presence of a Type V collagen-specific immune response indicates an elevated risk of lung transplant rejection.

2. The method of claim 1 wherein the measuring a Type V collagen-specific immune response comprises measuring the level of Type V collagen-specific antibodies in the sample.

3. The method of claim 2 wherein the Type V collagen-specific antibody is measured using Type V collagen-coated beads.

4. The method of claim 1 wherein the measuring a Type V collagen-specific immune response comprises measuring a Type V collagen-specific T cell response.

5. The method of claim 1 wherein the measuring a Type V collagen-specific immune response comprises measuring a Type-V collagen-specific delayed-type hypersensitivity response.

6. The method of claim 1 wherein the sample is selected from the group consisting of blood, serum, interstitial lung fluid, sputum, mucus and tissue.

* * * * *